United States Patent
Yoshiike et al.

(10) Patent No.: US 6,796,799 B1
(45) Date of Patent: Sep. 28, 2004

(54) BEHAVIOR DETERMINING APPARATUS, CARE SYSTEM, CARE RESIDENCE AND BEHAVIOR INFORMATION SPECIFYING APPARATUS AND SYSTEM

(75) Inventors: Nobuyuki Yoshiike, Ikoma (JP); Akiyoshi Hattori, Yahata (JP); Katsuya Morinaka, Hirakata (JP); Shigeyuki Inoue, Katano (JP); Shinji Tanaka, Kadoma (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 532 days.

(21) Appl. No.: 09/621,688

(22) Filed: Jul. 21, 2000

(30) Foreign Application Priority Data

| Jul. 23, 1999 | (JP) | ........................................ H11-209707 |
| Aug. 5, 1999 | (JP) | ........................................ H11-223100 |
| Aug. 31, 1999 | (JP) | ........................................ H11-245818 |

(51) Int. Cl.[7] .............................................. G09B 19/00
(52) U.S. Cl. ...................................... 434/236; 702/188
(58) Field of Search ................................ 434/236, 237, 434/238; 702/188

(56) References Cited

U.S. PATENT DOCUMENTS

| 6,002,994 A | * | 12/1999 | Lane et al. | .................. | 702/188 |
| 6,108,685 A | * | 8/2000 | Kutzik et al. | ............... | 709/200 |

FOREIGN PATENT DOCUMENTS

| EP | 0 558 975 A1 | 9/1993 |
| GB | 2 179 186 A | 2/1987 |
| JP | 2-51504 | 4/1990 |
| JP | 4-56561 | 2/1992 |
| JP | 4-354000 | 12/1992 |
| JP | 5-92040 | 4/1993 |
| JP | 5-322262 | 12/1993 |
| JP | 6-502249 | 3/1994 |
| JP | 6-168366 | 6/1994 |
| JP | 8-241476 | 9/1996 |
| JP | 9-120457 | 5/1997 |
| JP | 9-131382 | 5/1997 |
| JP | 10-151086 | 6/1998 |
| JP | 10-248816 | 9/1998 |
| JP | 10-332823 | 12/1998 |
| JP | 11-144172 | 5/1999 |
| WO | WO 92/08148 | 5/1992 |
| WO | WO 93/16636 | 9/1993 |

OTHER PUBLICATIONS

European Search Report dated Nov. 8, 2000 for EP 00115682.
M. Makikawa et al. "Ambulatory Monitoring of Physical Activites and Behavior in Daily Life" May 1995, English translation.
Japanese Office Action dated Nov. 5, 2002 (with partial English translation).
Japanese Office Action dated Nov. 19, 2002 (with partial English translation).

* cited by examiner

Primary Examiner—John Edmund Rovnak
(74) Attorney, Agent, or Firm—Smith, Gambrell & Russell, LLP

(57) ABSTRACT

A behavior determining apparatus, has first detective means for detecting the behavior of a given subject person;
  second detective means for detecting the operation of a given appliance;
  recording means for recording one or more combined patterns of behavior of said subject person and operation of said appliance;
  determining means for comparing the behavior of said subject person detected by said first detective means and the operation of said appliance detected by said second detective means with patterns recorded in said recording means to determine whether or not a combination of behavior of said subject person and operation of said appliance substantially accords with any of said patterns; and
  output means for outputting the determined results of the said determining means.

8 Claims, 27 Drawing Sheets

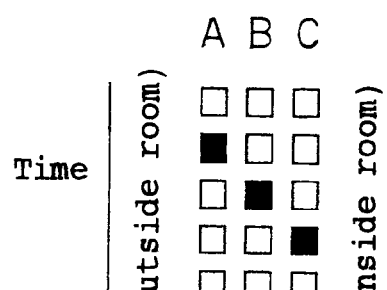
Fig. 19 (1)
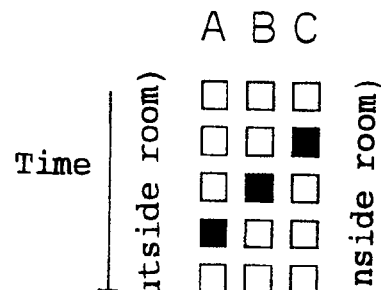
Fig. 19 (2)
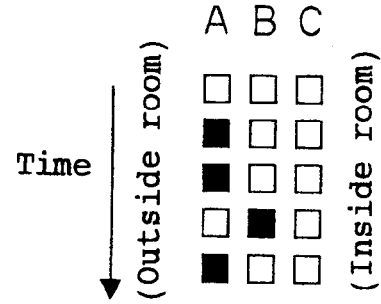
Fig. 19 (3)
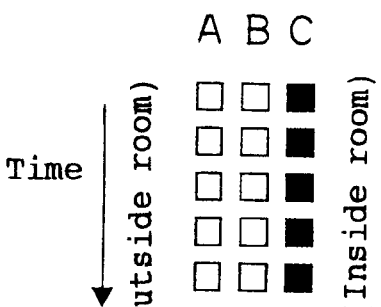
Fig. 19 (4)

Fig. 21
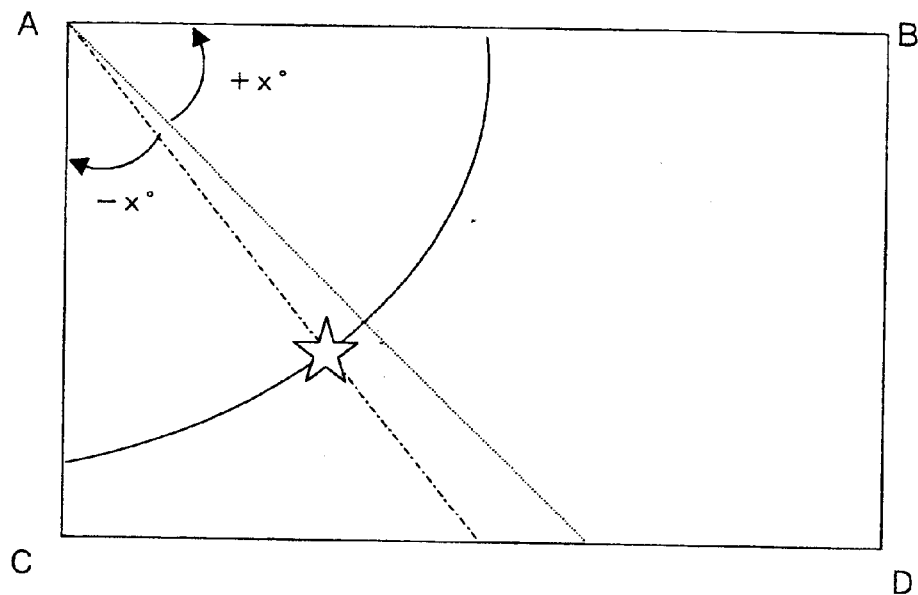
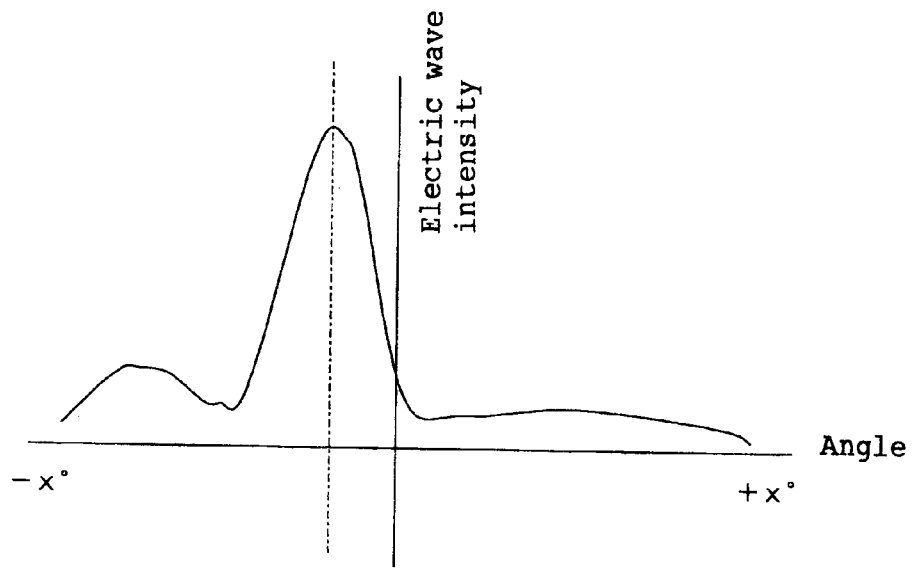

Fig. 23
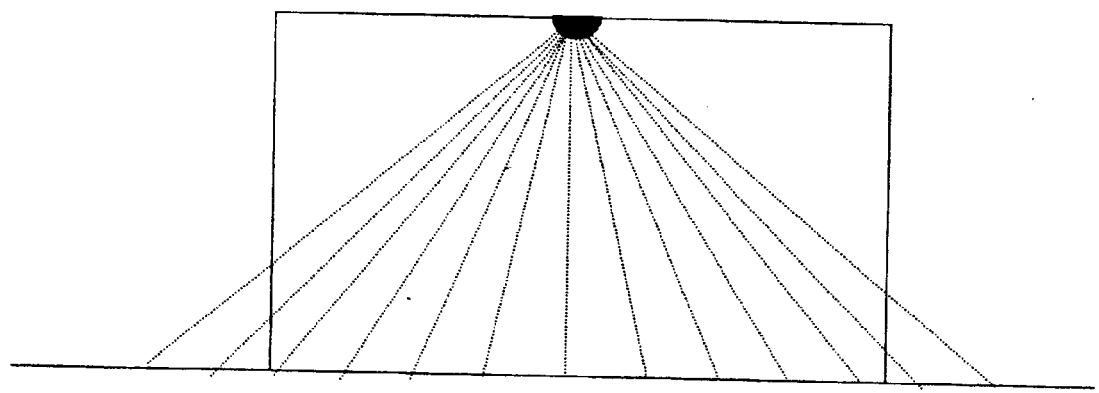
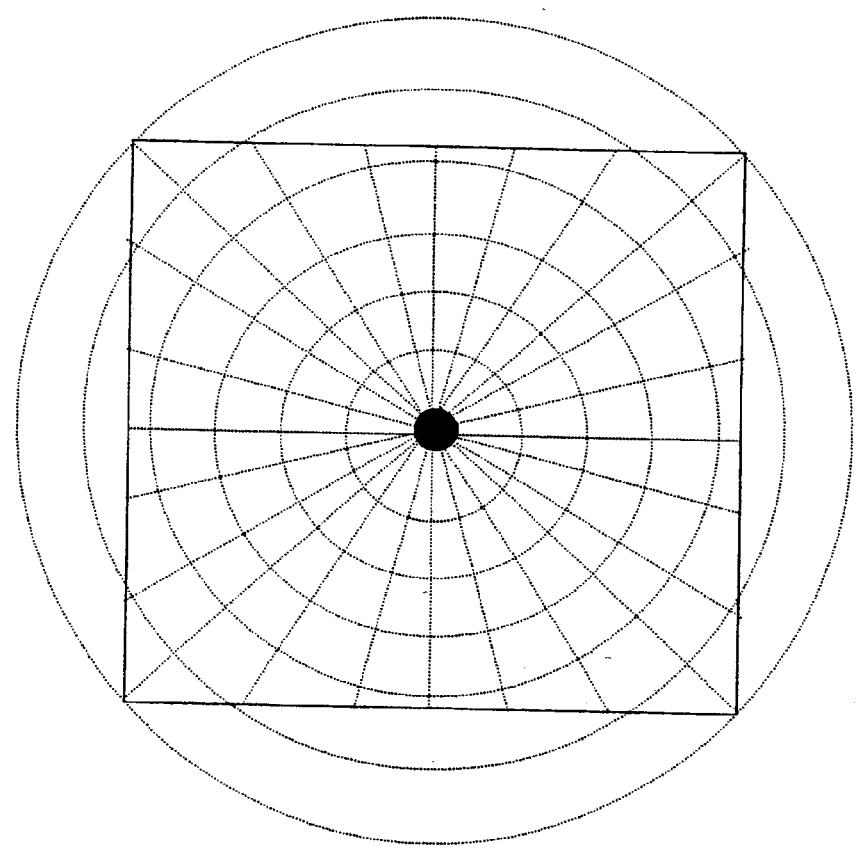

BEHAVIOR DETERMINING APPARATUS, CARE SYSTEM, CARE RESIDENCE AND BEHAVIOR INFORMATION SPECIFYING APPARATUS AND SYSTEM

BACKGROUND OF THE INVENTION

1. Field of the Invention

The present invention relates to a behavior determining apparatus for determining whether or not a pattern regarding behaviors of a given subject person and an actual behavior of that person are substantially identical; a behavior determining apparatus for determining whether or not the pattern of actions of a given device and an actual action of that device are substantially identical; a care system for accurately specifying the behavior of a subject person and taking care of that person; a care residence equipped with that care system; a measuring method, pertaining to the measurement of actions and behaviors in varying states of humans, animals, machines or the like, for measuring those actions and behaviors; an apparatus using that method; and a system including that apparatus.

2. Description of the Related Art

Behavior determining apparatuses according to the prior art include, for instance, an apparatus for determining the behaviors of senior citizens living alone. To cite a specific example, there is an apparatus that keeps on recording for a month or any other prescribed period how many times, both cumulatively and per unit length of time, the "pour" button of an automatic thermos used in the residence of a senior citizen living alone is pressed; records the average daily frequency of button pressing as the pattern of the resident's use of the thermos; and, after these preliminary steps, detects his or her actions to pour hot water from the thermos; compares the frequency of the actions with the recorded pattern to determine whether or not the actual frequency is substantially identical with the pattern observed in advance. The apparatus determines the senior citizen's behaviors and, if for instance he or she does not use the thermos when its use is expected according to the pattern observed in advance, issues to a management center, which is connected to the behavior determining apparatus, an alarm that he or she may be ill. Another behavior determining apparatus according to the prior art, as the foregoing apparatus compares the actual use of the thermos with the pattern observed in advance, detects the use of city water with a sensor fitted to the water discharge meter and determines the behaviors of the senior citizen living alone by comparing the detected act of actual water consumption and a pattern observed in advance and determining whether or not the detected act and the pre-observed pattern are substantially identical.

Furthermore, based on a similar principle to the idea underlying the apparatuses which compare and determine the presence or absence of substantial identity between the actions of a device, such as an automatic thermos, and the pre-observed pattern of its use, another behavior determining apparatus directly detects human behaviors, instead of the actions of a device, and determines whether or not the subject person's behaviors are substantially identical with a pre-recorded pattern of his or her behaviors. The means of directly detecting the person's behavior may be, for instance, a pyro-electric type infrared ray sensor installed on the ceiling of a room or a passage the person frequently passes. If the sensor detects his or her passage frequently enough, the person can be assumed to be living without trouble.

In recent years, with the aging of the national population, care of senior citizens has become a matter of grave social concern, with particular emphasis on those suffering from senile dementia or manifesting wandering symptoms, and the above-described and various other techniques have been proposed to address this issue. It is considered very useful in taking care of these senior citizens to have some means for keeping track of the behaviors of each and, if anything wrong is found, notifying the person concerned and someone else responsible for his or her care. Apart from senior citizens, if, for instance, behavioral patterns are specified by measuring and analyzing human behaviors, it will become possible to control illumination, air conditioning and so forth and thereby to make their operation more pleasant and safer for residents.

Furthermore, the effectiveness of measurement is not limited to human behaviors, but the behaviors of animals or machines can also be measured usefully. It could help reveal some unknown ecological aspects of animals, or measurement of states and actions of machines could contribute to their more efficient and safer operation and accordingly to greater efficiency of productive activities as a whole.

In understanding the behaviors of a human body or a inanimate object, it is essential to determine "who (or what)" does "what" and "where," because the individual or the object should be specified, its position in the room pinpointed, and its action and attitude detected.

An individual or a specific object may be specified by RF-ID or visual perception of CCD images. The RF-ID is a system whereby specifying information from a tag (also called a transponder; hereinafter to be referred to as a tag throughout) fitted to a moving body such as a human body or an inanimate one is received by an antenna (also called a reader; hereinafter to be referred to as an antenna throughout) as an electric wave of a specific frequency, and the object is thereby specified automatically.

This system can be broadly classified into two types by the reach of tag reading. One is a short-range type using a low frequency, for which the distance between the tag and the antenna is around 50 cm or less. The usual way of using this type is to hold the tag closely over the antenna or to sew the tag into a cuff of the slacks so that information from the tag can be read by an antenna installed on the floor. The other is a long-range type using a microwave, for which the distance between the tag and the antenna is more than 1 m. In this arrangement, the tag is mounted on a part of the human body or the object, and when the bearer of the tag passes near the antenna, information from the tag can be read by the antenna without being noticed by the bearer of the tag.

On the other hand, by the method of visual perception of CCD images, a CCD camera shoots a human or an inanimate body passing an entrance/exit, extracts characteristic quantities such as the personal face or the shape of or any mark on the object by visual perception and, by comparing them with inherent characteristic quantities registered in advance, the person or the specific object is specified.

Methods for specifying the position of a human or an inanimate body indoors include extraction from CCD images and extracting from temperature distribution information obtained with a two-dimensional infrared sensor. A method proposed for use in a very large building is to determine an approximate position from the intensities of electric waves from a plurality of base stations, using the personal handyphone system (PHS).

Older methods proposed for detecting actions and/or attitudes include ones by which a static condition and a dynamic condition are distinguished from each other by using a passometer, a mercury switch or the like. Recently proposed methods include, as various acceleration sensors and gyro sensors (angular acceleration sensors) have been improved in performance, ones based on the detection of the walking condition, the inclination of the body, the walking direction and/or other factors using these improved sensors.

BRIEF SUMMARY OF THE INVENTION

Object of the Invention

However, since conventional behavior determining apparatuses relying on the actions of an automatic thermos or a water discharge meter can hardly keep track of everyday life activities of the subject person on a real time basis. Therefore, even if something wrong occurs with the subject person, it will take some time, a full day for instance, until that unusual state is specified as such.

Furthermore, because a pyro-electric infrared ray sensor would react to, for instance, the fluttering of a curtain when the window is opened or the movement of a small pet animal, such as a dog or a cat, a conventional behavior determining apparatus using this kind of sensor cannot accurately detect human behaviors either.

Furthermore, there is another means for directly detecting human behaviors than the pyro-electric infrared ray sensor, known as an in-bed state sensor, which detects whether or not the subject person is in bed. For instance, if the subject person gets up in the middle of night, goes to the kitchen and toilet and returns to the bed, a pyro-electric infrared ray sensor and/or an in-bed state sensor can detect that he or she once left the bed late at night, went to the kitchen and toilet and returned to the bed. However, the conventional behavior determining apparatus cannot tell whether the person felt thirsty, went to the kitchen, opened the refrigerator door, drank something and then went to the toilet or left the bed and went to the kitchen and the toilet all with no conscious purpose. If, for instance, a senior person behaves meaninglessly, he or she may be suffering from senile dementia, but the conventional behavior determining apparatus cannot be used for detecting a symptom of senile dementia.

The present invention, in view of the above-noted problems, is intended to provide a behavior determining apparatus for detecting the behaviors of the subject person more accurately.

Also, the invention is also intended to accurately specify the behaviors of the subject person and provide a care system for taking care of the subject person on that basis. The invention is further intended to provide a care residence equipped with that care system.

Also, the above-described behavior determining apparatus according to the prior art issues an alarm when any actual action of the subject device and a pre-recorded pattern are not identical with each other within a prescribed period of time or within a prescribed range of action variations, or when any actual behavior of the subject person and a pre-recorded pattern are not identical with each other within a prescribed period of time or within a prescribed range of behavior variations. Therefore if, for instance, the customary hours of the subject person's visit to a hospital have changed and, when he or she is supposed to be in bed according to the pre-recorded pattern, the subject person is cooking in the kitchen, the differences from the person's behaviors and the device's recorded pattern will actuate an alarm to the subject person.

The subject person can stop the alarm issued to him but cannot respond to it in any other way. More specifically, after the alarm, the person cannot add to the records in the behavior determining apparatus the behavior or action regarding which the alarm was issued as a new element of pattern, or replace the existing pertinent pattern with the new one.

The present invention, with these problems taken into account, is intended to provide a behavior determining apparatus for notifying, if any behavior of the subject person or any action of the subject device is not substantially identical with a pre-recorded pattern, that non-identity and permitting the inputting of a response to that notification.

The invention is further intended to provide a behavior determining apparatus for adding, on the basis of the response from the notification, the behavior of the subject person or the action of the subject device not substantially identical with the pre-recorded pattern to the records as a new element of pattern, or replacing all or part of the recorded pattern with a new pattern or a new element of pattern.

In addition, the invention is intended to provide a care system for accurately specifying any behavior of the subject person, accurately notifying the behavior, permitting the inputting of the person's response to the notification, and providing care to the person on the basis of that response. The invention is further intended to provide a care residence equipped with the care system.

Although many methods have been proposed for the purpose of detecting "who (or what)" does "what" and "where" as described above, none of them can perform anymore than a single function. In other words, none of them can determine in an integrated way "who (or what)" does "what" and "where." Although RF-ID can specify a specific person or an inanimate object entering a room, if a plurality of persons enter a room, it will be impossible to determine "who (or what)" is "where" by a method for locating the position of a person or an inanimate object. An acceleration sensor may be able to detect, for instance, the attitude of the subject, but not the position in which the attitude is taken.

The above-described methods involve a number of additional problems. Regarding RF-ID cited as a method for specifying an individual person or a specific inanimate object, the short-range type requires, because of the short distance of communication between the tag and the antenna, the tag to be consciously held closely over the antenna. The long-range type, on the other hand, because of its long distance of communication between the tag and the antenna, may sense not only passage through the entrance/exit but also passage beside the antenna by the person who does not actually enter the room. Specification of an individual person or a specific inanimate object from a CCD image, because of the need to extract characteristic quantities from the image, involves the problem of impossibility to specify the person if his or her face is made invisible by an obstacle in-between or by the darkness of night.

The present invention, with these problems taken into account, is intended to provide a behavior measuring method, apparatus and system capable of acquiring in a composite way the aforementioned behavioral information on "who" does "what" and "where" and acquiring readily and accurately behavioral information adaptable to many different applications by accurately keeping track of the entrance into or the exit from a room by a human body or an inanimate body, specifying the person or the object at that point of time, and detecting the position and attitude of that human body ortho inanimate object on that basis.

SUMMARY OF THE INVENTION

The $1^{st}$ invention of the present invention is (corresponding to claim 1) a behavior determining apparatus, comprising:

first detective means for detecting the behavior of a given subject person;

second detective means for detecting the operation of a given appliance;

recording means for recording one or more combined patterns of behavior of said subject person and operation of said appliance;

determining means for comparing the behavior of said subject person detected by said first detective means and the operation of said appliance detected by said second detective means with patterns recorded in said recording means to determine whether or not a combination of behavior of said subject person and operation of said appliance substantially accords with any of said patterns; and output means for outputting the determined result of the said determining means.

The $2^{nd}$ invention of the present invention is (corresponding to claim 12) a care system, comprising:

first detective means for detecting the behavior of a given subject person;

second detective means for detecting the operation of a given appliance;

specifying means for accurately specifying the behavior of said subject person on the basis of the behavior of said subject person detected by said first detective means and the operation of said appliance detected by said second detective means; and information providing means with an information item established about care of said subject person for selecting said established information items on the basis of the behavior of said subject person specified by said specifying means to provide the selected information item.

The $3^{rd}$ invention of the present invention is (corresponding to claim 13) a care system comprising:

first detective means for detecting the behavior of a given subject person;

second detective means for detecting the operation of a given appliance;

specifying means for accurately specifying the behavior of said subject person on the basis of the behavior of said subject person detected by said first detective means and the operation of said appliance detected by said second detective means; and control means for controlling the operation of said appliance on the basis of the behavior of said subject person specified by said specifying means.

The 4th invention of the present invention is (corresponding to claim 14) a care system comprising:

first detective means for detecting the behavior of a given subject person;

second detective means for detecting the operation of a given appliance;

specifying means for accurately specifying the behavior of said subject person on the basis of the behavior of said subject person detected by said first detective means and the operation of said appliance detected by said second detective means; and notifying means for notifying the behavior of said subject person specified by said specifying means.

The $5^{th}$ invention of the present invention is (corresponding to claim 21) a behavior determining apparatus comprising:

detective means for detecting the behavior of a given subject person;

recording means for recording one or more patterns regarding to behavior of said subject person;

determining means for comparing the behavior of said subject person detected by said detective means with patterns recorded in said recording means to determine whether the behavior of said subject person substantially accords with any of said patterns or not;

notifying means for notifying the information about the result if NO is the result determined by said determining means; and input means for inputting the response of said subject person to the information notified by said notifying means.

The $6^{th}$ invention of the present invention is (corresponding to claim 22) a behavior determining apparatus comprising:

detective means for detecting the operation of a given appliance;

recording means for recording one or more patterns regarding to operation of said appliance;

determining means for comparing the operation of said appliance detected by said detective means with patterns recorded in said recording means to determine whether or not the operation of said appliance substantially accords with any of said patterns;

notifying means for notifying the information about the result if NO is the result determined by said determining means; and input means for inputting the response of said subject person to the information notified by said notifying means.

The $7^{th}$ invention of the present invention is (corresponding to claim 26) a behavior determining apparatus comprising:

first detective means for detecting the behavior of a given subject person;

second detective means for detecting the operation of a given appliance;

specifying means for accurately specifying the behavior of said subject person on the basis of the behavior of said subject person detected by said first detective means and the operation of said appliance detected by said second detective means;

recording means for recording one or more accurate patterns regarding behavior of said subject person, based at least on the behavior of said subject person and the operation of said appliance;

determining means for comparing the accurate behavior of said subject person specified by said specifying means with patterns recorded in said recording means to determine whether the accurate behavior of said subject person substantially accords with any of said patterns or not;

notifying means for notifying the information about the result if NO is the result determined by said determining means; and input means for inputting the response of said subject person to the information notified by said notifying means.

The $8^{th}$ invention of the present invention is (corresponding to claim 35) a care system, comprising:

first detective means for detecting the behavior of a given subject person;

second detective means for detecting the operation of a given appliance;

specifying means for accurately specifying the behavior of said subject person on the basis of the behavior of said subject person detected by said first detective means and the operation of said appliance detected by said second detective means;

notifying means for notifying the accurate behavior of said subject person specified by said specifying means;

input means for inputting the response of said subject person to the information item notified by said notifying means; and information providing means with an information item established about care of said subject person for selecting said established information items on the basis of the behavior of said subject person input by said inputting means to provide the selected information item.

The $9^{th}$ invention of the present invention is (corresponding to claim 36) a care system comprising:

first detective means for detecting the behavior of a given subject person;

second detective means for detecting the operation of a given appliance;

specifying means for accurately specifying the behavior of said subject person on the basis of the behavior of said subject person detected by said first detective means and the operation of said appliance detected by said second detective means;

notifying means for notifying the accurate behavior of said subject person specified by said specifying means;

input means for inputting the response of said subject person to the information item notified by said notifying means; and control means for controlling the operation of the given appliance on the basis of the response of said subject person inputted by said input means.

To solve the above problems, the entrance/exit of a human body or a lifeless body into/out of the room is accurately grasped by means for detecting the moving direction and at this point, each individual person or thing is specified by using the RF-ID. By accurately measuring the timing of room entrance/exit, the trouble of holding a tag over the antenna is solved which has so far been a problem in a short-range type RF-ID and an erroneous judgement made in case of a human body or a lifeless body passing by the antenna without entering the room can be also solved which has been a problem in a long-range type RF-ID.

Besides, since a specific human body or lifeless body entering the room once can be grasped as mentioned above, the position, the posture or the like of the specific human body or lifeless body can be detected/grasped. By means of a sensor fitted to part of a human body or lifeless body, for example, his or her posture is detected and the information about a human body or a lifeless body present in the adjacent room is also received by the base station in the exchange of the posture information with the base station. Since the human body or lifeless body present in this room is specified beforehand, however, the information about the human body or lifeless body present in this room can be clearly distinguished from the information about the human body or lifeless body present in the adjacent room.

A behavioral information specifying apparatus according to the present invention, comprising an RF-ID and means provided at the doorway of a room for detecting the moving direction, one or more position detective means, the above RF-ID, means for detecting the moving direction and sensor signal processing means for evaluating the behavioral information from the position detective means provided in the room, is featured by allowing a human or lifeless body to bear means for determining the status of the human or lifeless body.

The above configuration makes it possible, according to the present invention, to specify a human or lifeless body entering the room and to accurately measure individual behavioral information items such as position in the room, posture and physiological state by means of a behavioral information specifying apparatus.

Besides, by communicating with the base station wirelessly and further connecting the base station to network stations, status determining means fitted to a human or lifeless body can manage the behavioral information of human or lifeless bodies in rooms and in a specific space altogether and can grasp the behavior of human or lifeless bodies in the whole building at the real time, while innumerable applications such as detection of abnormalities, control of air conditioning/illumination and security are thinkable.

BRIEF DESCRIPTION OF THE DRAWINGS

FIG. 19 shows an example of movement detection by the moving direction detector in embodiment 8 of the present invention;

FIG. 21 shows a measurement example regarding the human body position specification method in embodiment 10 of the present invention;

FIG. 23 shows outline type drawings relating to position specifying unit using a two dimensional infrared ray sensor in the behavior information specifying apparatus in embodiment 11 of the present invention;

DESCRIPTION OF SYMBOLS

Figure 1:
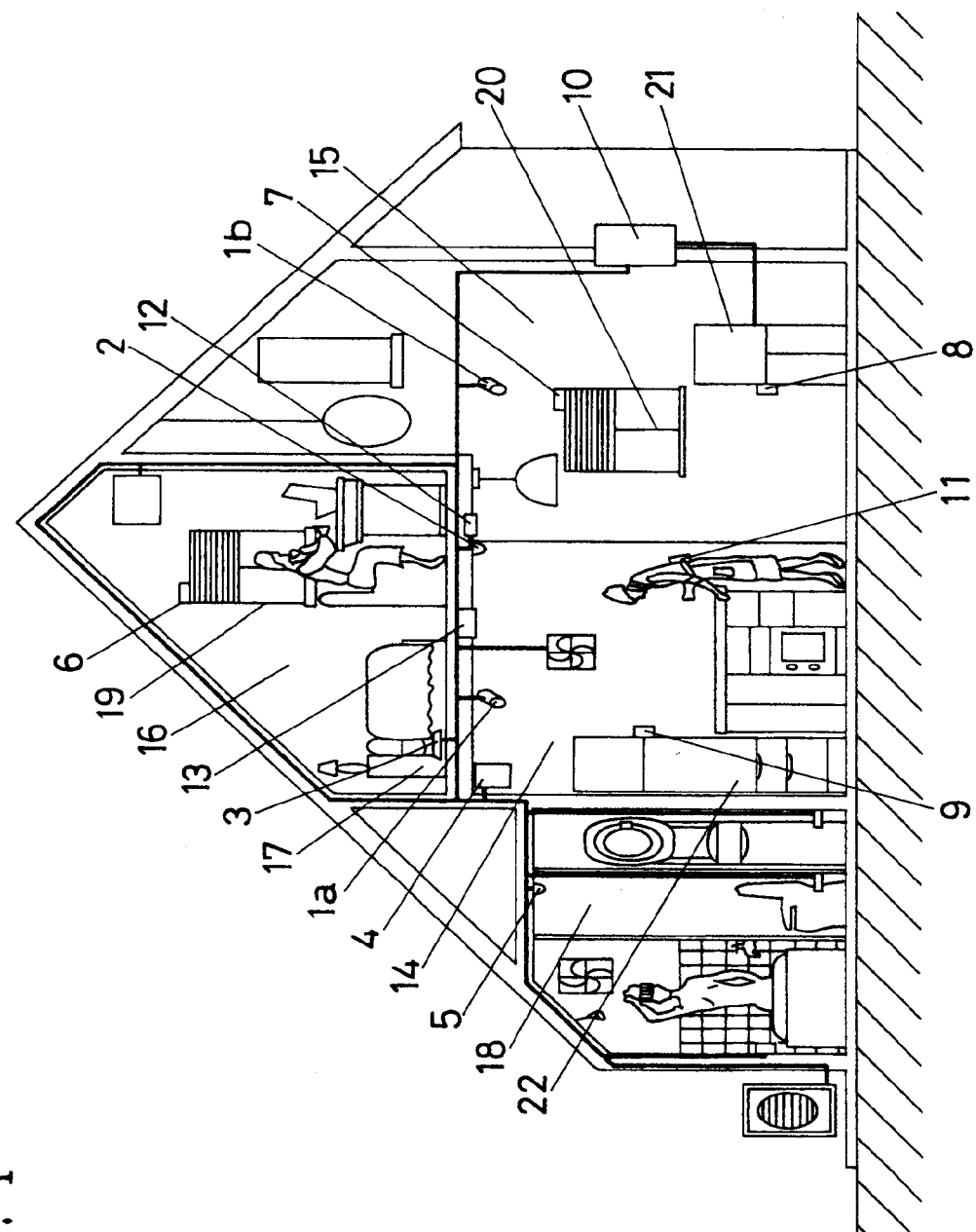
FIG. 1 is a drawing for explaining the location of each component unit when the several component units configuring the behavior determining apparatus of embodiment 1 of the present invention are installed in various locations in a residence, etc.

1 CCD camera
2 Infrared ray sensor
3 In-bed state sensor
4 Air quality sensor
5 Toilet sensor
6 Window open/close detector
7 Window open/close detector
8 TV power on/off detector
9 Refrigerator door open/close detector
10 Management unit
11 Personal information terminal (PIT)
12 Transmitter/receiver
13 Loudspeaker
14 Kitchen
15 Living room
16 Bedroom
17 Bed
18 Toilet
19 Window
20 Window
21 TV set
22 Refrigerator
23 Recording unit
24 Determining unit
25 Output unit
26 Alarm transmitter
27 Notifying unit
28 Management unit
29 Specifying unit
30 Information providing unit
31 Control unit
32 Notifying unit
101 CCD camera
102 Infrared ray sensor
103 In-bed state sensor
104 Air quality sensor
105 Toilet sensor
106 Window open/close detector
107 Window open/close detector
108 TV power on/off detector
109 Refrigerator door open/close detector
110 Management unit
111 PIT
112 Transmitter/receiver
113 Loudspeaker
114 Kitchen
115 Living room
116 Bedroom
117 Bed
118 Toilet
119 Window
120 Window
121 TV set
122 Refrigerator
123 First recording unit
124 Determining unit
125 Output unit
126 Input unit
127 Second recording unit
128 Learning unit
129 Management unit
130 First recording unit
131 Specifying unit
132 Determining unit
133 Output unit
134 Input unit
135 Second recording unit
136 Learning unit
137 Management unit
138 Specifying unit
139 Output unit
140 Input unit
141 Information providing unit
142 Control unit
201 Human body
202 RF-ID
203 Tag
204 Antenna
205 Moving direction detector
206 Position specifying unit
207 Sensor signal processor
208 Electric wave intensity analyzer
209 Personal portable terminal
210 Antenna for measuring electric wave intensity
211 Indoors
212 Transmitter 213 Base station
214 Other base station
215 Central station
216 Acceleration sensor
217 Rate gyro
218 Antenna
219 Signal processor
220 Alarm buzzer
221 Interface for optional sensor
222 Network

DETAILED DESCRIPTION OF THE PREFERRED EMBODIMENTS (Embodiment 1)

First, a configuration of a behavior determining apparatus according to Embodiment 1 will be described referring to FIGS. 1 and 2.

FIG. 1 is an illustration of the disposed positions of individual constituent means in the case where individual constituent means of a behavior determining apparatus according to Embodiment 1 of the present invention are disposed at the respective positions of a residence. FIG. 2 is a block diagram of a behavior determining apparatus according to Embodiment 1 of the present invention.

As shown in FIG. 1, a behavior determining apparatus according to Embodiment 1 of the present invention comprises CCD cameras 1a and 1b, an IR sensor 2, an in-bed/out-of-bed sensor 3, an air-quality sensor 4, a toilet sensor 5, window Open/Close detective means 6 and 7, TV power source ON/OFF detective means 8, refrigerator door Open/Close detective means 9, management unit 10, a PIT 11, transmitter/receiver unit 12 and a loudspeaker 13.

The CCD camera la is means, installed on the ceiling of a kitchen 14 at the first floor of a residence, for photographing the space look of the kitchen 14, whereas the CCD camera 1b is means, installed on the ceiling of a living room 15 at the first floor, for photographing the space look of the living room 15. The IR sensor 2 is means, installed on the ceiling at the position of the door separating the kitchen 14 and the living room 15 from each other, for detecting the move of a human body from one to another of the kitchen 14 and the living room 15. The in-bed/out-of-bed sensor 3 is means, installed between the stay of a bed 17 disposed in a bedroom 16 of the second floor and the floor on which the bed 17 is placed, for detecting whether a person is present in the bed 17 by detecting the load weight imposed on the bed 17. The air-quality sensor 4 is means, installed on the ceiling of the kitchen 14, for measuring the humidity and the concentration of volatile organic substances and $CO_2$ in the kitchen room and the toilet sensor 5 is means, installed on the ceiling of a toilet 18, for detecting a rough position and time of a person entering the toilet 18 by using an IR long-range sensor.

The window Open/Close detective means 6 is means, installed on the window 19 provided in the bedroom 16, for detecting whether the window 19 is Open or Close. Similarly, the window Open/Close detective means 7 is means for detecting whether the window 20 provided in the living room 15 is Open or Close. The TV power supply ON/OFF detective means 8 is means for detecting whether the power supply of the TV set 21 provided in the living room 15 is ON or OFF wherein power supply ON/OFF of the TV set 21 is detected using a greater current quantity for ON than for OFF or discerning whether the TV set 21 caught a remote control switch signal or not. The refrigerator door Open/Close detective means 9 is means, installed on the refrigerator 22 provided in the kitchen 14, for detecting whether the door is Open or Close.

Figure 2:
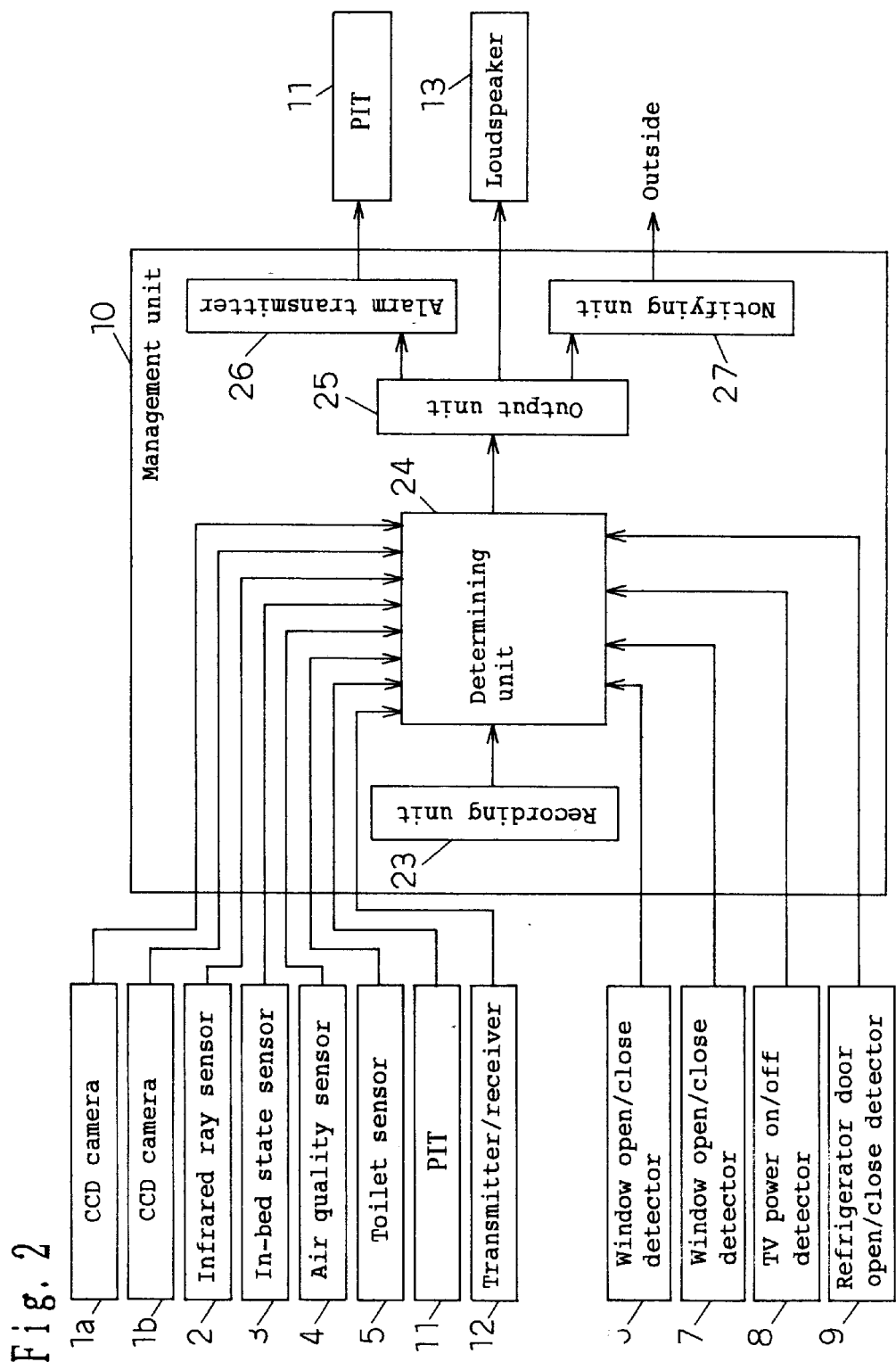
FIG. 2 is a block diagram of the behavior determining apparatus of embodiment 1 of the present invention.

The management unit 10, provided on the wall of the living room 15, comprises recording unit 23, determining unit 24, output unit 25, alarm transmitter unit 26 and notifying unit 27 as shown in FIG. 2.

The recording unit 23 is means for recording combined patterns of behavior of a resident in the residence of FIG. 1 and operation of appliances installed in the residence. The determining unit 24 is means for comparing the actual behavior of the resident and the actual operation of appliances with patterns recorded in the recording unit 23 to determine whether a combination of the actual behavior of the resident and the actual operation of appliances substantially accords with any patterns recorded in the recording unit 23 or not.

Meanwhile, in this embodiment, the actual behavior of a resident is detected by CCD cameras 1a and 1b, an IR sensor 2, an in-bed/out-of-bed sensor 3, an air-quality sensor 4, a toilet sensor 5 and a PIT 11 and the information received by transmitter/receiver unit 12 is also utilized for the behavior detection of the resident. Besides, the actual operation of appliances in this embodiment signifies the respective operations such as Open/Close of the windows 19 and 20 provided at the bed room 16 and the living room 15, power supply ON/OFF of the TV set 21 disposed in the living room 15 and door Open/Close of the refrigerator 22 disposed in the kitchen 14, each of which is detected by the window Open/Close detective means 6, the window Open/Close detective means 7, the TV power supply ON/OFF detective means 8 or the refrigerator door Open/Close detective means 9.

The output unit 25 is means for outputting the result determined by the determining unit 24. The alarm transmitter unit 26 is means for transmitting an alarm by a radio wave when it is determined by the determining unit 24 that a combination of actual behavior of the resident and actual operation of appliances does not substantially accord with any pattern recorded in the recording unit 23. When it is determined by the determining means 24 that a combination of actual behavior of the resident and actual operation of appliances does not substantially accord with any pattern recorded in the recording unit 23, the notifying unit 27 is means for outputting an alarm to a loudspeaker disposed in another residence than that of FIG. 1 and connected to the notifying unit 27 via a telephone line. Incidentally, the loud speaker emits an alarm sound if an alarm from the notifying unit 27 is inputted thereto Besides, the loudspeaker is not illustrated.

The PIT 11 is a personal information terminal borne by the resident of FIG. 1 and capable of transmitting/receiving an information item by a radio wave and incorporates means for transmitting that ID number peculiar to the bearing resident which specifies the relevant resident by a faint radio wave when receiving a given instruction from the transmitter/receiver unit 12 by a radio wave. Besides, the PIT 11 also incorporates means for receiving the alarm by a radio wave transmitted by the alarm transmitter unit 26 of the management unit 10 to emit a voice, vibration and flash based on the alarm and notify the alarm to the person bearing the PIT 11.

Besides, the PIT 11 has a gyro-sensor, acceleration sensor and angle sensor and is also means for detecting the posture such as standing posture, seated posture or lateral decubitus of its bearing person. Besides, the PIT 11 has a function for detecting the moving manner and the activity of its bearing person. Furthermore, the PIT 11 incorporates means capable of detecting the physiological state such as heart-rate or body temperature of its bearing person. Incidentally, the transmitting/receiving of an information item by means of the PIT 11 is also performed in the communication form of a PHS system or in a specific small power communication form using a frequency band of several hundred MHz. Besides, in FIG. 2, two PITs 11 are displayed, but since both of them are identical and their functions are multiple, two PITs 11 are represented for conveniences of description.

The transmitter/receiver unit 12 is means disposed adjacent to the IR sensor 2 on the ceiling positioned at the door separating the kitchen 14 and the living room 15 from each other, capable of transmitting/receiving an information item by a radio wave and also means for specifying a moving person in case of information input from the IR sensor 2 to the effect that the move of a person was detected.

The loudspeaker 13 is means for emitting an alarm sound when the determined result outputted by the output unit 25 of the management unit 10 is that a combination of actual behavior of the resident and operation of appliances does not substantially accord with any pattern recorded in the recording unit 23.

Meanwhile, in Embodiment 1, CCD cameras 1a and 1b, an IR sensor 2, an in-bed/out-of-bed sensor 3, an air-quality sensor 4, a toilet sensor 5, a PIT 11 and a transmitter/receiver unit 12 are used as one example of first detective means in a behavior determining apparatus according to the present invention as claimed in claim 1. Besides, window Open/Close detective means 6 and 7, TV power supply ON/OFF detective means 8 and refrigerator door Open/Close detective means 9 are used as one example of second detective means in a behavior determining apparatus according to the present invention as claimed in claim 1. Besides, recording unit 23, determining unit 24 and output unit 25 in the management unit 10 are respectively used as one example of recording means, determining means and output means in a behavior determining apparatus according to the present invention as claimed in claim 1.

Besides, in Embodiment 1, transmitter/receiver unit 12 is used as one example of first transmitter/receiver means in a behavior determining apparatus according to the present invention as claimed in claim 2 and second transmitter/receiver means is assumed to be provided in the PIT 11. Besides, alarm transmitter unit 26 in management unit 10 is used as one example of alarm transmitter means in a behavior determining apparatus according to the present invention as claimed in claim 3 and alarm receiver means is assumed to be provided in the PIT 11. Besides, a loudspeaker 13 is used as one example of informing means in a behavior determining apparatus according to the present invention as claimed in claim 4. Furthermore, notifying unit 27 in the management unit 10 is used as one example of notifying means in a behavior determining apparatus according to the present invention as claimed in claim 5.

Next, an operation of a behavior determining apparatus according to Embodiment 1 of the present invention will be described.

First, a resident allows the recording unit 23 of the management unit 10 to record the behavior of the subject resident, detected by CCD cameras 1a and 1b, an IR sensor 2, an in-bed/out-of-bed sensor 3, an air-quality sensor 4, a toilet sensor 5, a PIT 11 and transmitter/receiver unit 12. Besides, similarly when the behavior is recorded in the recording unit 23 of the management unit 10, the resident allows the recording unit 23 to record the respective operations of Open/Close of windows 19 and 20, power supply ON/OFF of a TV set 21 and door Open/Close of a refrigerator 22 detected by the window Open/Close detective means 6 and 7, the TV power supply ON/OFF detective means 8 and the refrigerator door Open/Close detective means 9.

Here, for conveniences of the following description, recording in the recording unit 23 the behavior of the resident on the above subject and the respective operations of Open/Close of windows 19 and 20, power supply ON/OFF of a TV set 21 and door Open/Close of a refrigerator 22 is assumed to have continued for a period of one year in 1998. And, combinations of the behavior of a resident and the respective operations of Open/Close of windows 19 and 20, power supply ON/OFF of a TV set 21 and door Open/Close of a refrigerator 22 recorded in the recording unit 23 are assumed to be averaged for each month and anew recorded as patterns regarding the behavior of the resident on the subject into the recording unit 23.

Figure 3:
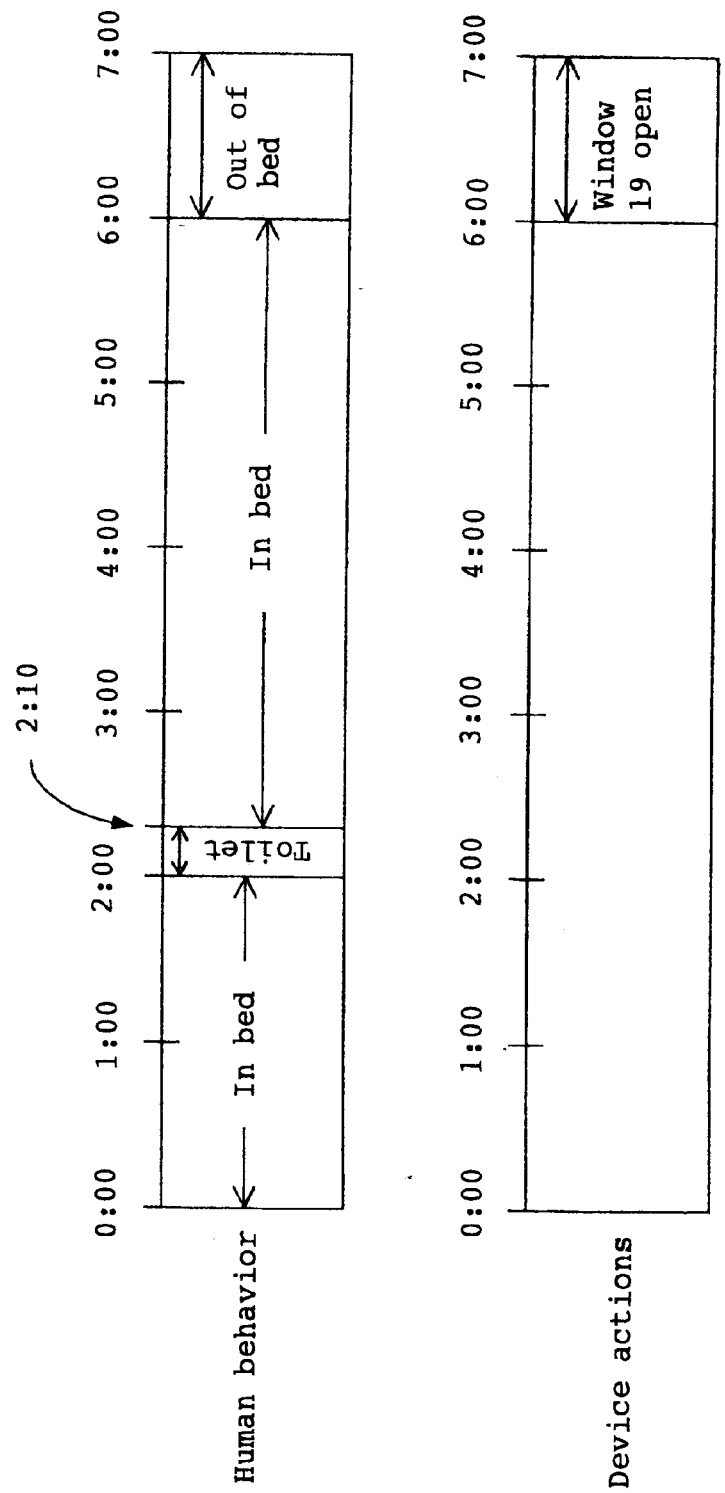
FIG. 3 is a drawing showing part of pattern 1 recorded in recording unit 23 of the behavior determining apparatus of embodiment 1 of the present invention.
Figure 4:
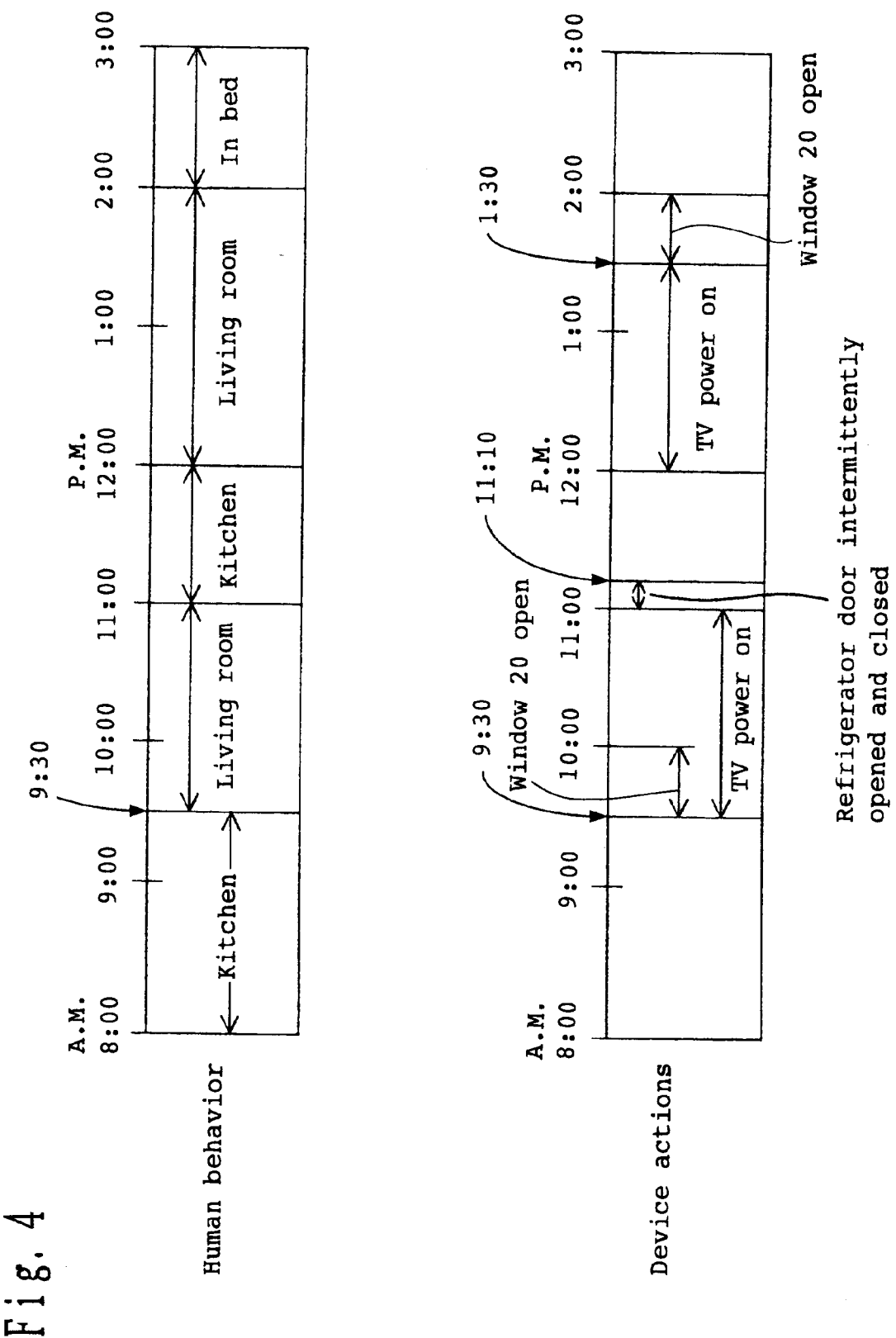
FIG. 4 is a drawing showing part of pattern 2 recorded in the recording unit 23 of the behavior determining apparatus of embodiment 1 of the present invention.

Thus, in this embodiment, the recording unit 23 ends in having recorded the averaged pattern regarding behavior of the resident on the subject for each month of 1998. Here, letting the pattern on July of 1998 and that on August of 1998 recorded in the recording unit 23 be first and second patterns, respectively, the portion of 0:00 to 7:00 a.m. out of the first pattern and the portion of 8:00 a.m. to 3:00 p.m. out of the second pattern are shown in FIGS. 3 and 4, respectively.

First, part of the first pattern will be described. As shown in FIG. 3, it was detected as the first pattern by the in-bed/out-of-bed sensor 3 for detecting the load weight applied to the bed 17 and is recorded in the recording unit 23 that the resident was in the bed 17 from 0:00 to 2:00 a.m. Thereafter, the load weight applied to the bed 17 became undetectable from 2:00 to 2:10 a.m. for the in-bed/out-of-bed sensor 3, it was detected by the toilet sensor 5 for measuring the rough position of a human body in the toilet 18 and is recorded in the recording unit 23 that the resident was in the toilet 18. Then, it was detected by the in-bed/out-of-bed sensor 3 and is recorded in the recording unit 23 respectively that the resident was in the bed 17 from 2:10 to 6:00 a.m. and that the resident was out of the bed 17 from 6:00 to 7:00 a.m.

Besides, it was detected from 0:00 to 7:00 a.m., by the window Open/Close detective means 7, by the TV power supply ON/OFF detective means 8 and by the refrigerator door Open/Close detective means 9 respectively and is recorded as part of the first pattern in the recording unit 23 that the window 20 was Close, that the power supply of the TV set 21 was OFF and that the door of the refrigerator 22 was Close. Besides, it was detected by the window Open/Close detective means 6 and is recorded as part of the first pattern in the recording unit 23 that the window 19 was Close from 0:00 to 6:00 a.m. and Open from 6:00 to 7:00 a.m. Meanwhile, with respect to the operation of a first-pattern appliance, FIG. 3 demonstrates that the window 19 was Open from 6:00 to 7:00 a.m. Besides, as mentioned above, the first pattern is a pattern averaged over July of 1998.

Next, the second pattern will be described. From the result obtained from 8:00 to 9:30 a.m. as the second pattern that the figure of the resident is contained in the picture of the kitchen 14, photographed by the CCD camera 1a and the $CO_2$ concentration in the kitchen 14 measured by the air-quality sensor 4 exceeded a given threshold, it was detected as shown in FIG. 4 and is recorded in the recording unit 23 that the resident was in the kitchen 14. Incidentally, since the $CO_2$ concentration in the kitchen 14 rises if a person is present in the kitchen 14, measuring the $CO_2$ concentration in the kitchen 14 by the air-quality sensor 4 makes it possible to detect whether a person is present in the kitchen 14 or not. Besides, when a person has cooked in the kitchen 14, the humidity, the $CO_2$ concentration and the volatile organic component concentration increases, so that the entire or partial measurement of the humidity, the $CO_2$ concentration and the volatile organic component concentration in the kitchen 14 by the air-quality sensor 4 also makes it possible to detect whether a person is present in the kitchen 14 or not.

And, at 9:30 a.m., the IR sensor 2 detected the move of a person, the figure of the resident disappeared from the picture of the kitchen 14, photographed by the CCD camera 1a, the $CO_2$ concentration in the kitchen 14 measured by the air-quality sensor 4 fell short of a given threshold, and further the figure of the resident was contained in the picture of the living room 15, photographed by the CCD camera 1b. As a result, it was detected and is recorded in the recording unit 23 that the resident left the kitchen 14 and entered the living room 15. Thereafter, since the figure of the resident remained contained from 9:30 to 11:00 a.m. in the picture of the living room 15, photographed by the CCD camera 1b, it was detected and is recorded in the recording unit 23 that the resident was in the living room 15.

And, at 11:00 a.m., the IR sensor 2 detected the move of a person again, the figure of the resident was contained in the picture of the kitchen 14, photographed by the CCD camera 1a and further the humidity, the $CO_2$ concentration and the volatile organic component concentration in the kitchen 14 measured by the air-quality sensor 4 exceeded given thresholds, with the result that it was detected and is recorded in the recording unit 23 that the resident was in the kitchen 14. And, from a third detection of IR reflection by the IR sensor 2 and such others at 0:00 p.m., it is recorded in the recording unit 23 that the resident left the kitchen 14 and entered the living room 15. Thereafter, from 2:00 to 3:00 p.m., since the load weight applied to the bed 17 was detected by the in-bed/out-of-bed sensor 3, it was detected and is recorded in the recording unit 23 that the resident was in the bed 17.

Besides, the window Open/Close detective means 6 detected that the window 19 was Close from 8:00 a.m. to 3:00 p.m. and the window Open/Close detective means 7 detected that the window 20 was Open from 9:30 to 10:00 a.m. and from 1:30 to 2:00 p.m. and Close in the other time zones, which fact is recorded as part of the second pattern in the recording unit 23.

Besides, it was detected by the TV power supply ON/OFF detective means 8 and is recorded also in the recording unit 23 that the power supply of a TV set 21 was ON from 9:30 to 11:00 a.m. and from 0:00 to 1:30 p.m. and OFF in the other time zones. Furthermore, it was detected by the refrigerator door Open/Close detective means 9 and is recorded as part of the second pattern in the recording unit 23 that the door of the refrigerator 22 discontinuously repeated the opening and closing from 11:00 to 11:10 a.m. and was Close in the other time zones. Incidentally, as mentioned above, the second pattern is an averaged pattern over August of 1998.

Meanwhile, when a resident moves from the kitchen 14 to the living room 15 or from the living room 15 to the kitchen 14, the IR sensor 2 detects the move of a person and in this case, the IR sensor 2 outputs the information about the detection of a person's move to the transmitter/receiver unit 12. Then, the transmitter/receiver unit 12 transmits such an instruction to the PIT 11 as to dispatch the ID number for specifying the bearer of the PIT 11 by a radio wave having a high directivity in a limited space. Having received the instruction, the PIT 11 dispatches the ID number for specifying the bearing resident by a radio wave and the transmitter/receiver unit 12 specifies the person issuing the IR rays detected by the IR sensor 2 on the basis of the ID number from the PIT 11. In accordance with this specification, it is specified who is the resident having moved from the kitchen 14 to the living room 15 or from the living room 15 to the kitchen 14.

If a plurality of persons live in one residence, such an specification method can be used in case of specifying who is the person having moved from one of the adjoining rooms to the other and in case of specifying who is the person having moved from one to the other between the adjoining room and the corridor. Incidentally, to specify who is the person having moved from one to the other between the adjoining room and the corridor, means capable of specifying who is the person having moved from one to the other between a room and the corridor on the basis of the ID number from the PIT 11 as with the above transmitter/receiver unit 12 has to be installed, for example, on the ceiling of the adjoining part between the room and the corridor.

Next, the operation of a behavior determining apparatus according to Embodiment 1 of the present invention after a first pattern and a second pattern are recorded in the recording unit 23 will be described. For conveniences of description, the operation on Jul. 22 and Aug. 3, 1999 of a behavior determining apparatus according to Embodiment 1 of the present invention will be described.

The behavior of a resident on Jul. 22 and Aug. 3, 1999 is detected by means of CCD cameras 1a and 1b, an IR sensor 2, an in-bed/out-of-bed sensor 3, an air-quality sensor 4, a toilet sensor 5 and a PIT 11 for either day and the respective detected data are inputted to the determining unit 24 shown in FIG. 2. Besides, the information of the bearer of the PIT 11, specified by the transmitter/receiver unit 12, is also inputted to the determining unit 24. Besides, the Open/Close operation of the windows 19 and 20, the power supply ON/OFF operation of the TV set 21 and the door Open/Close operation of the refrigerator 22 for either of July 22 or August 3 are detected by the window Open/Close detective means 6 and 7, the TV power supply ON/OFF detective means 8 and refrigerator door Open/Close detective means 9, respectively and the respective detected data are inputted to the determining unit 24.

Figure 5:
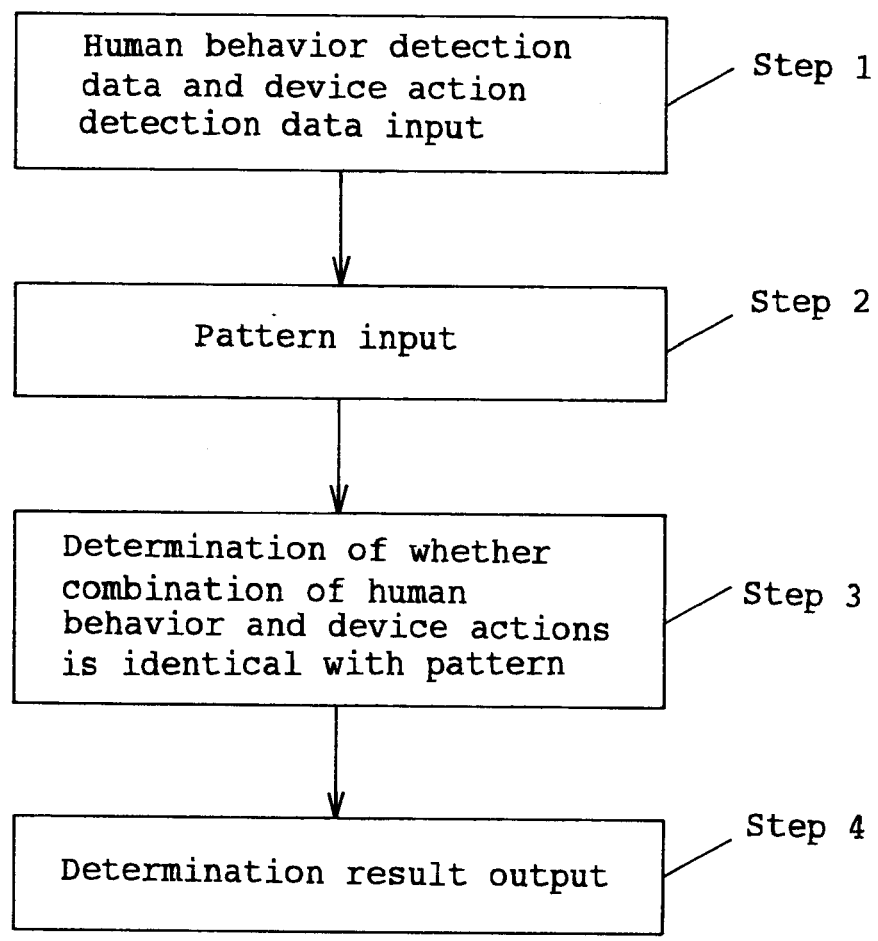
FIG. 5 is a flowchart showing the operation of the determining unit 24 of the behavior determining apparatus of embodiment 1 of the present invention.

Next, the operation of the determining unit 24 will be described referring to the flowchart of FIG. 5. The determining unit 24 inputs not only the respective detected data mentioned above (step 1) but also the first and second patterns recorded in the recording unit 23 (step 2) and determines whether a combination of behavior of the resident and each of the operations of Open/Close of the windows 19 and 20, power supply ON/OFF of the TV set 21 and door Open/Close of the refrigerator 22 accords with the first pattern or the second pattern in a given period of time or within a given behavior range (step 3) and outputs the determined result to the output unit 25 (step 4).

A description will be made to cite a specific example. On July 22, for example, assuming that a resident is in the bed 17 from 0:00 to 1:55 a.m., leaves the bed 17 and goes to the toilet 18 at 1:55 a.m. and returns to the bed 17 at 2:05 a.m., the behavior of the resident in this case is detected by means of the in-bed/out-of-bed sensor 3 and the toilet sensor 5 and inputted to the determining unit 24. Meanwhile, since the behavior of the resident inputted to the determining unit 24 shifts from the behavior from 0:00 to 2:10 a.m. of the first pattern described referring to FIG. 3 only by 5 min, the determining unit 24 determines that the actual behavior of the resident substantially accords with the behavior of a resident in the first pattern. Here, in a period of time ranging from 0:00 to 1:55 a.m. of July 22, if the window Open/Close detective means 6, the window Open/Close detective means 7, the TV power supply ON/OFF detective means 8 and the refrigerator door Open/Close detective means 9 are assumed to respectively detect that the window 19 was Close, the window 20 was Close, the power supply of the TV set 21 was OFF and the door of the refrigerator 22 was Close, the determining unit 24 determines that a combination of the behavior of the resident and each of the operations of Open/Close of the windows 19 and 20, power supply ON/OFF of the TV set 21 and door Open/Close of the refrigerator 22 substantially accords with the first pattern and outputs the determined result to the output unit 25. The output unit 25 outputs the determined result to the alarm transmitter unit 26 and the notifying unit 27. Since it was determined that a combination of the behavior of the resident and each of the operations of the windows 19 and 20, the TV set 21 and the door of the refrigerator 22 substantially accords with the first pattern, the alarm transmitter unit 26 and the notifying unit 27 output no alarm.

Next, a description will be made to cite another specific example. For example, a case where a resident left the bed 17 and did not open the window 19 at 6:00 a.m. on July 22 will be described. And, it is assumed that the window 19 was not opened later. The resident behavior in that case is detected by means of the in-bed/out-of-bed sensor 3 and inputted to the determining unit 24. Besides, the Open/Close operation of the window 19 is detected by means of window Open/Close detective means 6 and inputted to the determining unit 24. The resident behavior inputted to the determining unit 24 accords with that subsequent to 6:00 a.m. in the first pattern, but the window 19 is not Open and accordingly the actual Open/Close operation of the window 19 does not accord with the Open/Close operation of the window 19 in the first pattern. As a result, the determining unit 24 determines that a combination of behavior of the resident and Open/Close operation of the window 19 does not substantially accord with the first pattern.

And, the determining unit 24 outputs the determined result that a combination of behavior of the resident and Open/Close operation of the window 19 does not substantially accord with the first pattern to the output unit 25. Then, the output unit 25 outputs the determined result to the alarm transmitter unit 26 and the notifying unit 27 and simultaneously to the loudspeaker 13. The alarm transmitter unit 26 transmits an alarm by a radio wave, while the PIT 11 receives the alarm by the radio wave and emits a voice, vibration and flash based on the alarm to notify an alarm to the bearer. Besides, the notifying unit 27 is disposed in another than the residence of FIG. 1 and outputs an alarm to a loudspeaker connected to the notifying unit 27 via a telephone line, thus forcing the emission of an alarm sound. Besides, based on the determined result from the output unit 25, the loudspeaker 13 emits an alarm sound.

Since the PIT 11 and the loudspeaker 13 emit an alarm like this, the resident himself can perceive that the pattern pre-recorded in the recording unit 23 differs from the actual behavior and moreover other residents than the relevant person can also perceive that abnormalities might occur on the behavior of the resident on the subject of judgement for the determining unit 24. Besides, based on the alarm from the notifying unit 27, residents in another than the residence of FIG. 1 also can perceive that abnormalities might occur regarding behavior of the resident on the subject of judgement for the determining unit 24. Thus, if notifying unit 27 and a loudspeaker for emitting an alarm sound in accordance with the alarm outputted from the notifying unit 27 are disposed in a 2-generation residence, abnormalities occurring in an elderly person, for example, usually living alone for the most part of a day, can be rapidly known to his or her son or daughter.

Also in former days, resident's leaving the bed 17 and the Open/Close operation of a window 19 was individually detected, but it was not determined whether a combination of the behavior of a resident and the accompanying operation of the window 19 did not substantially accord with a given pattern, so that the behavior of the subject resident after leaving the bed 17 was not specified more accurately. In contrast, with this embodiment, since it is determined whether a combination of the behavior of a resident and the accompanying operation of the-window 19 substantially accords with a given pattern, the behavior of the subject resident after leaving the bed 17 is specified more accurately. Thus, in the case where a resident left the bed 17 at 6:00 a.m., fell down on account of abnormalities having occurred at this time in his or her body and consequently could not open the window 19, for example, the loudspeaker 13 emits an alarm sound, so that other residents can rapidly take the corresponding measures on occurrence of abnormalities in the body of the resident on the subject of judgement for the judging unit 24. Besides, in response to the alarm from the notifying unit 27, residents in other residences than that of FIG. 1 can also take similar measures rapidly.

Meanwhile, as shown in FIG. 3, the first pattern recorded in the recording unit 23 describes only the fact of "having left the bed 17," detected by the in-bed/out-of-bed sensor 3, as the behavior of a person from 6:00 to 7:00, but instead or additionally, data on the posture of a subject resident, detected the gyro-sensor, acceleration sensor and angle sensor incorporated in the PIT 11, may be described. In that case, the determining unit 24 will determine whether a combination of the behavior detected of a resident at least by means of the PIT 11 and operation of appliances such as window 19 substantially accords with a pattern including at least data on the posture of the resident or not.

Thus, in determining case of the determining unit 24 when the data telling that a resident fell down after leaving the bed 17 is not described, for example, as the behavior of a person from 6:00 to 7:00 in part of the first pattern recorded in the recording unit 23, a resident is assumed to fall down after leaving the bed 17 and the fact of falling down is detected by the PIT 11, so that the determining unit 24 determines that the behavior of the resident does not accord with the pattern, thus resulting in the emission of an alarm.

Furthermore, a description will be made to cite yet another specific example. On August 3, when a resident entered the kitchen 14 at 11:00 p.m. and opened the door of a refrigerator 22 in attempt to begin the preparation of a lunch, it is assumed that abnormalities occurred in his body and he fell down. His behavior in that case is detected by means of the CCD camera 1a and the air-quality sensor 4 and inputted to the determining unit 24. Besides, the door Open/Close operation of the refrigerator 22 is detected by the refrigerator door Open/Close detective means 9 and inputted to the determining unit 24. The behavior of the resident inputted to the determining unit 24 substantially accords with that subsequent to 11:00 p.m. in the second pattern described referring to FIG. 4, but the door of the refrigerator 22 remains opened and accordingly the actual door Open/Close operation of the refrigerator 22 does not accord with the door Open/Close operation in the second pattern. As a result, the determining unit 24 determines that a combination of the behavior of the resident and the door Open/Close operation of the refrigerator 22 does not substantially accord with the second pattern.

Then, the determining unit 24 outputs the determined result that a combination of the behavior of the resident and the door Open/Close operation of the refrigerator 22 does not substantially accord with the second pattern to the output unit 25. The output unit 25 outputs the determined result to the alarm transmitter unit 26 and the notifying unit 27 and simultaneously to the loudspeaker 13. The alarm transmitter unit 26 transmits an alarm by a radio wave, while the PIT 11 receives the alarm by the radio wave and emits a voice, vibration and flash based on the alarm to notify an alarm to the bearer. Besides, the notifying unit 27 outputs an alarm to a loudspeaker connected to the notifying unit 27 via a telephone line, thus forcing the emission of an alarm sound. The loudspeaker is disposed in another than the residence of FIG. 1. Besides, based on the determined result from the output unit 25, the loudspeaker 13 emits an alarm sound.

Since the PIT 11 and the loudspeaker 13 emit an alarm like this, other residents can perceive that abnormalities might occur on the behavior of the resident in the subject of judgement for the determining unit 24. Besides, based on the alarm from the notifying unit 27, residents in another than the residence of FIG. 1 also can perceive that abnormalities might occur regarding behavior of the resident on the subject of judgement for the determining unit 24.

Meanwhile, as shown in FIG. 4, the second pattern recorded in the recording unit 23 describes only the fact of "being present in the kitchen 14," detected by the CCD camera 1a or the air-quality sensor 4, as the behavior of a person from 11:00 to 12:00, but instead or additionally, data on the posture of a subject resident, detected by the gyro-sensor, acceleration sensor and angle sensor incorporated in the PIT 11, may be described. In that case, the determining unit 24 will determine whether a combination of the behavior of a resident detected at least by means of the PIT 11 and the operation of an appliance such as door operation of a refrigerator 22 substantially accords with a pattern including at least data on the posture of the resident or not. Thus, in determining case of the determining unit 24 when the data telling that a resident fell down is not described, for example, as the behavior of the subject from 11:00 to 12:00 in part of the second pattern recorded in the recording unit 23, a resident is assumed to fall down in the kitchen 14 and the fact of falling down is detected by the PIT 11, so that the determining unit 24 determines that the behavior of the resident does not accord with the pattern, thus resulting in the issue of an alarm.

As described above, a behavior determining apparatus according to Embodiment 1 of the present invention can determine whether the combined pattern of behavior of a given subject person and a given appliance, pre-recorded in the recording unit 23, substantially accords with a combination of the behavior of the actual subject person and the operation of the actual appliance and outputs the determined result, so that abnormalities in the behavior of the subject person is inferred more accurately and more rapidly. Besides, the subject person himself can also perceive that he has behaved differently from the pattern.

Meanwhile, in Embodiment 1, a case where individual constituent means of a behavior determining apparatus are disposed at the respective positions of a residence was described, but individual constituent means of a behavior determining apparatus are not restricted to be disposed only at the respective positions of a residence but may be disposed at a hospital, a protective institution or the like, for example. In that case, when the output unit 25 or the notifying unit 27 outputs the determined result to the management station such as nursing station of a hospital directly or via other appliances, the management staff such as nurses can grasp the behavior of subject persons more accurately.

Besides, many subject persons are present in a hospital, a protective institution or the like, while if each subject person is allowed to bear transmitter means for transmitting an ID number peculiar to the bearing resident for specifying him by a radio wave, similar to the second transmitter/receiver means provided in the above PIT 11, or to bear the above PIT 11, it is specified who is the person detected by detective means such as an IR sensor for detecting the personal behavior. Incidentally, in the case where the subject lives alone and individual constituent means of a behavior determining apparatus are installed at his residence, for example, there is only a single subject person in the residence and accordingly it is unnecessary for the PIT 11 to have means for specifying its bearer provided. Besides, in this case, the determined result determined by the determining unit 24 is outputted to the managing center for nursing subject persons of a public welfare institution or the like outside the residence via the output unit 25 or via the output unit 25 and the notifying unit 27 and the behavior of subject persons are managed by a public welfare institution or the like.

Besides, in Embodiment 1, it was not mentioned who is the subject for the judgement of a behavior determining apparatus, but in case of a senile dementia as subject, the behavior determining apparatus issues an alarm if the using manner of water in the toilet unit differs from the pattern recorded in the recording unit 23, for example, even when the period of time while the subject is in the toilet 18 is identical to the period of time of the pattern recorded in the recording unit 23. Thus, other residents can perceive such an abnormal behavior that an elderly person has played in the toilet 18 or has washed something in a stool. Besides, when an elderly person has forgotten to extinguish the fire of a gas range after the cooking in the kitchen 14, for example, other residents can perceive that abnormalities occurred in the elderly person because the behavior determining apparatus issues an alarm if a combination of his behavior detected by means of the CCD camera 1a or the like and the operation of a gas range does not substantially accord with the pattern recorded in the recording unit 23.

Besides, when an elderly person got up at midnight, walked round in a house and wandered about, for example, other residents can also perceive that abnormalities occurred in the elderly person because the behavior determining apparatus issues an alarm if a combination of his or her behavior and operation of appliances in the house does not substantially accord with the pattern recorded in the recording unit 23. Thus, even if an elderly person actually went to the toilet 18 or the kitchen 14 at the time when he was scheduled to leave the bed 17 and go to the toilet 18 or the kitchen 14 according to the pattern recorded in the recording unit 23, other residents can also perceive that abnormalities occurred in the elderly person if neither the refrigerator 22 nor the toilet unit was used though the refrigerator 22 or the toilet unit is scheduled to be used in the pattern.

Besides, in case of a hypertension middle-aged or elderly person as subject, for example, when the person fell down in the kitchen 14, the position of the middle-aged or elderly person is detected by means of the CCD camera 1a, the activity or posture is detected by means of a gyro-sensor, an acceleration sensor and an angle sensor incorporated in the PIT 11 and the operation of equipped appliances in the kitchen 14 is also detected. Other residents can perceive that abnormalities occurred in the middle-aged or elderly person because the behavior determining apparatus issues an alarm if a combination of his or her behavior detected and the operation of equipped appliances does not substantially accord with the pattern recorded in the recording unit 23.

Besides, in Embodiment 1, CCD cameras 1a and 1b, an IR sensor 2, an in-bed/out-of-bed sensor 3, an air-quality sensor 4, a toilet sensor 5, a PIT 11 and transmitter/receiver unit 12 were used as one example of first detective means in a behavior determining apparatus according to the present invention as claimed in claim 1, but the first detective means is not limited to the CCD camera 1 or IR sensor 2. If only capable of detecting the behavior of a subject, any is available for first detective means. Besides, as the behavior of a subject, the posture, the moving manner and the activity are also included. All of them are detected by means of a PIT 11.

Besides, in Embodiment 1, the PIT 11 was assumed to transmit an ID number for specifying its bearer by a radio wave when receiving a given instruction from the transmitter/receiver unit 12, but transmitter means such as PIT 11 may be assumed to regularly or irregularly transmit an ID number for specifying individual residents by a radio wave regardless of whether it has received a given instruction from the transmitter/receiver unit 12.

Besides, in Embodiment 1, the transmitter/receiver unit 12 was assumed to specify the bearer of the PIT 11, but all or part of the CCD cameras 1a and 1b, the IR sensor 2, the in-bed/out-of-bed sensor 3, the air-quality sensor 4 and the toilet sensor 5 are assumed to have a function for specifying the bearer of the PIT 11 and specify the bearer of the PIT 11 by using the ID number by the radio wave from the PIT 11.

Besides, in Embodiment 1, window Open/Close detective means 6 and 7, TV power supply ON/OFF detective means 8 and refrigerator door Open/Close detective means 9 were used as one example of second detective means in a behavior determining apparatus according to the present invention as claimed in claim 1, but the second detective means is not limited to the window Open/Close detective means 6 or the TV power supply ON/OFF detective means 8 mentioned above. The second detective means has only to be any of those which detect the operation of a given appliance.

Besides, in Embodiment 1, the recording unit 23 was assumed to have recorded first and second patterns, but the recording unit 23 has only to have recorded one or more of the combined patterns of behavior of a subject person and operation of appliances. Thus, the recording unit 23 is not restricted in having recorded the averaged pattern for each month during one year of 1998 mentioned above, but may have recorded the detected data of only one day as a pattern, or the averaged data over one month or the data averaged for each weekday of the one-month detected data as patterns. In brief, the recording unit 23 has only to have recorded one or more of combinations of behavior of a subject person and operation of appliances. Besides, the determining unit 24 has only to compare one or more patterns recorded in the recording unit 23 with the actual behavior of a subject person and the actual operation of appliances and determine whether a combination of the actual behavior of a subject person and the actual operation of appliances substantially accords with any of the patterns recorded in the recording unit 23. Incidentally, the above expression of "substantially accord" signifies either a case where a combination of behavior of a subject person and operation of appliances accords with a pattern within a given time range, for example, within 10 min or a case where, for example, two different behavioral ways of a subject person comprising standing in the kitchen 14 and squatting in the kitchen 14 are identical in that the subject person is present in the kitchen 14 and accordingly a combination of behavior of a subject person and operation of appliances accords with any pattern within a given behavior range of the subject person and/or within a given operation range of appliances.

Besides, in Embodiment 1, the loudspeaker 13 was assumed to issue an alarm sound in the case where a judgement that a combination of behavior of a subject person and operation of door Open/Close of the refrigerator 22 does not substantially accord with either the first pattern or the second pattern was made by the determining unit 24, but an alarm lamp for indicating an alarm by an optical signal may be used in place of the loudspeaker 13. In brief, an alarm has only to be outputted in the case where a judgement that a combination of behavior of a subject person and operation of appliances does not substantially accord with either the first pattern or the second pattern recorded in the recording unit 23 was made by the determining unit 24.

Besides, in Embodiment 1, the notifying unit 27 was assumed to output an alarm to the loudspeaker connected via a telephone line to the notifying unit 27 and cause the loudspeaker to issue an alarm sound, but an alarm lamp for indicating an alarm by a light signal may be used in place of the loudspeaker connected via a telephone line to the notifying unit 27. Besides, rather than connected via a telephone line, the notifying unit 27 may be assumed to be connected via an electric light line or an exclusive line to a loudspeaker or an alarm lamp disposed in another than the residence of FIG. 1. Anyhow, in the case where made by the determining unit 24 is a determining that a combination of behavior of a subject person and operation of appliances does not substantially accord with any of the patterns recorded in the recording unit 23, the notifying unit 27 has only to output an alarm to a connected loudspeaker or alarm light.

Besides, in Embodiment 1, the determining unit 24 was assumed to determine whether a combination of behavior of a subject person and operation of appliances accords with any of the patterns recorded in the recording unit 23, but the determining unit 24 may be assumed to determine whether a combination of behavior of a subject person, operation of appliances and physiological and/or psychological state of the subject person substantially accord with any of the patterns recorded in the recording unit 23. In that case, the patterns recorded in the recording unit 23 must be combined patterns of behavior of a subject person, operation of appliances and physiological and/or psychological state of the subject person. Furthermore, third detective means must be provided for detecting physiological and/or psychological state of the subject person.

Usable as means for detecting the physiological state of one subject person for the third detective means are, for example, a clinical thermometer for measuring the body temperature of a subject person, a sweating meter for measuring the sweating quantity of a subject person or a pulsimeter for measuring the heart rate of a subject person. Since the PIT 11 incorporates a function capable of detecting the physiological state such as heart-rate or body temperature of a bearer as mentioned above, it is only necessary to allow the PIT 11 to transmit physiological information items such as heart-rate or body temperature of a subject person regularly or irregularly by a radio wave and to allow the transmitter/receiver unit 12 to receive the radio wave. And, the physiological information items are inputted to the determining unit 24. Incidentally, they may be inputted to the determining unit 24 directly by a subject himself or his or her caretaker. Besides, usable as means for detecting the psychological state of the other subject person for the third detective means are, for example, all or part of the clinical thermometer, the sweating meter and the pulsimeter mentioned above and an instrument for evaluating a change in psychological state from a change in body temperature, sweating quantity or heart rate.

Like this, individual detective means are made to detect the behavior of a subject person, the operation of appliances and the physiological state of a subject person and/or the psychological state of a subject person and combinations of behavior of a subject person, operation of appliances and physiological state of a subject person and/or psychological state of a subject person are pre-recorded as patterns in the recording unit 23. And, the determining unit 24 is may be allowed to determine whether a combination of behavior of a subject person, operation of appliances and physiological state of a subject person and/or psychological state of a subject person substantially accords with any pattern or not. As a result, a case of comparing a combination of behavior of a subject person, operation of appliances and physiological state of a subject person and/or psychological state of a subject person with any pattern is more accurately determined on whether the behavior of a subject person substantially accords with any pattern than a case of comparing a combination of behavior of a subject person and operation of appliances with any pattern.

Besides, in the case where made by the determining unit 24 is a judgement that a combination of behavior of a subject person, operation of appliances and physiological state of a subject person and/or psychological state of a subject person does not substantially accord with any of the patterns recorded in the recording unit 23, the output unit 25 outputs an alarm to informing means such as loudspeaker 13 or alarm lamp and makes the alarm notified by means of a voice or an optical signal. Besides, similarly in the case where the judgement made by the determining unit 24 is NO, the alarm transmitter unit 26 transmits an alarm by a radio wave, while the PIT 11 is made to receive the alarm and to generate a voice, vibration and light based on the alarm, so that the bearer is notified of the alarm. Furthermore, similarly in the case where the judgement made by the determining unit 24 is NO, the notifying unit 27 outputs an alarm to a loudspeaker and an alarm lamp connected thereto via a telephone line, an electric light line or an exclusive line, thereby notifying the alarm.

Thus, in the case where an information item about body temperature or heart rate-of a resident in the bed 17 is pre-recorded as a pattern in the recording unit 23 together with the information that a resident is in the bed 17 and the information item about operation of appliances, for example, the determining unit 24 determines that the physiological state does not accord with the pattern on the basis of the body temperature and heart-rate rate of a subject person detected by the third detective means such as PIT 11 and issues an alarm correspondingly if the resident is in the bed 17 and the operation of appliances is substantially the same as the recorded pattern but the body temperature and the heart rate of the resident in the bed 17 are higher than those of the pattern in determining by the determining unit 24. As a result, it is more accurately inferable that abnormalities such as catching cold has occurred in the body of a resident.

Incidentally, as with the first detective means, the third detective means may be provided with a function of specifying a subject person by use of the information item through a radio wave and a function capable of detecting the physiological state and/or the psychological state of the person. Besides, as mentioned above, the PIT 11 can be used as one example of third detective means.

Besides, in the health care for a subject person, the determined result of the above behavior determining apparatus may be used by the subject himself or by the caretaker of the subject person.

Besides, individual constituents of a behavior determining apparatus according to Embodiment 1 entirely or partially belong to hardware or software having the same function as the relevant hardware.

Besides, medium bearing a program and/or data for allowing the functions of all or part of the constituents of the above behavior determining apparatus to be entirely or partially executed by a computer which can be processed by the computer also belongs to the present invention.

In media according to the present invention, recording medium such as ROM, transmittal medium such as internet and transmittal medium such as light, radio wave and sound wave are included. Examples of bearing media include recording media with a program and/or data recorded and transmission media for transmitting a program and/or data.

Thus, recording media with a program and/or data recorded for allowing the functions of all or part of the constituents of the above behavior determining apparatus to be entirely or partially executed by a computer which can be read by the computer so that the above program read and/or the above data read execute the above function in cooperation with the above computer also belong to the present invention.

Meanwhile, processible by a computer means, for example, readable by a computer in case of a recording medium such as ROM or processible by a computer as a result of transmitting a program and/or data to be transmitted in case of transmission media.

Furthermore, an information aggregate comprising programs and/or data for allowing the functions of all or part of the constituents of the above behavior determining apparatus to be entirely or partially executed by a computer also belongs to the present invention.

The information aggregate includes software such as program and/or data.

Incidentally, data in the media and information aggregate mentioned above include a data structure, a data format and a data type.

(Embodiment 2)

Next, a configuration of a care system according to embodiment 2 of the present invention will be described using FIGS. 1 and 6.

FIG. 1 is a drawing for explaining the location of each component unit when the several component units configuring the behavior determining apparatus of the above described embodiment 1 are installed in various locations in a residence, etc. As explained later, some of the component units configuring the care system of this embodiment 2 are the same as some of the component units configuring the behavior determining apparatus of embodiment 1, and therefore FIG. 1 will also be used when describing the care system of embodiment 2. FIG. 6 is a block diagram of the care system of embodiment 2 of the present invention.

Figure 6:
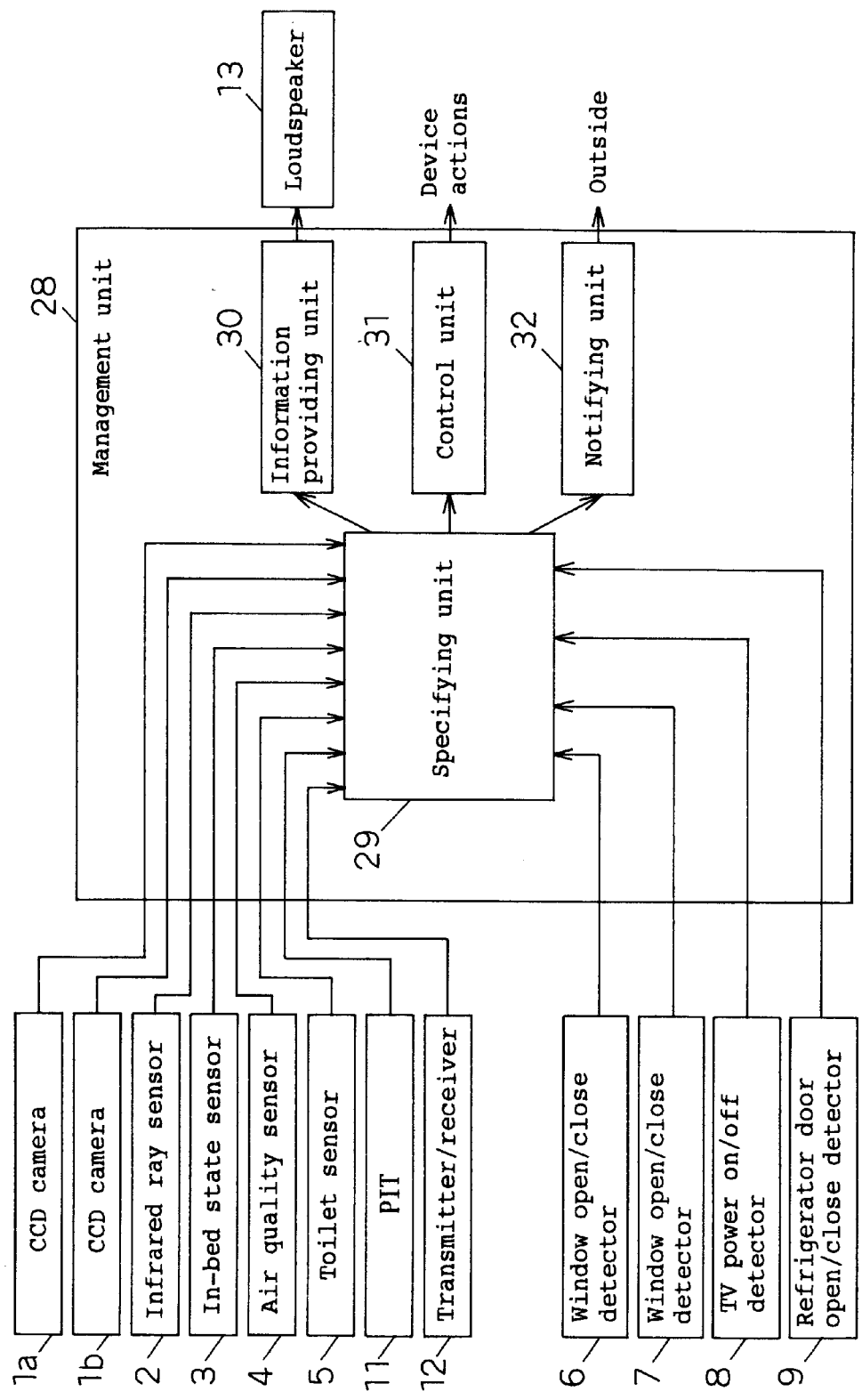
FIG. 6 is a block diagram of the care system of embodiment 2 of the present invention.

As shown in FIG. 6, the care system of embodiment 2 of the present invention is configured by CCD cameras 1a and 1b, an infrared ray sensor 2, an in-bed state sensor 3, an air quality sensor 4, a toilet sensor 5, window open/close detectors 6 and 7, a TV power on/off detector 8, a refrigerator door open/close detector 9, a management unit 28, a PIT 11, a transmitter/receiver 12, and a loudspeaker 13. The CCD cameras 1a and 1b, infrared ray sensor 2, in-bed state sensor 3, air quality sensor 4, toilet sensor 5, window open/close detectors 6 and 7, TV power on/off detector 8, refrigerator door open/close detector 9, PIT 11, transmitter/receiver 12, and loudspeaker 13 are the same as the relevant component units configuring the behavior determining apparatus of embodiment 1 described using FIGS. 1 and 2.

The management unit 28 is installed within a wall of the living room 15 in FIG. 1, in the same way as the management unit 10 of the behavior determining apparatus of embodiment 1, and, as shown in FIG. 6, is configured by an specifying unit 29, an information providing unit 30, a control unit 31, and a notifying unit 32.

The specifying unit 29 is means for accurately specifying the behavior of the resident from detected resident behavior and detected device actions. The behavior of the resident is detected by means of the CCD cameras 1a and 1b, infrared ray sensor 2, in-bed state sensor 3, air quality sensor 4, toilet sensor 5, and PIT 11, and information, etc., received by the transmitter/receiver 12 is also used for resident behavior detection. Device actions, on the other hand, mean opening and closing actions for the windows 19 and 20 provided in the bedroom 16 and living room 15 in FIG. 1, power on/off actions for the TV 21 located in the living room 15, and opening and closing actions for the door of the refrigerator 22 located in the kitchen 14, and these actions are detected, respectively, by the window open/close detector 6, window open/close detector 7, TV power on/off detector 8, and refrigerator door open/close detector 9.

The information providing unit 30, in which many items of information relating to the care of the resident are set, is means for selecting one or a plurality of information items from the many information items set, on the basis of the behavior of the resident accurately specified by the specifying unit 29, and providing that selected information. This selected information is output from the loudspeaker 13. An actual example of care-related information will be described when the operation of the care system of embodiment 2 is explained later.

The control unit 31 is means for controlling the actions of devices located in the resident's residence based on the behavior of the resident accurately specified by the specifying unit 29, and is connected by cables to the devices subject to control. In embodiment 2, the window 20 provided in the living room 15 is used as an example of a device subject to control.

The notifying unit 32 is means for giving notification of the behavior of the resident accurately specified by the specifying unit 29 is means for outputting the accurately specified resident's behavior to a loudspeaker connected to the notifying unit 32 via a telephone line. The loudspeaker is located in a residence separate from the residence in which the resident lives. This loudspeaker outputs the accurately specified resident's behavior in speech form from the notifying unit 32. This loudspeaker is not shown in the figure.

In embodiment 2, the CCD cameras 1a and 1b, infrared ray sensor 2, in-bed state sensor 3, air quality sensor 4, toilet sensor 5, PIT 11, and transmitter/receiver 12 are used as an example of the first detecting means of the care systems according to claims 12 through 14. Also, the window open/close detectors 6 and 7, TV power on/off detector 8, and refrigerator door open/close detector 9 are used as an example of the second detecting means of the care systems according to claims 12 through 14. Further, the specifying unit 29 within the management unit 28 are used as an example of the specifying unit of the care systems according to claims 12 through 14.

In embodiment 2, the information providing unit 30 within the management unit 28 is used as an example of the information providing unit of the care system according to claim 12, the control unit 31 within the management unit 28 is used as an example of the control unit of the care system according to claim 13, and the notifying unit 32 within the management unit 28 is used as an example of the notifying unit of the care system according to claim 14.

Next, the operation of the care system according to embodiment 2 of the present invention will be described.

As described in embodiment 1, the CCD cameras 1a and 1b, infrared ray sensor 2, in-bed state sensor 3, air quality sensor 4, toilet sensor 5, and PIT 11 detect the behavior of the subject resident, and output the various detection data to the specifying unit 29 within the management unit 28. Also, as described in embodiment 1, the transmitter/receiver 12 outputs information on the person carrying the specified PIT 11 to the specifying unit 29. The window open/close detectors 6 and 7, TV power on/off detector 8, and refrigerator door open/close detector 9 detect, respectively, window 19 and 20 opening and closing actions, TV 21 power on/off actions, and refrigerator 22 door opening and closing actions, and output the respective detection data to the specifying unit 29.

The specifying unit 29 specifies the exact behavior of the resident on the basis of the input resident behavior detection data and device action detection data. For example, if the resident is detected to be in the living room 15 for a long time by the CCD camera 1b, and during the time in which that resident is detected to be in the living room 15, the power of the TV 21 is detected to be on by the TV power on/off detector 8, the specifying unit 29 specifies the fact that the resident has been watching TV for a long time in the living room 15.

The information providing unit 30 selects and provides information on the basis of the exact behavior of the resident specified by the specifying unit 29, and outputs that information to the loudspeaker 13. For example, if the specifying unit 29 specifies the fact that the resident has been watching TV 21 for a long time in the living room 15, as described above, since this implies a lack of exercise, information advising the resident to go out and take some exercise is provided, together with an exercise menu listing suitable kinds of exercise. Information to be provided is set in the information providing unit 30, and some of that set information comprises information recommending bodily exercise, and exercise menus. For example, there may be a number of applicable exercise menus based on the length of time for which the resident has not moved, with a suitable menu being selected and provided.

The control unit 31 controls window 20 opening and closing actions on the basis of the exact behavior of the resident specified by the specifying unit 29. For example, if the specifying unit 29 specifies the fact that the resident has been watching TV 21 for a long time in the living room 15, as described above, the control unit 31 will determine the ventilation of the living room 15 to be inadequate, and open the window for, say, ten minutes.

The notifying unit 32 outputs the exact behavior of the resident, specified by the specifying unit 29, to a loudspeaker installed in a residence separate from that of the resident. This loudspeaker thus outputs the accurately specified behavior of the resident in speech form. Therefore, a resident of a different residence can ascertain the accurately specified behavior of the subject resident.

In the above described embodiment 2, the operation of the care system of the present invention has been described taking the example of the case where the resident is specified as having been watching TV 21 for a long time in the living room 15, based on the input resident behavior detection data and device action detection data. Thus, the specifying unit 29 of the present invention is means for specifying the exact behavior of a resident on the basis of the input resident behavior detection data and device action detection data, and enables specification of the fact that, for example, the resident's activity pattern is abnormal, or that the resident is going to the toilet frequently, is taking a nap on the sofa, is wandering about at night, or has fallen in the toilet or bathroom.

If the specifying unit 29 finds that the resident's activity pattern is abnormal, for example, the information providing unit 30 will select and provide information urging regular sleeping and waking habits from among the many set pieces of information. And if the specifying unit 29 finds that the resident is visiting the toilet frequently, for example, the information providing unit 30 will select and provide information suggesting the possibility of diabetes, or information recommending consulting a doctor, from among the many set pieces of information.

If the specifying unit 29 finds that the resident is taking a nap on the sofa, for example, the information providing unit 30 will select and provide the information "You will catch cold" and the loudspeaker 13 output that information in speech form, while the control unit 31 controls the lighting units and air conditioner to darken the room and adjust the room temperature to a level that will prevent the resident from catching cold. Also, the notifying unit 32 will output information indicating that the resident is napping on the sofa, to a loudspeaker installed in another residence. As this loudspeaker thus outputs the accurately specified behavior of the resident in speech form, the resident of the other residence is able to ascertain the fact that the subject resident is napping on the sofa, and take the subject resident a blanket.

If the specifying unit 29 finds that the resident is wandering at night, or has fallen in the toilet or bathroom, for example, the notifying unit 32 will output information to that effect to a loudspeaker installed in another residence. As this loudspeaker thus outputs the accurately specified behavior of the resident in speech form, the resident of the other residence is able to ascertain the fact that the subject resident is wandering at night or has fallen in the toilet or bathroom, and take appropriate action.

Thus far, it has been assumed that the specifying unit 29 specifies the exact behavior of the resident on the basis of input resident behavior detection data and device action detection data, but it is also possible for detection data whereby the physiological state and/or psychological state of the resident are specified also to be input, and the behavior of the resident to be accurately specified. In this case, a third detecting means is necessary to enable the physiological state and/or psychological state of the resident to be specified, and the third detecting means described in embodiment 1 can be used as this third detecting means.

If the specifying unit 29 specifies an increase in the resident's heart rate or blood pressure, for example, the information providing unit 30 provides information to that effect, and also provides information recommending consulting a doctor. Using a third detecting means in this way, capable of detecting the physiological state and/or psychological state of the resident, allows health management for middle-aged and elderly persons with high blood pressure.

If the specifying unit 29 finds that the resident tends to stay indoors and, according to the results of psychological tests, is found to suffer from mental stress, the control unit 31 will control the operation of a stereo player to output soothing music, and control the air conditioner to increase the indoor negative ion count. In addition, the control unit 31 will control the operation of the lighting units and an aroma generator to provide soothing lighting and a soothing aroma indoors.

In the above described embodiment 2, the CCD cameras 1a and 1b, infrared ray sensor 2, in-bed state sensor 3, air quality sensor 4, toilet sensor 5, PIT 11, and transmitter/receiver 12 are used as an example of the first detecting means of the care systems according to claims 12 through 14; however, the first detecting means is not limited to the above described CCD cameras 1 and infrared ray sensor 2. The first detecting means can be any means of detecting the behavior of the subject resident.

In the above described embodiment 2, the window open/close detectors 6 and 7, TV power on/off detector 8, and refrigerator door open/close detector 9 are used as an example of the second detecting means of the care systems according to claims 12 through 14; however, the second detecting means is not limited to the above described window open/close detector 6 and TV power on/off detector 8. The second detecting means can be any means of detecting the actions of the relevant devices.

In the above described embodiment 2, the control unit 31 is used as an example of the control means of the care system according to claim 13, and this control unit 31 is taken as controlling the operation of the window 20, etc.; however, the control unit 31 is not limited to control of the operation of the window 20, etc., but is a unit that controls the operation of devices installed in the resident's residence, on the basis of the behavior of the resident accurately specified by the specifying unit 29.

In the above described embodiment 2, the notifying unit 32 output the behavior of the resident accurately specified by the specifying unit 29 to a loudspeaker connected to the notifying unit 32 by a telephone line; the loudspeaker is installed in a different residence from that of the subject resident, however, the notifying unit 32 and the loudspeaker can also be connected by an electric light cable or dedicated line, rather than a telephone line. Also, instead of a loudspeaker, a display unit can be used that displays the accurately specified behavior of the resident by means of optical signals.

Some or all of the component elements of the care system of the above described embodiment 2 may be hardware, or may be software with the same functions as the corresponding functions of that hardware.

The present invention also covers a care residence comprising the above described care system.

The present invention also covers media holding a program and/or data for execution by a computer of some or all of the functions of some or all of the component elements of the above described care system, those media being capable of being. processed by a computer.

Media include recording media such as ROM, transmission media such as the Internet, and light, electric-wave, sound-wave, and similar transmission media. Holding media include, for example, recording media on which programs and/or data are recorded, transmission media that transmit programs and/or data, and so forth. Therefore, the present invention also covers media on which is recorded a program and/or data for execution by a computer of some or all of the functions of some or all of the component elements of the above described care system, those media being capable of being processed by a computer, and whereby the read above described program and/or data execute the above described functions in collaboration with the above described computer.

"Capable of being processed by a computer" means, in the case of a recording medium such as ROM, for example, capable of being read by a computer, and in the case of a transmission media, that the program and/or data to be transmitted can be handled by a computer as the result of transmission.

The present invention also covers a collection of information comprising programs and/or data for execution by a computer of some or all of the functions of some or all of the component elements of the above described care system.

This "collection of information" includes, for example, software such as programs and/or data.

The data in the above described media and information collection system include data structures, data formats, data types, etc.

(Embodiment 3)

Next, the configuration of a behavior determining apparatus according to embodiment 3 of the present invention will be described using FIGS. 7 and 8.

Figure 7:
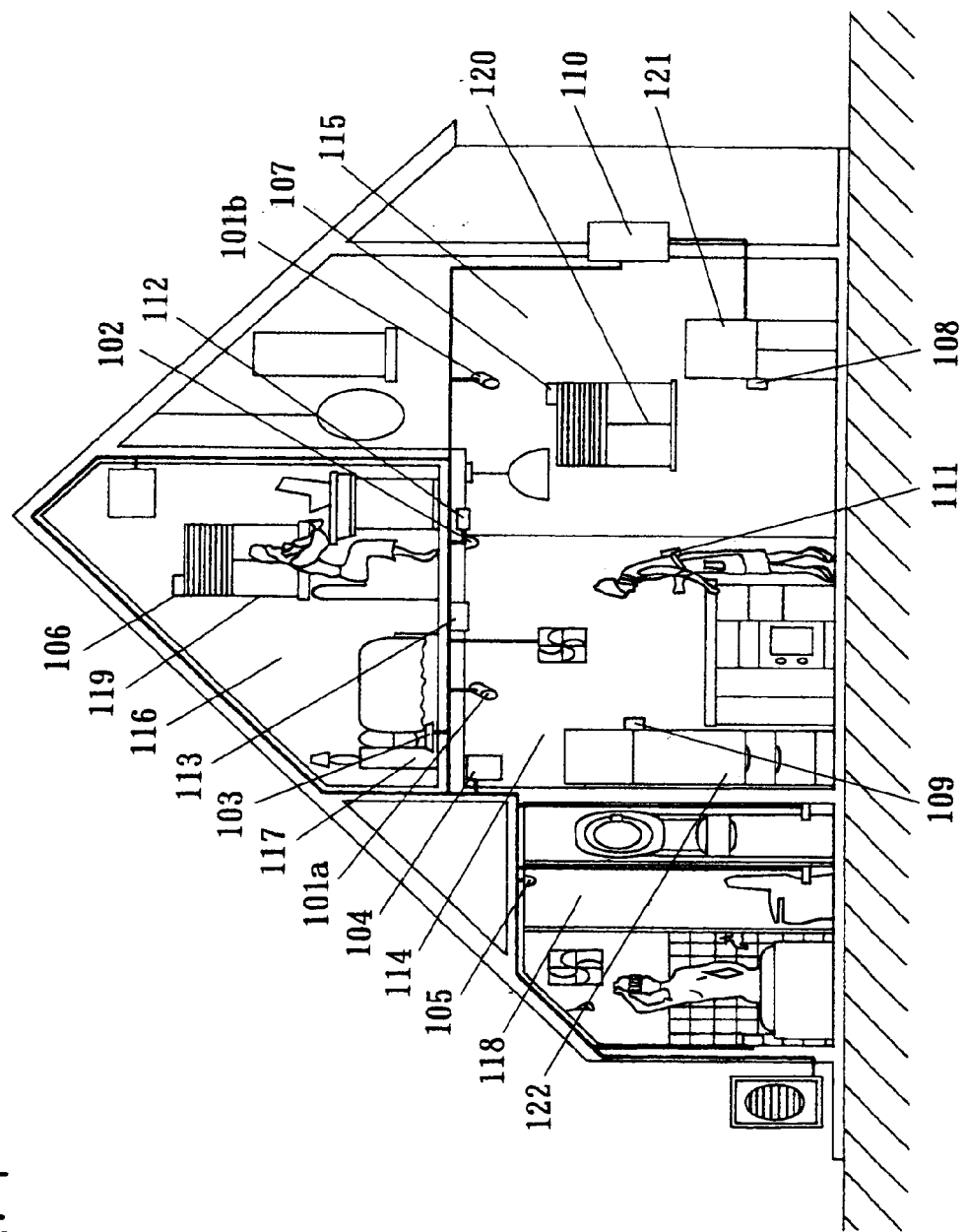
FIG. 7 is a drawing for explaining the location of each component unit when the several component units configuring the behavior determining apparatus of embodiment 3 of the present invention are installed in various locations in a residence, etc.

FIG. 7 is a drawing for explaining the location of each component unit when the several component units configuring the behavior determining apparatus of embodiment 3 of the present invention are installed in various locations in a residence, etc. FIG. 8 is a block diagram of the behavior determining apparatus of embodiment 3 of the present invention.

As shown in FIG. 7, the behavior determining apparatus of embodiment 3 of the present invention is configured by CCD cameras 101a and 101b, an infrared ray sensor 102, an in-bed state sensor 103, an air quality sensor 104, a toilet sensor 105, window open/close detectors 106 and 107, a TV power on/off detector 108, a refrigerator door open/close detector 109, a management unit 110, a PIT 111, a transmitter/receiver 112, and a loudspeaker 113.

CCD camera 101a is installed on the ceiling of the kitchen 114 on the first floor of the residence, and is means for viewing the situation in the kitchen 114 area, while CCD camera 101b is installed on the ceiling of the first-floor living room 115, and is means for viewing the situation in the living room 115 area. The infrared ray sensor 102 is installed on the ceiling of the first-floor living room 115 at the doorway dividing the kitchen 114 from the living room 115, and is means for detecting human movement between the kitchen 114 and the living room 115. The in-bed state sensor 103 is installed between the support of the bed 117 located in the second-floor bedroom 116 and the floor on which the bed 117 is placed, and is means for detecting whether a person is in the bed 117 by detecting a load applied to the bed 117. The air quality sensor 104 is installed on the ceiling of the kitchen 114, and is means for measuring the room humidity and concentration of volatile organic substances and $CO_2$, while the toilet sensor 105 is installed on the ceiling of the toilet 118, and is means for measuring the general position of a person who has entered the toilet 118, and the length of time spent there, using an infrared distance sensor.

A window open/close detector 106 is installed on the window 119 in the bedroom 116, and is means for detecting whether the window 119 is open or closed. Similarly, a window open/close detector 107 is installed on the window 120 in the living room 115, and is means for detecting whether the window 120 is open or closed. The TV power on/off detector 108 is means for detecting whether the power of the TV 121 located in the living room 115 is on or off, by making use of the fact that the amount of current when the TV 121 is on is larger than when it is off, or by detecting whether the TV 121 is receiving a remote controller switch signal, etc. The refrigerator door open/close detector 109 is fitted to the refrigerator 122 located in the kitchen 114, and is means for detecting whether the door is open or closed.

Figure 8:
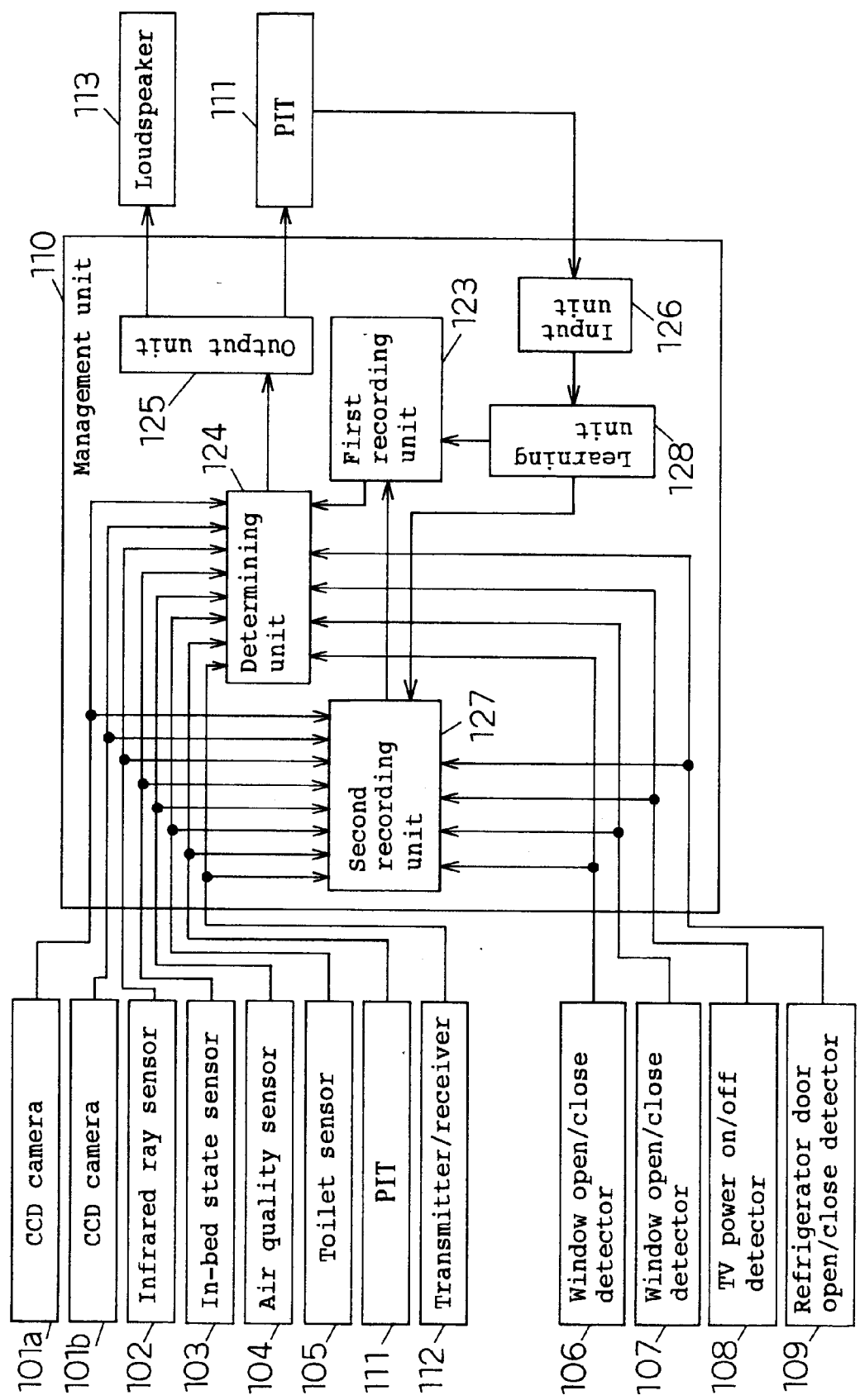
FIG. 8 is a block diagram of the behavior determining apparatus of embodiment 3 of the present invention.

The management unit 110 is installed within a wall of the living room 115, and as shown in FIG. 8, is configured by a first recording unit 123, a determining unit 124, an output unit 125, an input unit 126, a second recording unit 127, and a learning unit 128.

The first recording unit 123 is means for recording the pattern of behavior of the resident of the residence in FIG. 7, and the pattern of action of devices installed in the residence. The determining unit 124 is means for comparing the actual behavior of the resident with the pattern of behavior recorded in the first recording unit 123, and determining whether the behavior of the resident is substantially identical to the pattern of behavior recorded in the first recording unit 123. Moreover, the determining unit 124 is also means for comparing the actual actions of devices with the pattern of action of devices recorded in the first recording unit 123, and determining whether device actions are substantially identical to the pattern of action.

In this embodiment, the actual behavior of the resident is detected by means of the CCD cameras 101a and 101b, infrared ray sensor 102, in-bed state sensor 103, air quality sensor 104, toilet sensor 105, and PIT 111. In addition, information received by the transmitter/receiver 112 is also used for detection of the resident's behavior. Actual actions of devices in the present embodiment mean opening and closing actions for the windows 119 and 120 provided in the bedroom 116 and living room 115, power on/off actions for the TV 121 located in the living room 115, and opening and closing actions for the door of the refrigerator 122 located in the kitchen 114, and these actions are detected, respectively, by the window open/close detector 106, window open/close detector 107, TV power on/off detector 108, and refrigerator door open/close detector 109.

The output unit 125 is means for outputting an alarm if the result of the determination by the determining unit 124 is negative. The input unit 126 is means for inputting the resident's response to an alarm output by the output unit 125. The second recording unit 127 is means for temporarily recording the behavior of the resident detected by the CCD cameras 101a and 101b, infrared ray sensor 102, in-bed state sensor 103, air quality sensor 104, toilet sensor 105, PIT 111, and transmitter/receiver 112. In addition, the second recording unit 127 is means for temporarily recording window 119 and 120 opening and closing actions, TV 121 power on/off actions, and refrigerator 122 door opening and closing actions, detected by the window open/close detector 106, window open/close detector 107, TV power on/off detector 108, and refrigerator door open/close detector 109. The learning unit 128 is means for controlling the operation of the first recording unit 123 and the second recording unit 127 as instructed, when the resident's response input by the input unit 126 is an instruction for the resident behavior or device actions temporarily recorded in the second recording unit 127 to be additionally recorded in the first recording unit 123 as a new pattern, or an instruction for all or part of the pattern recorded in the first recording unit 123 to be changed to part of the above described new pattern.

The PIT 111 is a personal information terminal carried by the resident in FIG. 7, capable of transmitting and receiving information by electric wave, and incorporates means for issuing by means of a weak electric wave an specification number, unique to the resident carrying the PIT 111, for the purpose of specifying that resident when a given instruction by a electric wave from the transmitter/receiver 112 is received. The PIT 111 also incorporates means for receiving an alarm output by electric wave from the output unit 125 of the management unit 110, emitting sound, vibration, and light based on that alarm, and notifying the resident of the alarm. The PIT 111 is also means for inputting the resident's response when an alarm is issued, and transmitting that response by electric wave.

In addition, the PIT 111 has a gyro sensor, acceleration sensor, and angle sensor, and is also means for detecting the attitude of the carrier (standing, sitting, prone, etc.). The PIT 111 also has a function for detecting a moving state and the amount of activity, and further incorporates functions that allow detection of the physiological state of the carrier (heart rate, body temperature, etc.). Information transmission and reception by the PIT 111 is performed by means of PHS system communication or by means of specific low-power communication using a frequency band of several hundred MHz. In FIG. 8, two PITs are shown, but these two PITs are the same unit; two PITs are shown for the sake of explanation, since there are a plurality of PIT 111 functions.

The transmitter/receiver 112 is installed on the ceiling at the entrance/exit dividing the kitchen 114 from the living room 115, touching the infrared ray sensor 102, and is means for enabling electric-wave transmission and reception of information, and means for specifying the person who moved when information is input indicating that human movement has been detected from the infrared ray sensor 102.

The loudspeaker 113 is means for issuing a warning sound on the basis of an alarm output by the output unit 125 of the management unit 110.

In embodiment 3, the CCD cameras 101a and 101b, infrared ray sensor 102, in-bed state sensor 103, air quality sensor 104, toilet sensor 105, PIT 111, and transmitter/receiver 112 are used as an example of the detecting means of the behavior determining apparatus of the present invention according to claim 21. Also, the window open/close detectors 106 and 107, TV power on/off detector 108, and refrigerator door open/close detector 109 are used as an example of the detecting means of the behavior determining apparatus of the present invention according to claim 22.

In embodiment 3, the first recording unit 123 within the management unit 110 is used as an example of the recording means, and the determining unit 124 within the management unit 110 as an example of determining means, respectively, of the behavior determining apparatus of the present invention according to claims 21 and 22. Also, the output unit 125 within the management unit 110, the PIT 111, and the speaker 113 is used as an example of the notifying means of the behavior determining apparatus of the present invention according to claims 21 and 22. Further, the input unit 126 is used as an example of the input means of the behavior determining apparatus of the present invention according to claims 21 and 22.

In embodiment 3, the second recording unit 127 is used as an example of the second recording means, and the learning unit 128 as an example of the learning means, respectively, of the behavior determining apparatus of the present invention according to claim 23.

Also, the transmitter/receiver 112 is used as an example of the first transmitting/recording means of the behavior determining apparatus of the present invention according to claim 29, and the second transmitting/recording unit is provided in the PIT 111.

Next, the operation of the behavior determining apparatus according to embodiment 3 of the present invention will be described.

First, regarding the resident, the behavior of the subject resident detected by the CCD cameras 101a and 101b, infrared ray sensor 102, in-bed state sensor 103, air quality sensor 104, toilet sensor 105, PIT 111, and transmitter/receiver 112, is recorded in the first recording unit 123 of the management unit 110. Similarly, when the resident causes actions to be recorded in the first recording unit 123, window 119 and 120 opening and closing actions, TV 121 power on/off actions, and refrigerator 122 door opening and closing actions, detected by the window open/close detectors 106 and 107, TV power on/off detector 108, and refrigerator door open/close detector 109, are recorded in the first recording unit 123.

Here, for the purposes of the following explanation, recording of the behavior of the above described subject resident, and window 119 and 120 opening and closing actions, TV 121 power on/off actions, and refrigerator 122 door opening and closing actions, in the first recording unit 123, is assumed to have been performed continuously throughout the year 1998. It is also assumed that the resident behavior recorded in the first recording unit 123 has been averaged for each month, and recorded beforehand in the first recording unit 123 as the behavior patterns of the subject resident. Similarly, it is assumed that window 119 and 120 opening and closing actions, TV 121 power on/off actions, and refrigerator 122 door opening and closing actions have been averaged for each month, and recorded beforehand in the first recording unit 123 as device action patterns.

Figure 9:
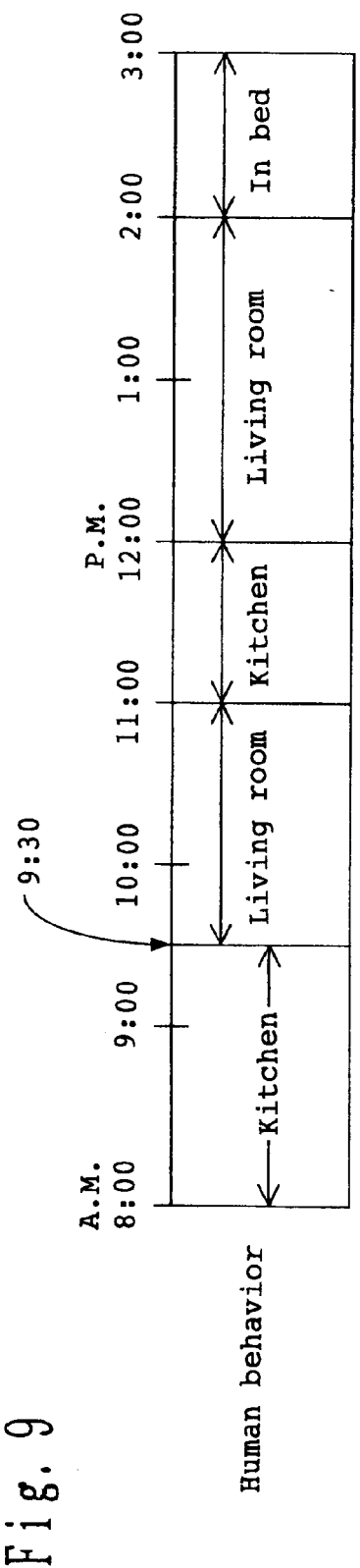
FIG. 9 is a drawing showing part of pattern 1 recorded in the first recording unit 123 of the behavior determining apparatus of embodiment 3 of the present invention.
Figure 10:
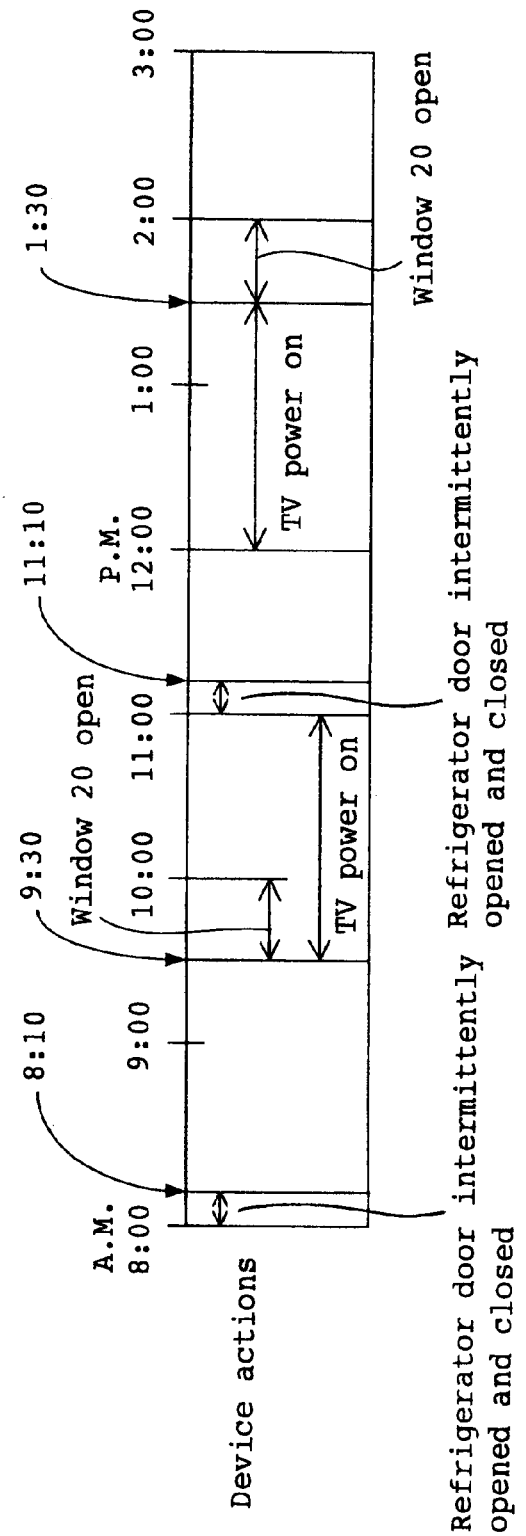
FIG. 10 is a drawing showing part of pattern 2 recorded in the first recording unit 123 of the behavior determining apparatus of embodiment 3 of the present invention.

Therefore, in this embodiment, the first recording unit 123 has recorded averaged the subject resident's behavior patterns and the device action patterns for each month of 1998. Here, the behavior pattern for July 1998 recorded in the first recording unit 123 is taken as pattern 1, and the device action pattern as pattern 2, and FIG. 9 shows the part of pattern 1 from 8 a.m. to 3 p.m., while FIG. 10 shows the part of pattern 2 from 8 a.m. to 3 p.m.

First, the part of pattern 1 will be described. As shown in FIG. 9, from 8 a.m. to 9:30 a.m. in pattern 1, the resident is determined to be in the kitchen 114 from the fact that the figure of the resident is included in the view of the kitchen 114 shot by the CCD camera 101a, and the $CO_2$ concentration in the kitchen 114 measured by the air quality sensor 104 has exceeded a given threshold level, and this is recorded in the first recording unit 123. When a person is in the kitchen 114, the $CO_2$ concentration in the kitchen 114 rises, and therefore the air quality sensor 104 can detect whether a person is in the kitchen 114 by measuring the concentration of $CO_2$ in the kitchen 114. Also, if the person in the kitchen 114 is cooking, the humidity, $CO_2$ concentration, and concentration of volatile organic constituents increase, and therefore the air quality sensor 104 can detect whether a person is in the kitchen 114 by measuring some or all of these parameters-humidity, $CO_2$ concentration, and concentration of volatile organic constituents-in the kitchen 114.

Then, at 9:30 a.m., the fact that the resident has left the kitchen 114 and entered the living room 115 is detected from the fact that the infrared ray sensor 102 has detected human movement and the figure of the resident has disappeared from the view of the kitchen 114 shot by the CCD camera 101a, as well as from the fact that the $CO_2$ concentration in the kitchen 114 measured by the air quality sensor 104 has fallen below the given threshold level, and that the figure of the resident has appeared in the view of the living room 115 shot by the CCD camera 101b, and this has been recorded in the first recording unit 123. Then, from 9:30 to 11:00, the resident remains within the view of the living room 115 shot by the CCD camera 101b, and so the fact that the resident is in the living room 115 is thus detected, and is recorded in the first recording unit 123.

At 11 a.m., the infrared ray sensor 102 again detects human movement and the figure of the resident is included in the view of the kitchen 114 shot by the CCD camera 101a, in addition to which the humidity, $CO_2$ concentration, and concentration of volatile organic constituents in the kitchen 114 measured by the air quality sensor 104 exceed the given threshold level, as a result of which the resident is detected to be in the kitchen 114, and this is recorded in the first recording unit 123.

At 12 noon, due to detection of an infrared ray again by the infrared ray sensor 102, etc., the fact that the resident has left the kitchen 114 and entered the living room 115 is recorded in the first recording unit 123. Then, from 2 p.m. to 3 p.m., the fact that the resident is in bed 117 is detected through detection by the in-bed state sensor 103 of a load applied to the bed 117, and this is recorded in the first recording unit 123.

As stated above, pattern 1 is the averaged behavior pattern for July 1998.

Also, when the resident moves from the kitchen 114 to the living room 115, or from the living room 115 to the kitchen 114, human movement is detected by the infrared ray sensor 102, and in this case the infrared ray sensor 102 outputs information to the effect that human movement has been detected to the transmitter/receiver 112. The transmitter/receiver 112 then transmits to the PIT 111, by means of an electric wave with a high degree of directivity for a restricted area, an instruction for issuing an specification number to specify the person carrying the PIT 111. On receiving the instruction, the PIT 111 issues by means of an electric wave an specification number to specify the person carrying the PIT 111, and, based on the specification number from the PIT 111, the transmitter/receiver 112 specifies the person who emitted the infrared ray detected by the infrared ray sensor 102. By means of this specification, the identity of the person who moved from the kitchen 114 to the living room 115, or from the living room 115 to the kitchen 114, is ascertained.

This kind of specification method can be used when a number of people are living in the same residence, to specify who moved between adjacent rooms, or who moved either way between a room and adjacent passageway. Also, to specify who moved either way between a room and adjacent passageway, means, such as the above described transmitter/receiver 112, must be installed on the ceiling at the junction of the room and passageway, for example, for specifying who moved either way between the room and adjacent passageway based on an specification number from the PIT 111.

Next, the part of pattern 2 will be described. As shown in FIG. 10, from 8 a.m. to 3 p.m., window open/close detector 106 detects that the window 119 is closed, while window open/close detector 107 detects that the window 120 is open from 9:30 a.m. to 10 a.m. and from 1:30 p.m. to 2 p.m., and is closed at other times, and these facts are recorded in the first recording unit 123.

The TV power on/off detector 108 detects the TV 121 power to be on from 9:30 a.m. to 11 a.m. and from 12 noon to 1:30 p.m., and to be off at other times, and these facts are recorded in the first recording unit 123. The refrigerator door open/close detector 109 detects that the door of the refrigerator 122 was repeatedly opened and closed intermittently between 8 a.m. and 8:10 a.m., and between 11 a.m. and 11:10 a.m., and was closed at other times, and these facts are recorded in the first recording unit 123 as part of pattern 2.

As stated above, pattern 2 is the averaged device action pattern for July 1998.

Figure 11:
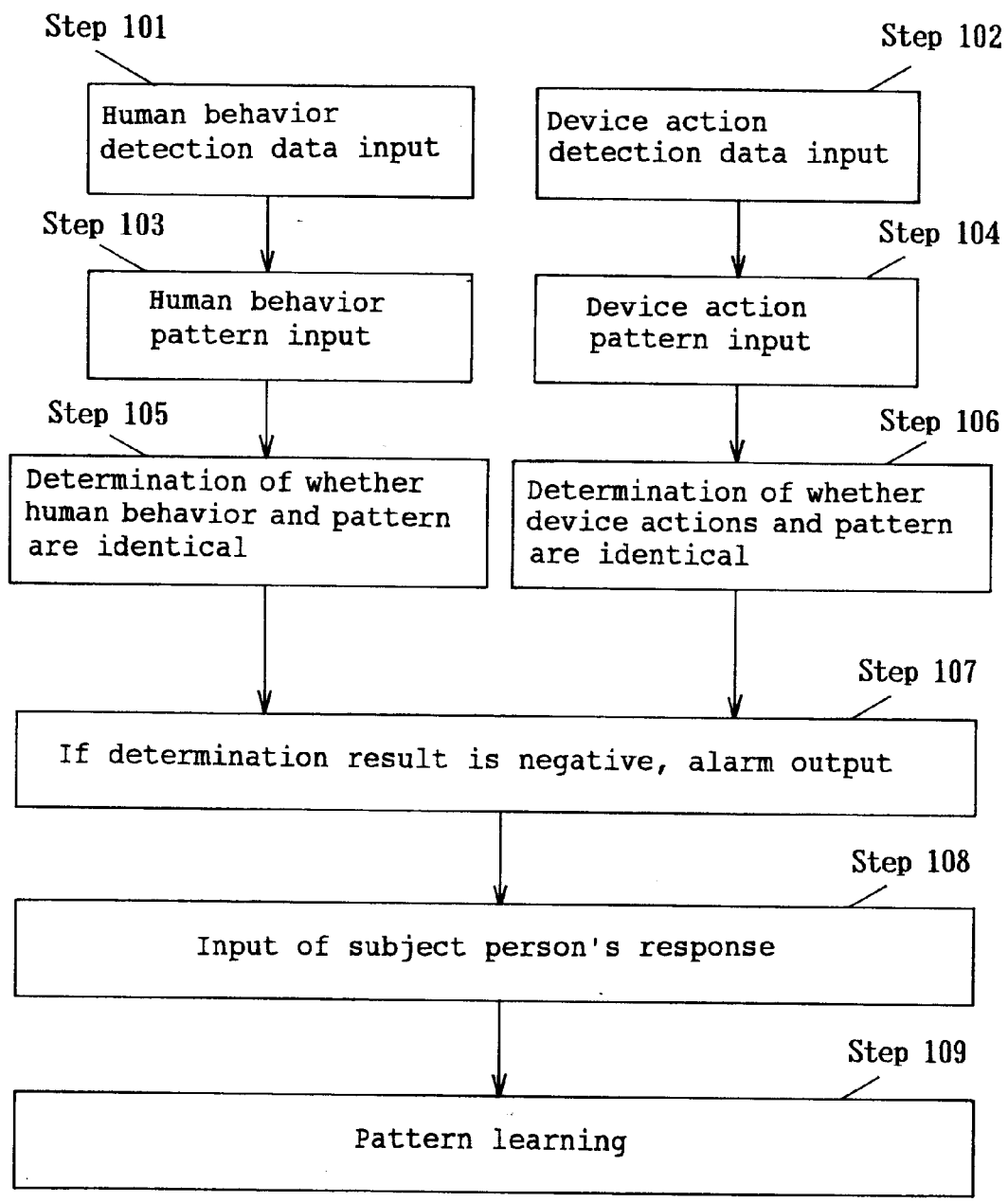
FIG. 11 is a flowchart showing the operation of the behavior determining apparatus of embodiment 3 of the present invention.

Next, the operation of the behavior determining apparatus of embodiment 3 of the present invention after pattern 1 and pattern 2 have been recorded in the first recording unit 123 will be described using the flowchart in FIG. 11. For purposes of explanation, the operation of the behavior determining apparatus of embodiment 3 of the present invention for Jul. 22, 1999, will be described.

The behavior of the resident on this July 22 is detected by the CCD cameras 101a and 101b, infrared ray sensor 102, in-bed state sensor 103, air quality sensor 104, toilet sensor 105, and PIT 111, and the detection data of each is input to the determining unit 124 shown in FIG. 8 (step 101). In addition, information on the person carrying the PIT 111, specified by the transmitter/receiver 112, is also input to the determining unit 124 (step 101).

July 22 window 119 and 120 opening and closing actions, TV 121 power on/off actions, and refrigerator 122 door opening and closing actions, are detected, respectively, by the window open/close detectors 106 and 107, TV power on/off detector 108, and refrigerator door open/close detector 109, and the detection data of each is input to the determining unit 124 (step 102).

Each kind of data input to the determining unit 124 is also input to the second recording unit 127, where it is recorded and stored temporarily.

Next, the determining unit 124 also inputs pattern 1 and pattern 2 recorded in the first recording unit 123 (steps 103 and 104), and determines whether the resident's behavior is identical with pattern 1 within a given time period or within a given range of behavior (step 105). Similarly, the determining unit 124 determines whether device actions are identical with pattern 2 within a given time period or within a given range of actions (step 106). Then, if the result of the determination by the determining unit 124 is that the resident's behavior is not identical with pattern 1 within a given time period or within a given range of behavior, or that device actions are not identical with pattern 2 within a given time period or within a given range of actions, the output unit 125 outputs an alarm (step 107). The operation of the behavior determining apparatus of embodiment 3 after the output unit 125 outputs an alarm will be described below together with an actual example.

To take an actual example for the purpose of explanation, it will be assumed that the resident visits the hospital on the same day each week starting from July 22, and that he/she leaves home at 9 a.m. to go to the hospital. The resident goes to the kitchen 114 at 8 a.m. and prepares breakfast, finishes breakfast at 8:30 a.m., and enters the living room 115. The resident opens and closes the refrigerator 122 intermittently between 8 a.m. and 8:10 a.m. Looking at device actions from 8 a.m. to 9 a.m., since the actual device actions detected by the refrigerator door open/close detector 109 are identical with pattern 2 recorded in the first recording unit 123, the determining unit 124 determines that the device actions are identical with pattern 2. Therefore, the output unit 125 does not output an alarm.

Meanwhile, looking at the behavior of the resident during that same period of 8 a.m. to 9 a.m., since the actual behavior of the resident is not identical with pattern 1 recorded in the first recording unit 123, the determining unit 124 determines that the actual behavior of the resident detected by the CCD camera 101a, etc., is not identical with pattern 1. Therefore, the output unit 125 outputs an alarm to the PIT 111 and the loudspeaker 113. The output unit 125 is assumed to transmit the alarm by electric wave to the PIT 111. Then, when the PIT 111 receives the alarm by electric wave, it emits speech, vibration, and light on the basis of that alarm, notifying the resident of the alarm. The loudspeaker 113 also emits a warning sound. When warned in this way, the resident stops the alarm.

The resident usually visits the hospital on the same day each week starting from July 22, and since the resident's behavior on the day of the hospital visit differs from pattern 1, and the device actions associated with the resident's behavior also differ from pattern 2, it is assumed that the resident wishes to record the resident behavior and device actions on July 22 in the first recording unit 123 as new patterns. In this case, the resident inputs an instruction to perform additional recording of the behavior and device actions of July 22 in the first recording unit 123 as new patterns. The PIT 111 transmits the instruction received from the resident to the input unit 126 of the management unit 110 by electric wave, and the input unit 126 inputs the resident's instruction transmitted from the PIT 111 (step 108), and outputs it to the learning unit 128.

Now, since the second recording unit 127 temporarily records the resident's behavior and device actions of July 22, as described above, the resident's behavior and device actions temporarily recorded in the second recording unit 127 are additionally recorded by the learning unit 128 in the first recording unit 123 as part of a new pattern, based on the resident's instruction input by the input unit 126 (step 109). After the resident's behavior and device actions of July 22 have been temporarily recorded in the second recording unit 127, following input of the resident's instruction by the input unit 126, these are also recorded sequentially by the learning unit 128 in the first recording unit 123 as the remaining part of the new pattern.

As the resident's response to an alarm is input to the input unit 126 in this way, and control is performed so that a new pattern is recorded in the first recording unit 123 on the basis of that response, an alarm is not issued even if the resident's behavior on July 22 after input of the response by the input unit 126 and pattern 1 are not substantially identical, and an alarm is not issued if the resident shows substantially the same behavior as the July 22 behavior after the new pattern has been recorded in the first recording unit 123—or to be exact, from July 23 onward.

In embodiment 3, if the detected behavior of the resident and behavior corresponding to pattern 1 differ only within a time period of 10 minutes or less, the detected resident's behavior is regarded as being identical with pattern 1.

In the description thus far, an alarm is issued because the actual behavior of the resident is not identical with pattern 1, and as the response to that alarm, the input unit 126 inputs an instruction for recording the behavior and device actions of July 22, sent from the PIT 111 by electric wave, in the first recording unit 123 as a new pattern. However, the resident's response input by the input unit 126 may also be an instruction for replacing the part of pattern 1 and/or pattern 2 from 8 a.m. to 1 p.m. with that part of the July 22 behavior and device actions from 8 a.m. to 1 p.m., and recording the result in the first recording unit 123. Also, the resident's response input by the input unit 126 may also be an instruction for deleting pattern 1 and pattern 2 recorded in the first recording unit 123, and recording the behavior and device actions of July 22 in the first recording unit 123 as a new pattern 1 or pattern 2, respectively. In any case, the learning unit 128 controls the operation of the first recording unit 123 and the second recording unit 127 on the basis of the response input by the input unit 126.

In the description thus far, an alarm is issued because the actual behavior of the resident is not identical with pattern 1, but an alarm is also issued if the actual device actions are not identical with pattern 2. In this case, too, the resident responds to that alarm and the input unit 126 inputs that response. Then, based on that response, the learning unit 128 controls the operation of the first recording unit 123 and the second recording unit 127 as described above.

As explained above, the behavior determining apparatus of embodiment 3 of the present invention outputs an alarm if a pattern recorded beforehand in the first recording unit 123, and the actual behavior of the subject person or device actions, are not substantially identical, and the subject person's response to that alarm can be input. Also, based on that response, the subject person's behavior and device actions that are not substantially identical to the patterns are additionally recorded in the first recording unit 123 as new patterns, or recorded in the first recording unit 123, replacing some or all of the patterns already recorded in the first recording unit 123.

In the above described embodiment 3, the case has been described where the component units of the behavior determining apparatus are located in various places in a residence, etc., but the component units of the behavior determining apparatus are not restricted to only location in various places in a residence, etc., but may also be located in a hospital or care facility, for example. In this case, if a pattern recorded in the first recording unit 123 and the actual behavior of the subject person or device actions are not substantially identical, the output unit 125 can notify information to that effect to the hospital nurses' room or other administration section, either directly or via another device. In this way, a nurse or other member of the administration can accurately ascertain the behavior of the subject person.

Also, while a hospital or care facility has many subject persons, each subject person has transmitting means, such as the second transmitter/receiver provided in the above described PIT 111, for transmitting by electric wave an specification number that is unique to the subject person carrying the PIT 111 and is used to specify that subject person, or detecting means for detecting human movement, such as an infrared ray sensor, when the above described PIT 111 is carried, whereby the detected person is specified. If the subject person lives alone, for example, and the component units of the behavior determining apparatus are installed in that person's residence, as there is only one subject person, it is not necessary to provide the PIT 111 with means for specifying the person carrying that PIT 111. In this case, the output unit 125 will output information to an administration center, etc., for providing care for the subject person, such as a public welfare facility, and the behavior of the subject person will be managed by the public welfare facility, etc.

In the above described embodiment 3, the CCD cameras 101a and 101b, infrared ray sensor 102, in-bed state sensor 103, air quality sensor 104, toilet sensor 105, PIT 111, and transmitter/receiver 112 are used as an example of the detecting means of the behavior determining apparatus of the present invention according to claim 21; however, the detecting means of the behavior determining apparatus of the present invention according to claim 21 is not limited to the above described CCD cameras 101 or infrared ray sensor 102. The detecting means may be any means of detecting the behavior of the subject person. Moreover, the attitude, movement state, and degree of activity of the subject person are also applicable as behavior of the subject person.

In the above described embodiment 3, the window open/close detectors 106 and 107, TV power on/off detector 108, and refrigerator door open/close detector 109 are used as an example of the detecting means of the behavior determining apparatus of the present invention according to claim 22; however, the detecting means of the present invention is not limited to the above described window open/close detector 106 and TV power on/off detector 108. The detecting means may be any means of detecting the actions of the relevant devices.

In the above described embodiment 3, the resident inputs the response to an alarm to the PIT 111, and the input unit 126 inputs the resident's response from the PIT 111 by electric wave; however, it is also possible for the resident to input responses to a special response input device, and for the input unit 126 to input the resident's responses via that special response input device. In short, the input unit 126 need only input the resident's responses.

In the above described embodiment 3, on receiving a given instruction from the transmitter/receiver 112, the PIT 111 transmits by electric wave an specification number to specify the person carrying the PIT 111; however, it is also possible for the transmitter of the PIT 111, etc., to transmit an specification number by electric wave, regularly or irregularly, to specify an individual resident, regardless of whether or not a given instruction is received from the transmitter/receiver 112.

In the above described embodiment 3, the transmitter/receiver 112 specifies the person carrying the PIT 111; however, it is also possible for some or all of the CCD cameras 101a and 101b, infrared ray sensor 102, in-bed state sensor 103, air quality sensor 104, and toilet sensor 105 to have a function for specifying the person carrying the PIT 111, and for the person carrying the PIT 111 to be specified using an specification number transmitted by electric wave from the PIT 111.

In the above described embodiment 3, the first recording unit 123 records pattern 1 and pattern 2; however, the first recording unit 123 need only record one or a plurality of the subject person's behavior patterns and device action patterns. It is also possible to use means for recording one or a plurality of the subject person's behavior patterns only, and means for recording one or a plurality of device action patterns only, instead of the first recording unit 123. Also, the above mentioned first recording unit 123, is not limited to a unit that records the average patterns for each month of the year 1998, but may also record detection data for only one month as a pattern, or may also record averaged detection data for one month, or detection data for one month averaged for each day of the week, as a pattern. In short, all that is required is for means for recording one or a plurality of the subject person's behavior patterns, and means for recording one or a plurality of device action patterns, to be provided.

Also, the determining unit 124 need only compare one or a plurality of behavior patterns recorded by the first recording unit 123 with the actual behavior of the subject person, and determine whether or not the actual behavior of the subject person is substantially identical with any of the subject person's behavior patterns. And the determining unit 124 need only compare one or a plurality of device action patterns recorded by the first recording unit 123 with the actual device actions, and determine whether or not the actual device actions are substantially identical with any of the device action patterns.

The above expression "substantially identical" refers to the case where the subject person's behavior or device actions are identical with a pattern within a given time period of up to ten minutes, for example, or where, for example, since the subject person's behaviors of standing, and of bending down, in the kitchen 114 are both the same in terms of the subject person's being in the kitchen 114, the subject person's behavior and device actions are identical with a pattern within a given subject person behavior range or a given device action range of this kind.

In the above described embodiment 3, when the resident's behavior is determined by the determining unit 124 not to be substantially identical to pattern 1, the loudspeaker 113 emits a warning sound; however, an alarm lamp that displays an alarm by means of an optical signal may be used instead of the loudspeaker 113. In short, all that is required is for an alarm to be output when the resident's behavior or device actions are not substantially identical to any pattern recorded in the first recording unit 123.

In the above described embodiment 3, the determining unit 124 determines whether or not the subject person's behavior is substantially identical to any of the patterns recorded in the first recording unit 123, or whether or not device actions are substantially identical to any of the patterns recorded in the first recording unit 123; however, the determining unit 124 may also determine whether or not a combination of some or all of the subject person's behavior, device actions, subject person's physiological state, and subject person's psychological state, are substantially identical to any of the patterns recorded in the first recording unit 123. In this case, the patterns recorded in the first recording unit 123 must be patterns comprising a combination of some or all of the subject person's behavior, device actions, subject person's physiological state, and subject person's psychological state. Also, detecting means for detecting the physiological state and/or psychological state of the subject person must be provided.

As means for detecting the physiological state of the subject person, it is possible to use, for example, a thermometer that measures the body temperature of the subject person, a perspiration meter that measures the amount of perspiration produced by the subject person, and a heart rate meter that measures the heart rate of the subject person. As mentioned above, the PIT 111 incorporates functions that allow detection of the physiological state of the subject person (heart rate, body temperature, etc.), and therefore all that is required is for physiological information such as the heart rate and body temperature of the subject person to be transmitted by electric wave, regularly or irregularly, to that PIT 111, and for the transmitter/receiver 112 to receive that electric wave. This physiological information is then input to the determining unit 124. The physiological information can be input directly to the determining unit 124 by the subject person himself/herself or by a care-giver. As the means for detecting the psychological state of the subject person, some or all of the above mentioned instruments—thermometer, perspiration meter, and heart rate meter—and psychological state determining unit that determines changes in the psychological state based on changes in body temperature, amount of perspiration, and heart rate, etc., can be used.

In this way, some or all of the subject person's behavior, device actions, subject person's physiological state, and subject person's psychological state are detected by the individual detecting means, and a combination of the subject person's behavior and some or all of device actions, subject person's physiological state, and subject person's psychological state is recorded beforehand in the first recording unit 123 as a pattern. Then, all that is required is to allow the determining unit 124 to determine whether or not a combination of the actual subject person's behavior and some or all of device actions, subject person's physiological state, and subject person's psychological state, is substantially identical to the pattern. If the result of this determination is non-identity, the output unit 125 outputs an alarm. Then the input unit 126 inputs the subject person's response to that alarm.

If a combination of the detected subject person's behavior and some or all of device actions, subject person's physiological state, and subject person's psychological state is temporarily stored in the second recording unit 127, it is possible to additionally record new patterns in the first recording unit 123 according to the content of the response input to the input unit 126, and it is also possible to change part or all of the patterns already recorded.

In the detecting means for detecting the subject person's physiological state and/or the subject person's psychological state, it is also possible to set a function that specifies the subject person using information via electric wave for specifying subject persons, and a function that enables the physiological state and/or psychological state of that person to be detected, as with the CCD cameras 101, infrared ray sensor 102, in-bed state sensor 103, air quality sensor 104, or toilet sensor 105. Also, as mentioned above, the PIT 111 can be used as an example of the detecting means for detecting the subject person's physiological state and/or the subject person's psychological state.

Also, some or all of the component elements of the behavior determining apparatus of the above described embodiment 3 may be hardware, or may be software with the same functions as the corresponding functions of that hardware.

(Embodiment 4)

Next, the configuration of a behavior determining apparatus according to embodiment 4 of the present invention will be described using FIGS. 7 and 12.

FIG. 7 is a drawing for explaining the location of each component unit when the several component units configuring the behavior determining apparatus of embodiment 3 of the present invention, as described above, are installed in various locations in a residence, etc. As explained later, some of the component units configuring the behavior determining apparatus of embodiment 4 are the same as some of the component units configuring the behavior determining apparatus of embodiment 3, and therefore FIG. 7 will also be used when describing the behavior determining apparatus of embodiment 4. FIG. 12 is a block diagram of the behavior determining apparatus of embodiment 4 of the present invention.

Figure 12:
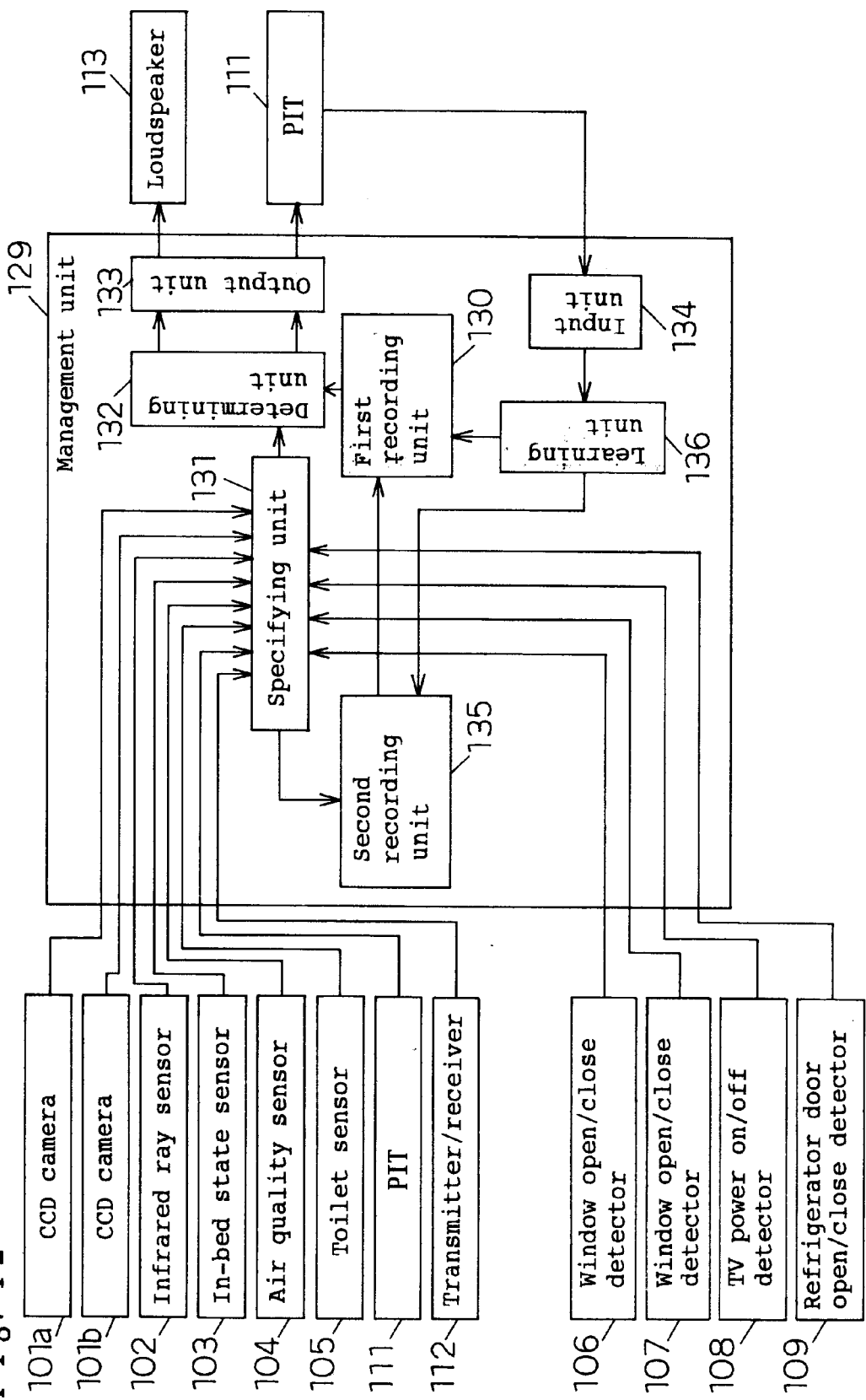
FIG. 12 is a block diagram of the behavior determining apparatus of embodiment 4 of the present invention.

As shown in FIG. 12, the behavior determining apparatus of embodiment 4 of the present invention is configured by CCD cameras 101a and 101b, an infrared ray sensor 102, an in-bed state sensor 103, an air quality sensor 104, a toilet sensor 105, window open/close detectors 106 and 107, a TV power on/off detector 108, a refrigerator door open/close detector 109, a management unit 129, a PIT 111, a transmitter/receiver 112, and a loudspeaker 113. The CCD cameras 101a and 101b, infrared ray sensor 102, in-bed state sensor 103, air quality sensor 104, toilet sensor 105, window open/close detectors 106 and 107, TV power on/off detector 108, refrigerator door open/close detector 109, PIT 111, transmitter/receiver 112, and loudspeaker 113 are identical to the corresponding component units configuring the behavior determining apparatus of embodiment 3 of the present invention described using FIGS. 7 and 8.

As with the management unit 110 of the behavior determining apparatus of embodiment 3, the management unit 129 is installed within a wall of the living room 115 in FIG. 7, and as shown in FIG. 12, is configured by a first recording unit 130, an specifying unit 131, a determining unit 132, an output unit 133, an input unit 134, a second recording unit 135, and a learning unit 136.

The first recording unit 130 is means for recording patterns in the same way as the first recording unit 123 described in embodiment 3. These patterns are precise resident behavior patterns. The specifying unit 131 is means for accurately specifying the behavior of the resident on the basis of resident behavior detected by the CCD cameras 101a and 101b, infrared ray sensor 102, in-bed state sensor 103, air quality sensor 104, and toilet sensor 105, and device actions detected by the window open/close detectors 106 and 107, TV power on/off detector 108, and refrigerator door open/close detector 109, The determining unit 132 is means for comparing the exact behavior of a resident specified by the specifying unit 131 with a pattern recorded in the first recording unit 130, and determining whether the exact behavior of the specified resident is substantially identical to the pattern.

The output unit 133 is means for outputting an alarm if the result of the determination by the determining unit 132 is negative. The input unit 134 is means for inputting the resident's response to an alarm output by the output unit 133. The second recording unit 135 is means for temporarily recording the exact behavior of the resident specified by the specifying unit 131. The learning unit 136 is means for controlling the operation of the first recording unit 130 and the second recording unit 135 as instructed, when the resident's response input by the input unit 134 is an instruction for the resident's exact behavior temporarily recorded in the second recording unit 135 to be additionally recorded in the first recording unit 130 as a new pattern, or an instruction for all or part of the pattern recorded in the first recording unit 130 to be changed to part of the above described new pattern.

In embodiment 4, the CCD cameras 101a and 101b, infrared ray sensor 102, in-bed state sensor 103, air quality sensor 104, toilet sensor 105, PIT 111, and transmitter/receiver 112 are used as an example of the first detecting means of the behavior determining apparatus of the present invention according to claim 26. Also, the window open/close detectors 106 and 107, TV power on/off detector 108, and refrigerator door open/close detector 109 are used as an example of the second detecting means of the behavior determining apparatus of the present invention according to claim 26.

In embodiment 4, the specifying unit 131 within the management unit 129 is used as an example of the specifying means, the first recording unit 130 within the management unit 129 as an example of the recording means, the determining unit 132 within the management unit 129 as an example of the determining means, the output unit 133 within the management unit 129 and the PIT 111 as an example of the notifying means, and the input unit 134 as an example of the input means, respectively, of the behavior determining apparatus of the present invention according to claim 26.

In embodiment 4, the second recording unit 135 is used as an example of the second recording means, and the learning unit 136 as an example of the learning means, respectively, of the behavior determining apparatus of the present invention according to claim 27.

As can be see by comparing FIG. 12 and FIG. 8, with the exception of differences between the configuration and operation of the management unit 129 of the behavior determining apparatus of embodiment 4 and the configuration and operation of the management unit 110 of the behavior determining apparatus of embodiment 3, the behavior determining apparatus of embodiment 4 is identical to the behavior determining apparatus of embodiment 3, and therefore in describing the operation of the behavior determining apparatus of embodiment 4 shown below, the description will mainly cover the differences from embodiment 3.

Next, the operation of the behavior determining apparatus according to embodiment 4 of the present invention will be described.

In embodiment 3, as shown in FIG. 8, the determining unit 124 determines whether or not the resident's behavior detected by the CCD cameras 101a and 101b, infrared ray sensor 102, in-bed state sensor 103, air quality sensor 104, toilet sensor 105, PIT 111, and transmitter/receiver 112 is substantially identical to pattern 1 recorded in the first recording unit 123, and also determines whether or not the actions comprising window 119 and 120 opening and closing actions, TV 121 power on/off actions, and refrigerator 122 door opening and closing actions, detected by the window open/close detectors 106 and 107, TV power on/off detector 108, and refrigerator door open/close detector 109, are substantially identical to pattern 2 recorded in the first recording unit 123.

In contrast to this, in embodiment 4, as shown in FIG. 12, the determining unit 132 determines whether or not the exact behavior of the resident specified by the specifying unit 131 and a pattern recorded in the first recording unit 130 are substantially identical. That is to say, a pattern of the exact behavior of the resident is recorded in the first recording unit 130, and the specifying unit 131 specifies the exact behavior of the resident.

Figure 13:
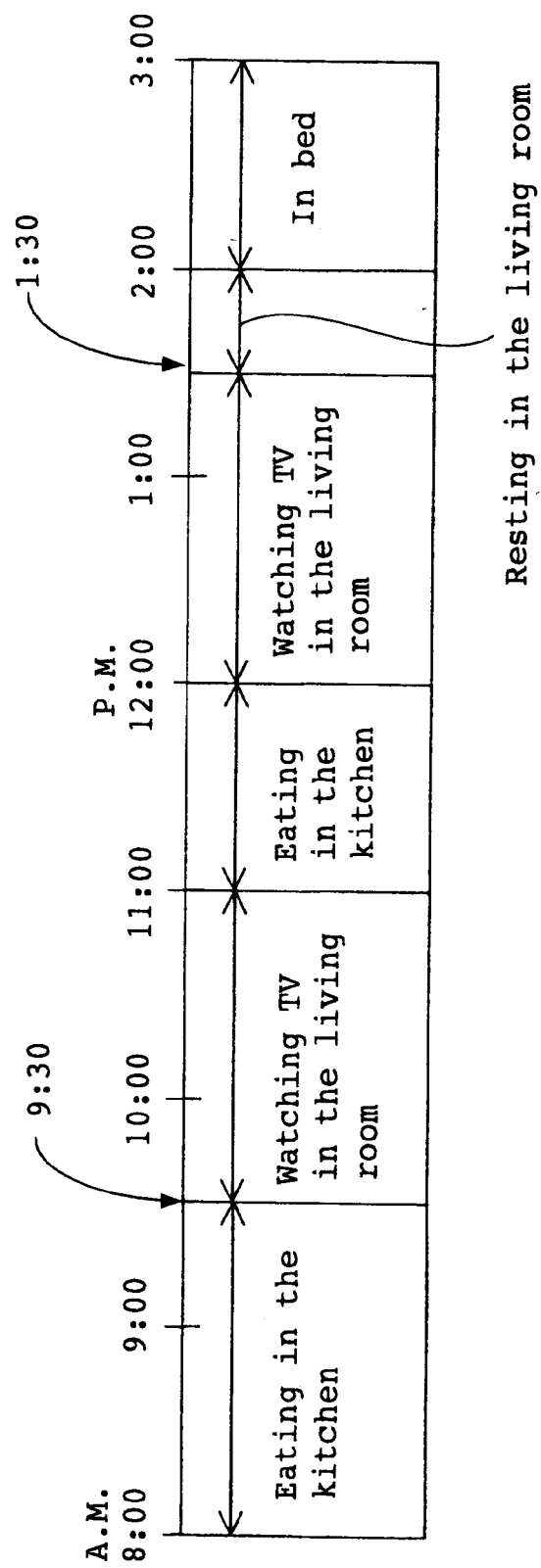
FIG. 13 is a drawing showing part of a pattern recorded in the first recording unit 130 of the behavior determining apparatus of embodiment 4 of the present invention.

First, the pattern of exact behavior of the resident recorded in the first recording unit 130 will be described. For purposes of explanation, it is assumed that part of the resident's exact behavior pattern recorded in the first recording unit 130 is the pattern shown in FIG. 13. The pattern shown in FIG. 13 corresponds to FIGS. 9 and 10 used with embodiment 3, and is a pattern of the exact behavior of the resident, specified from the human behavior in FIG. 9 and the device actions in FIG. 10.

To describe the content of the pattern in order, in the period from 8 a.m. to 9:30 a.m., according to the human behavior in FIG. 9 a person is in the kitchen, and according to the device actions in FIG. 10 the refrigerator door is opened and closed intermittently during a ten-minute period from 8 a.m.; therefore, the pattern for 8:00 to 9:30 is "eating in the kitchen." Next, from 9:30 to 11:00, according to the human behavior in FIG. 9 a person is in the living room, and according to the device actions in FIG. 10 the TV power is on; therefore, the pattern for 9:30 to 11:00 is "watching TV in the living room."

Then, from 11 a.m. to 12 noon, according to the human behavior in FIG. 9 a person is in the kitchen, and according to the device actions in FIG. 10 the refrigerator door is opened and closed intermittently during a ten-minute period from 11:00.; therefore, the pattern for 11:00 to 12:00 is "eating in the kitchen." Next, from 12 noon to 2 p.m., according to the human behavior in FIG. 9 a person is in the living room, and according to the device actions in FIG. 10 the TV power is on from 12:00 to 1:30, and the window 120 is open from 1:30 to 2:00; therefore, the pattern for 12:00 to 1:30 is "watching TV in the living room," and the pattern for 1:30 to 2:00 is "resting in the living room." Lastly, from 2 to 3 p.m., according to the human behavior in FIG. 9 a person is lying on the bed, and therefore the pattern for 2:00 to 3:00 is "in bed."

Next, the operation of the behavior determining apparatus of embodiment 4 of the present invention after the resident's exact behavior pattern has been recorded in the first recording unit 130 will be described. As with embodiment 3, for purposes of explanation, the operation of the behavior determining apparatus of embodiment 4 of the present invention for Jul. 22, 1999, will be described.

As described in embodiment 3, the behavior of the resident on this July 22 is detected by the CCD cameras 101a and 101b, infrared ray sensor 102, in-bed state sensor 103, air quality sensor 104, toilet sensor 105, and PIT 111, and the detection data of each is input to the specifying unit 131 shown in FIG. 12. In addition, information on the person carrying the PIT 111, specified by the transmitter/receiver 112, is also input to the specifying unit 131.

July 22 window 119 and 120 opening and closing actions, TV 121 power on/off actions, and refrigerator 122 door opening and closing actions, are detected, respectively, by the window open/close detectors 106 and 107, TV power on/off detector 108, and refrigerator door open/close detector 109, and the detection data of each is input to the specifying unit 131.

On the basis of the various input detection data, the specifying unit 131 specifies the exact behavior of the resident. This specified exact resident behavior is input to the second recording unit 135, where it is recorded and stored temporarily.

Next, the determining unit 132 determines whether the exact resident behavior specified by the specifying unit 131 is identical with the pattern recorded in the first recording unit 130 within a given time period or within a given range of behavior. Then, if the result of this determination is that the exact resident behavior is not identical with the pattern within a given time period or within a given range of behavior, the output unit 133 outputs an alarm.

To take an actual example for the purpose of explanation, it will be assumed, as with embodiment 3, that the resident visits the hospital on the same day each week starting from July 22, and that he/she leaves home at 9 a.m. to go to the hospital. The resident goes to the kitchen 114 at 8 a.m. and prepares breakfast, finishes breakfast at 8:30 a.m., and enters the living room 115. The resident opens and closes the refrigerator 122 intermittently between 8 a.m. and 8:10 a.m., and watches TV 121 for ten minutes from 8:30.

Based on the resident's behavior detected by the CCD camera 101a, etc., and the refrigerator 122 door opening and closing actions detected by the refrigerator door open/close detector 109, the specifying unit 131 specifies the fact that the resident is "eating in the kitchen" from 8 a.m. to 8:30 a.m., and based on the resident's behavior detected by the CCD camera 101b and detection data indicating that the TV 121 power is on detected by the TV power on/off detector 108, specifies the fact that the resident is "watching TV in the living room" from 8:30 to 8:40.

In this case, the determining unit 132 determines that the exact resident behavior specified by the specifying unit 131 is not identical with the pattern recorded in the first recording unit 130. The output unit 133 then outputs an alarm to the PIT 111 and the loudspeaker 113. The output unit 133 transmits the alarm to the PIT 111 by electric wave. When the PIT 111 receives the alarm by electric wave, it emits speech, vibration, and light on the basis of that alarm, notifying the resident of the alarm. The loudspeaker 113 also emits a warning sound. When warned in this way, the resident stops the alarm.

The resident usually visits the hospital on the same day each week starting from July 22, and since the exact behavior on the day of the hospital visit differs from the pattern, it is assumed that the resident wishes to record the exact resident behavior on July 22 in the first recording unit 130 as a new pattern. In this case, the resident inputs an instruction to perform additional recording of the exact behavior of July 22 in the first recording unit 130 as a new pattern. The PIT 111 transmits the instruction received from the resident to the input unit 134 of the management unit 129 by electric wave, and the input unit 134 inputs the resident's instruction transmitted from the PIT 111, and outputs it to the learning unit 136.

Now, since the second recording unit 135 temporarily records the exact resident behavior of July 22 specified by the specifying unit 131, as described above, the exact resident behavior temporarily recorded in the second recording unit 135 is additionally recorded by the learning unit 136 in the first recording unit 130 as part of a new pattern, based on the resident's instruction input by the input unit 134. The learning unit 136 also sequentially records, in the first recording unit 130, the exact resident behavior of July 22 after the input unit 134 has input the resident's instruction, as the remaining part of the new pattern.

As the resident's response to an alarm is input to the input unit 134 in this way, and control is performed so that a new pattern is recorded in the first recording unit 130 on the basis of that response, an alarm is not issued even if the exact resident behavior on July 22 after input of the response by the input unit 134, and the pattern, are not substantially identical, and an alarm is not issued if the resident shows substantially the same behavior as the July 22 behavior after the new pattern has been recorded in the first recording unit 130—or to be exact, from July 23 onward.

The resident's response input by the input unit 134 may be an instruction to record the part of the exact behavior of July 22 from 8 a.m. to 1 p.m. in the first recording unit 130, replacing the part of the pattern from 8 a.m. to 1 p.m. Also, the resident's response input by the input unit 134 may be an instruction to delete the pattern recorded in the first recording unit 130, and record the exact behavior of July 22 in the first recording unit 130 as a new pattern. In any case, the learning unit 136 controls the operation of the first recording unit 130 and the second recording unit 135 on the basis of the response input by the input unit 134.

As explained above, the behavior determining apparatus of embodiment 4 of the present invention outputs an alarm if a pattern recorded beforehand in the first recording unit 130, and the exact behavior of the subject person, are not substantially identical, and the subject person's response to that alarm can be input. Also, based on that response, exact behavior of the subject person that is not substantially identical to the pattern is additionally recorded in the first recording unit 130 as a new pattern, or recorded in the first recording unit 130, replacing some or all of the pattern already recorded in the first recording unit 130.

The first recording unit 130 of the above described embodiment 4 only needs to record one or a plurality of the resident's exact behavior patterns. And the determining unit 132 only needs to determine whether or not any of the one or plurality of patterns recorded by the first recording unit 130 is substantially identical to the exact behavior specified by the specifying unit 131.

Therefore, if the exact behavior of the subject person in a given time period, recorded in the first recording unit 130, is a pattern of lying quietly in bed without music being played, but the subject person is actually in bed with the audio system left on during that time, the specifying unit 131 specifies "in bed with the audio system left on" as the exact behavior of the subject person, and so the exact behavior of the subject person will not be identical to the pattern. In this case an alarm will be issued, but if the subject person went to bed leaving the audio system on in order to sleep deeply, rather than forgetting to turn the audio system off, and, in response to that alarm, wishes to record in the first recording unit 130 exact behavior of sleeping with the audio system left on, and inputs information to that effect to the input unit 134, the exact behavior "sleeping with the audio system left on" will be recorded in the first recording unit 130 as an addition or update.

In the above described embodiment 4, the specifying unit 131 specifies the exact behavior of the subject person based on the detected behavior of the subject person and detected device actions; however, the specifying unit 131 may also specify the exact behavior of the subject person based on the detected behavior of the subject person, detected device actions, and the detected physiological state and/or psychological state of the subject person.

In this case, the pattern recorded in the first recording unit 130 must be a pattern based on the subject person's behavior, device actions, and the subject person's physiological state and/or psychological state. Also, detecting means for detecting the physiological state and/or psychological state of the subject person must be provided. The means for detecting the physiological state and/or psychological state of the subject person was described in embodiment 3, so that description will be omitted here. In this case, too, the determining unit 132 determines whether or not the exact behavior of the subject person specified by the specifying unit 131 is substantially identical to any of the patterns recorded in the first recording unit 130.

Also, some or all of the component elements of the behavior determining apparatus of the above described embodiment 4 may be hardware, or may be software with the same functions as the corresponding functions of that hardware.

The present invention also covers media holding a program and/or data for execution by a computer of some or all of the functions of some or all of the component elements of the above described behavior determining apparatus of embodiment 3 or 4, those media being capable of being processed by a computer.

Media include recording media such as ROM, transmission media such as the Internet, and light, electric-wave, sound-wave, and similar transmission media. Holding media include, for example, recording media on which programs and/or data are recorded, transmission media that transmit programs and/or data, and so forth.

Therefore, the present invention also covers media on which is recorded a program and/or data for execution by a computer of some or all of the functions of some or all of the component elements of the above described behavior determining apparatus of embodiment 3 or 4, those media being capable of being-processed by a computer, and whereby the read above described program and/or data execute the above described functions in collaboration with the above described computer.

"Capable of being processed by a computer" means, in the case of a recording medium such as ROM, for example, capable of being read by a computer, and in the case of a transmission media, that the program and/or data to be transmitted can be handled by a computer as the result of transmission.

The present invention also covers a collection of information comprising programs and/or data for execution by a computer of some or all of the functions of some or all of the component elements of the above described behavior determining apparatus of embodiment 3 or 4.

This "collection of information" includes, for example, software such as programs and/or data.

The data in the above described media and collection of information include data structures, data formats, data types, etc.

(Embodiment 5)

Next, the configuration of a care system according to embodiment 5 of the present invention will be described using FIGS. 7 and 14.

FIG. 7 is a drawing for explaining the location of each component unit when the several component units configuring the behavior determining apparatus of the above described embodiment 3 are installed in various locations in a residence, etc. As explained later, some of the component units configuring the care system of embodiment 5 are the same as some of the component units configuring the behavior determining apparatus of embodiment 3, and therefore FIG. 7 will also be used when describing the care system of embodiment 5. FIG. 14 is a block diagram of the care system of embodiment 5 of the present invention.

Figure 14:
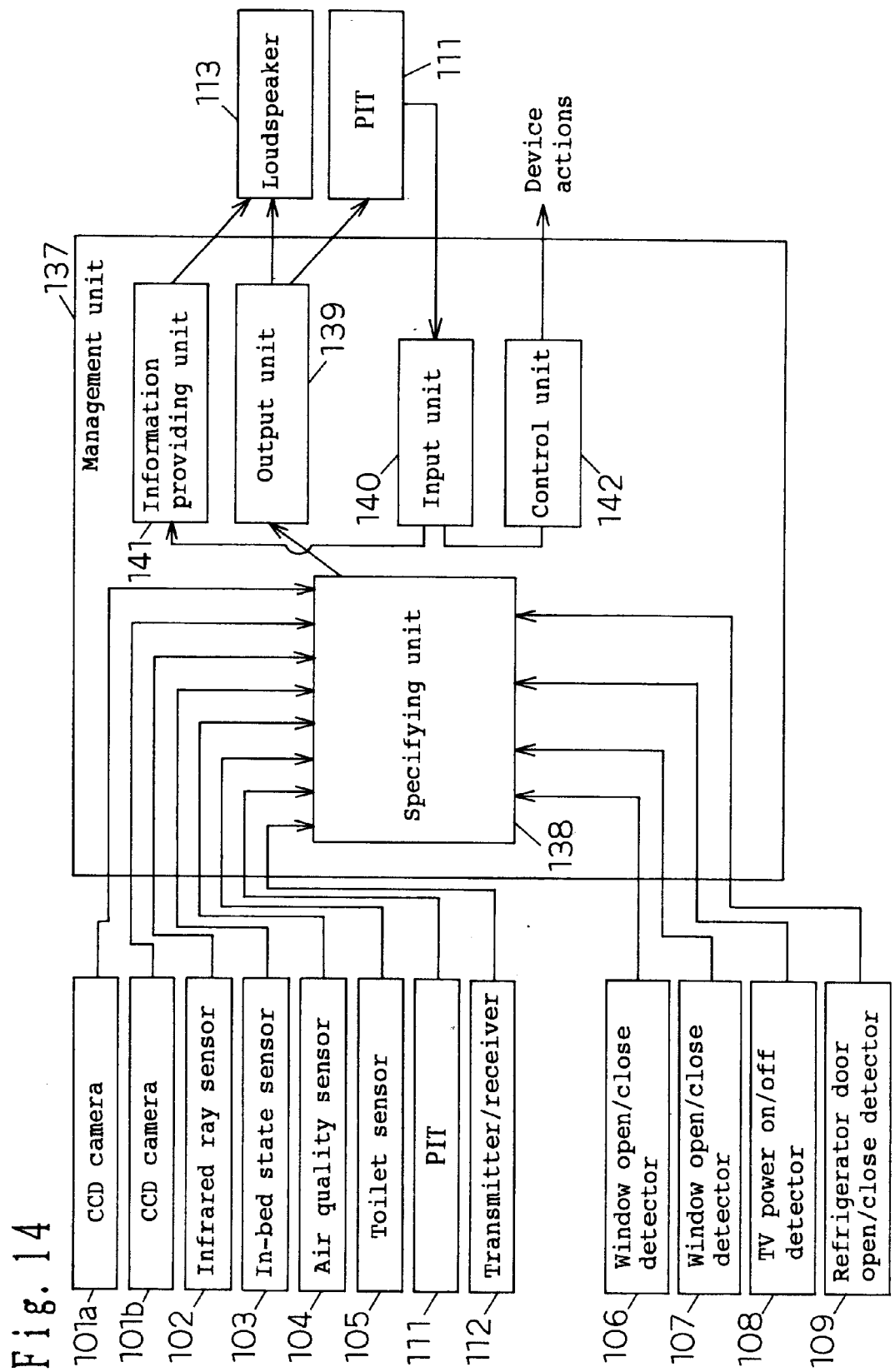
FIG. 14 is a block diagram of the care system of embodiment 5 of the present invention.

As shown in FIG. 14, the care system of embodiment 5 of the present invention is configured by CCD cameras 101a and 101b, an infrared ray sensor 102, an in-bed state sensor 103, an air quality sensor 104, a toilet sensor 105, window open/close detectors 106 and 107, a TV power on/off detector 108, a refrigerator door open/close detector 109, a management unit 137, a PIT 111, a transmitter/receiver 112, and a loudspeaker 113. The CCD cameras 101a and 101b, infrared ray sensor 102, in-bed state sensor 103, air quality sensor 104, toilet sensor 105, window open/close detectors 106 and 107, TV power on/off detector 108, refrigerator door open/close detector 109, PIT 111, transmitter/receiver 112, and loudspeaker 113 are the same as the relevant component units configuring the behavior determining apparatus of embodiment 3 described using FIGS. 7 and 8.

The management unit 137 is installed within a wall of the living room 115 in FIG. 3, in the same way as the management unit 110 of the behavior determining apparatus of embodiment 3, and, as shown in FIG. 14, is configured by an specifying unit 138, an output unit 139, an input unit 140, an information providing unit 141, and a control unit 142.

The specifying unit 138 is means for specifying the exact behavior of the-resident on the basis of detected resident behavior and detected device actions. The behavior of the resident is detected by means of the CCD cameras 101a and 101b, infrared ray sensor 102, in-bed state sensor 103, air quality sensor 104, toilet sensor 105, and PIT 111, and information, etc., received by the transmitter/receiver 112 is also used for resident behavior detection. Device actions, on the other hand, mean opening and closing actions for the windows 119 and 120 provided in the bedroom 116 and living room 115 in FIG. 7, power on/off actions for the TV 121 located in the living room 115, and opening and closing actions for the door of the refrigerator 122 located in the kitchen 114, and these actions are detected, respectively, by the window open/close detector 106, window open/close detector 107, TV power on/off detector 108, and refrigerator door open/close detector 109.

The output unit 139 is means for outputting the exact behavior of the resident specified by the specifying unit 138. The input unit 140 is means for inputting the resident's response to information output by the output unit 139. The information providing unit 141 has many items of information relating to the care of the resident set, and is means for selecting one or a plurality of information items from the many information items set, on the basis of the resident's responses input to the input unit 140, and providing that selected information. This selected information is output from the loudspeaker 113. An actual example of care-related information will be described when the operation of the care system of embodiment 5 is explained later. The control unit 142 is means for-controlling the operation of devices located in the resident's residence on the basis of the resident's responses input to the input unit 140, and is connected by cables to the devices subject to control. In embodiment 5, the window 120 provided in the living room 115 is used as an example of a device subject to control.

In embodiment 5, the CCD cameras 101a and 101b, infrared ray sensor 102, in-bed state sensor 103, air quality sensor 104, toilet sensor 105, PIT 111, and transmitter/receiver 112 are used as an example of the first detecting means of the care systems according to claim 35 or 36. Also, in embodiment 5, the window open/close detectors 106 and 107, TV power on/off detector 108, and refrigerator door open/close detector 109 are used as an example of the second detecting means of the care system according to claim 35 or 36.

In embodiment 5, the specifying unit 138 within the management unit 137 is used as an example of the specifying means, and the output unit 139 within the management unit 137, PIT 111, loudspeaker 113 are used as an example of the notifying means, and the input unit 140 is used as an example of the input means, respectively, of the care system according to claim 35 or 36.

In embodiment 5, the information providing unit 141 within the management unit 137 is used as an example of the information providing means of the care system according to claim 35, and the control unit 142 within the management unit 137 is used as an example of the control means of the care system according to claim 36.

Next, the operation of the care system according to embodiment 5 of the present invention will be described.

As described in embodiment 3, the CCD cameras 101a and 101b, infrared ray sensor 102, in-bed state sensor 103, air quality sensor 104, toilet sensor 105, and PIT 111 detect the behavior of the subject resident, and output the various detection data to the specifying unit 138 within the management unit 137. Also, as described in embodiment 3, the transmitter/receiver 112 outputs information on the person carrying the specified PIT 111 to the specifying unit 138. The window open/close detectors 106 and 107, TV power on/off detector 108, and refrigerator door open/close detector 109 detect, respectively, window 119 and 120 opening and closing actions, TV 121 power on/off actions, and refrigerator 122 door opening and closing actions, and output the respective detection data to the specifying unit 138.

The specifying unit 138 specifies the exact behavior of the resident on the basis of the input resident behavior detection data and device action detection data. For example, if the resident is detected to be in the living room 115 for a long time by the CCD camera 101b, and during the time in which that resident is detected to be in the living room 115, the power of the TV 121 is detected to be on by the TV power on/off detector 108, the specifying unit 138 specifies the fact that the resident has been watching TV for a long time in the living room 115.

The output unit 139 outputs the exact behavior of the resident, specified by the specifying unit 138, to the PIT 111 and loudspeaker 113. The output unit 139 transmits information to the PIT 111 by electric wave. When the PIT 111 receives information by electric wave, it outputs the exact resident behavior in speech form, based on that information. The loudspeaker 113, also, outputs the exact resident behavior in speech form, based on information from the output unit 139. To be specific, information to the effect that the resident "has been watching the TV 121 in the living room 115 for a long time" is output from the PIT 111 and loudspeaker 113.

When exact resident behavior is output from the PIT 111 and loudspeaker 113 in this way, that resident can respond to the information output from the PIT 111 and loudspeaker 113, and that response is input to the PIT 111. The PIT 111 transmits the response received from the resident to the input unit 140 within the management unit 137 by electric wave, and the input unit 140 inputs the resident's response transmitted from the PIT 111, and outputs it to the information providing unit 141 and control unit 142. The information providing unit 141 then performs information provision on the basis of the resident's response, and the control unit 142 controls device actions on the basis of the resident's response.

If, for example, the resident has been watching the TV 121 for a long time and wants to take some kind of exercise, and the resident's response is a query as to what kind of exercise should be taken, the information providing unit 141 will provide an exercise menu on the basis of that response. This exercise menu is output from the loudspeaker 113. Information to be provided is set in the information providing unit 141, and an example of this set information is an exercise menu. There may be, for example, a plurality of exercise menus applicable to the case where the resident has not taken any exercise for a long time, and if the resident's response includes information on the length of time for which exercise has not been taken, the information providing unit 141 will select a suitable menu from among a plurality of menus, on the basis of that length of time without taking exercise, and provide that menu.

And if, for example, the resident has been watching the TV 121 for a long time and decides that the ventilation of the living room 115 is inadequate, and the resident's response is to effect control so that the window 120 is opened for ten minutes, the control unit 142 will control window 120 opening/closing actions so that the window 120 is opened for ten minutes. If the resident's response is a request to have cheerful music played and to have sunlight let into the living room 115, the control unit 142 will control audio system and curtain opening/closing actions.

If the resident does not respond, the exact resident behavior specified by the specifying unit 138 can be notified to family members, etc., living apart from the resident, by means of a loudspeaker in the resident's residence or in a residence other than that of the resident, connected via a telephone line, etc., to the care system of embodiment 5.

In the above described embodiment 5, the care system of the present invention has been described taking the example of the case where the specifying unit 138 specifies the fact that the resident has been watching the TV 121 in the living room 115 for a long time, on the basis of input resident behavior detection data and device action detection data. The specifying means of the care system of the present invention is means for specifying the exact behavior of the resident, on the basis of input resident behavior detection data and device action detection data, in this way.

If, for example, the specifying unit 138 specifies the fact that the audio system is on when the resident has gone to bed, information to that effect is notified; and if the resident's response to that information is a request for the audio system volume to be gradually reduced and for the audio system to be turned off after 30 minutes, the control unit 142 will control the operation of the audio system on the basis of that response. If the resident does not respond, the control unit 142 could also turn the audio system off immediately.

And if, for example, the specifying unit 138 specifies the fact that 8 hours has elapsed since the resident went to bed, and it is time for the resident to get up, information to that effect is notified; and if the resident's response to that notification is for the curtains to be opened, the control unit 142 will open the closed curtains on the basis of that response. If, on the other hand, the resident still feels sleepy and gives a response for the curtain opening time to be put back by 30 minutes, the control unit 142 will open the closed curtains after the elapse of the requested 30 minutes, on the basis of that response. And if, for example, the resident has a headache and feels unwell, and gives a response to have that fact notified to a resident other than the subject resident, or to family members, for instance, by means of a loudspeaker installed in the residence of those family members, the control unit 142 will notify information to the effect that the resident is unwell, on the basis of that response.

Also, if, for example, the specifying unit 138 specifies the fact that the resident is almost motionless in the toilet, information to that effect is notified. If this kind of situation occurs a given number of times, and in each case the resident responds to the notification by indicating that there is nothing wrong, it would also be possible for the specifying unit 138, from the next time on, to notify the relevant information only if the resident is almost motionless in the toilet for longer than a given time.

Also, if, for example, the specifying unit 138 specifies the fact that the resident is napping on the sofa, information to that effect, or information to that effect and the information "You will catch cold," is notified, and the resident gives a response indicating "Understood" to that notification, or if the indoor environment has not changed but the resident responds with a request to have the lights turned down, the control unit 142 will turn down the room lights on the basis of that response. And if it is notified that the resident is napping on the sofa, and a response requesting that the lights be turned down is received more than a given number of times, the lights could be turned down, from the next time on, when the resident is specified as napping on the sofa, without issuing a notification to that effect.

Thus far, it has been assumed that the specifying unit 138 specifies the exact behavior of the resident on the basis of input resident behavior detection data and device action detection data, but it is also possible for detection data whereby the physiological state and/or psychological state of the resident are specified also to be input, and the behavior of the resident to be accurately specified. In this case, a third detecting means is necessary to enable the physiological state and/or psychological state of the resident to be specified, and the detecting means for detecting the physiological state and/or psychological state of the resident described in embodiment 3 can be used as this third detecting means.

If the specifying unit 138 finds, for example, that the resident tends to stay indoors and, according to the results of psychological tests, is found to suffer from mental stress, information to this effect is notified, and if the resident responds to this notification with a response for having the operation of the audio system controlled to output soothing music, or a response for performing control in order to increase the indoor negative ion count, the control unit 142 will control the operation of the stereo set, or perform air conditioner control, on the basis of that response.

Some or all of the component elements of the above described care system of embodiment 5 may be hardware, or may be software with the same functions as the corresponding functions of that hardware.

The present invention also covers a care residence comprising the above described care system of embodiment 5.

The present invention also covers media holding a program and/or data for execution by a computer of some or all of the functions of some or all of the component elements of the above described care system of embodiment 5, those media being capable of being processed by a computer.

Media include recording media such as ROM, transmission media such as the Internet, and light, electric-wave, sound-wave, and similar transmission media. Holding media include, for example, recording media on which programs and/or data are recorded, transmission media that transmit programs and/or data, and so forth.

Therefore, the present invention also covers media on which is recorded a program and/or data for execution by a computer of some or all of the functions of some or all of the component elements of the above described care system of embodiment 5, those media being capable of being processed by a computer, and whereby the read above described program and/or data execute the above described functions in collaboration with the above described computer.

"Capable of being processed by a computer" means, in the case of a recording medium such as ROM, for example, capable of being read by a computer, and in the case of a transmission media, that the program and/or data to be transmitted can be handled by a computer as the result of transmission.

The present invention also covers a collection of information comprising programs and/or data for execution by a computer of some or all of the functions of some or all of the component elements of the above described care system of embodiment 5.

This "collection of information" includes, for example, software such as programs and/or data.

The data in the above described media and information collection system include data structures, data formats, data types, etc.

(Embodiment 6)

Figure 15:
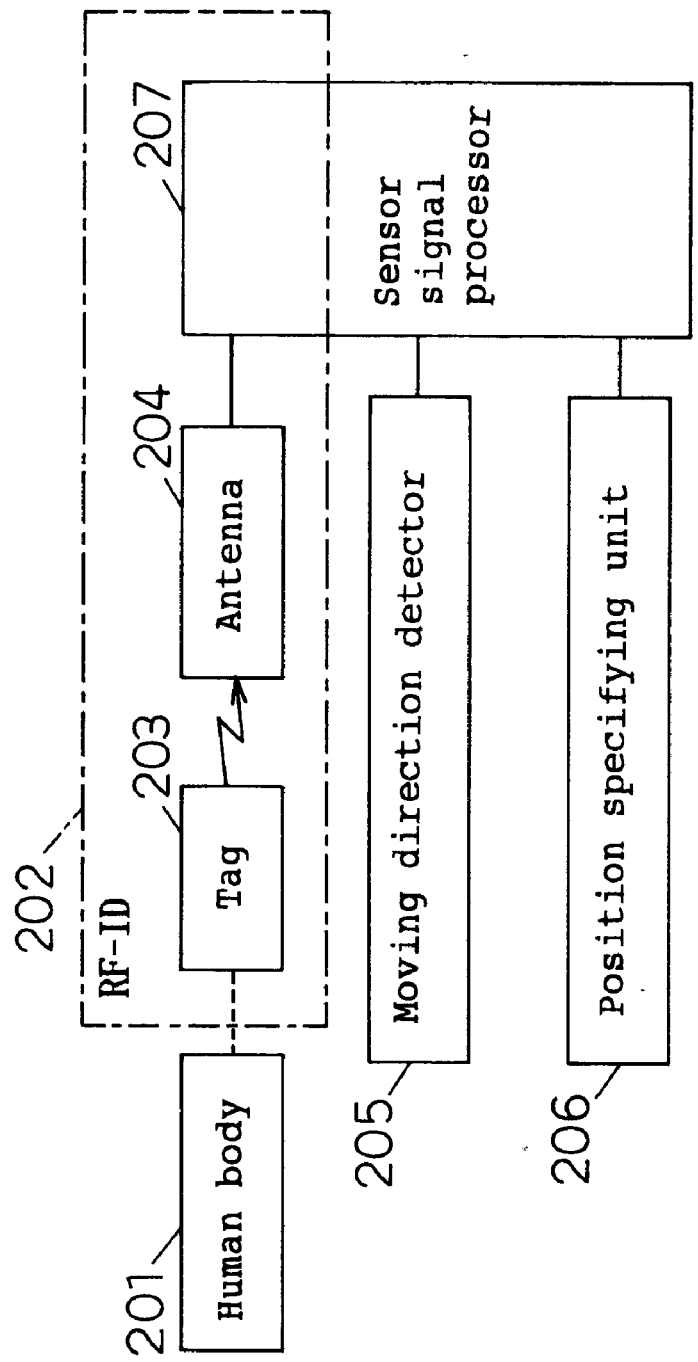
FIG. 15 is an outline type drawing of the behavior information specifying apparatus in embodiment 6 of the present invention.

Next, the configuration of a behavior information specifying apparatus according to embodiment 6 will be described with reference to the drawings. FIG. 15 is an outline configuration diagram of the behavior information specifying apparatus in one embodiment of the present invention. This embodiment is configured by an RF-ID 202, moving direction detector 205, and position specifying unit 206, as sensors.

The RF-ID 202 is configured by a tag 203 attached to a human body 201, an antenna 204 that receives an electric wave of a specific frequency transmitted from that tag 203, and a sensor signal processor 207 that processes signals obtained from the tag 203.

The moving direction detector 205 is a device that uses infrared ray sensors, distance sensors, etc., and performs sensor output according to the direction of motion of a human body or in animate object, processes sensor signals output from the moving direction detector 205 by means of the sensor signal processor 207, and determines the direction of movement—entering or leaving a room—of a human body or inanimate object.

The position specifying unit 206 is a device that specifies the position of a human body or inanimate object by means of image extraction from a CCD camera, an infrared ray sensor capable of measuring two-dimensional temperature distribution, or an infrared camera, or from the intensity and direction of an electric wave from an electric wave generator attached to a human body or inanimate object, using one or more antennas installed indoors, and that processes signals obtained from the antenna by means of the sensor signal processor 207, and can calculate two-dimensional coordinates on an indoor floor.

The operation in this embodiment will be described below. The RF-ID antenna 204 and moving direction detector 205 are installed near an entrance/exit, and the position specifying unit 206 is installed in the room. The antenna 204 of the RF-ID 202 is in a state of constant standby for reception of electric waves from the tag 203. When a human body with a tag 203 attached to some part approaches the entrance/exit, the antenna 204 receives the specific frequency of the tag 203. This is the provisional specification state.

Next, when the human body moves from outside the room to inside the room, the moving direction detector 205 detects the movement of the human body, and the full specification state is established when the human body has completely entered the room. After specification is completed, the positions of the human body and inanimate objects are specified using the position specifying unit 206. Processing for collecting and determining these signals is performed by the sensor signal processor 207.

(Embodiment 7)

Figure 16:
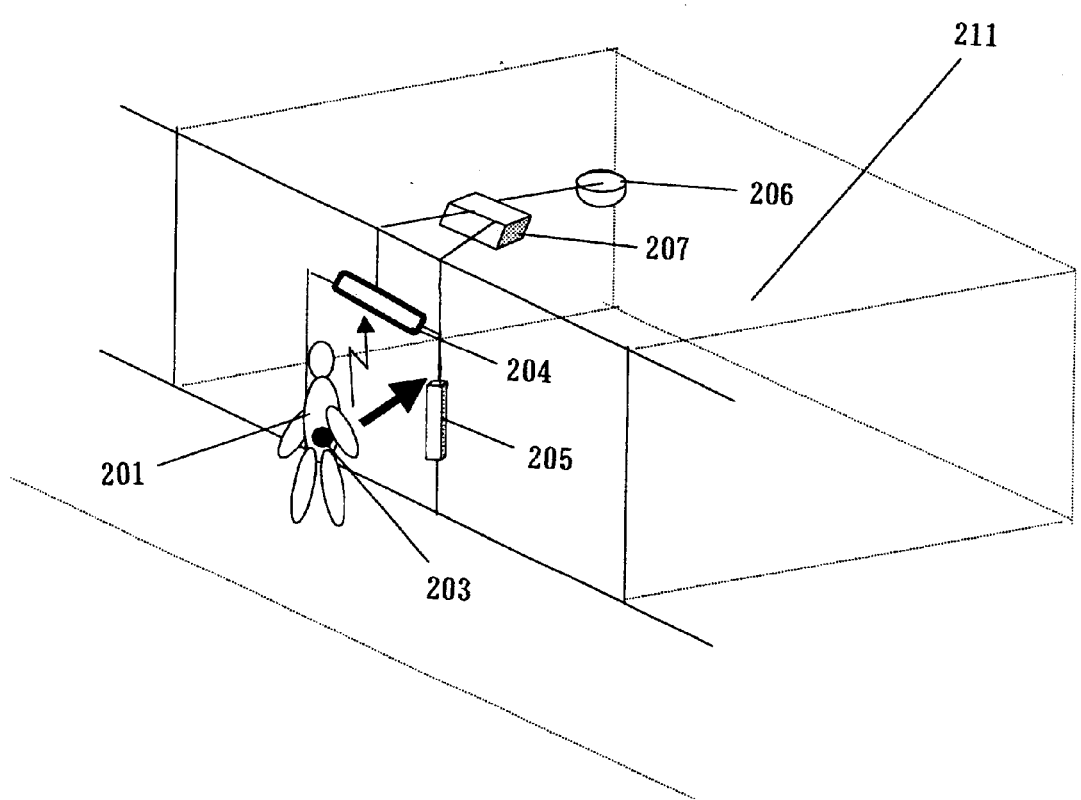
FIG. 16 is an outline type drawing of the behavior information specifying apparatus in embodiment 7 of the present invention.
Figure 17:
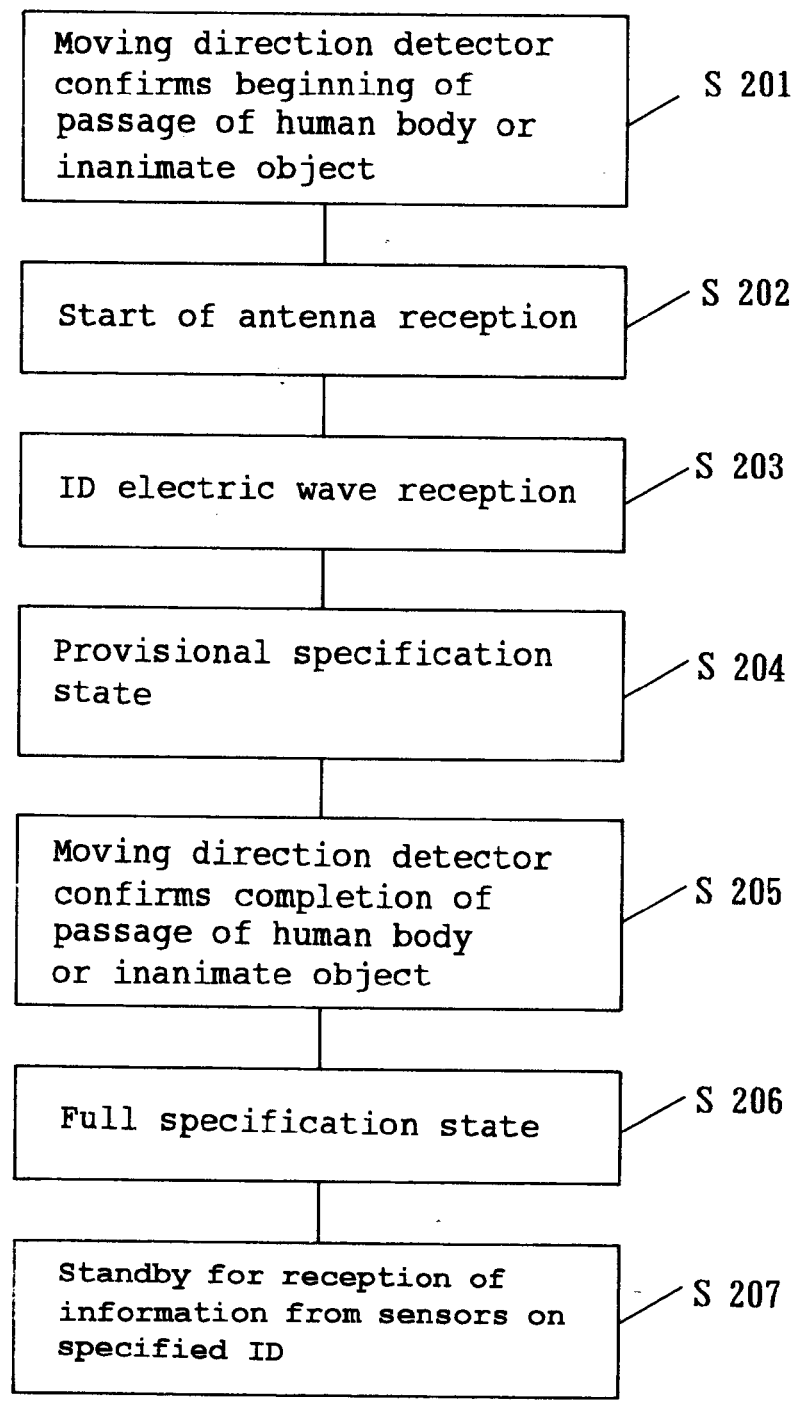
FIG. 17 is a drawing showing the ID specification procedure using the moving direction detector in embodiment 7 of the present invention.

Next, the configuration of a behavior information specifying apparatus according to embodiment 7 will be described with reference to the drawings. FIG. 16 shows an outline type drawing of the behavior information specifying apparatus in one embodiment of the present invention. FIG. 17 shows the ID specification procedure using the moving direction detector in one embodiment of the present invention. The operation and method in this embodiment will be described below for the case where a human body moves from a passageway into a room.

In FIG. 16, a human body 201 is about to enter a room carrying a tag 203 on part of the body. As the entrance/exit is approached, the moving direction detector 205 detects the human body, and confirms the beginning of passage through the entrance/exit (S201). At this point, the RF-ID antenna 204 starts receiving the specific frequency of the tag 203 (S202). If entry into the room is continued further, the tag 203 advances into the reception range of the antenna 204, and so the ID electric wave is received (S203). This is the provisional specification state (S204).

If entry into the room is continued further, and the moving direction detector 205 confirms that passage through the entrance/exit has been completed (S205), the full specification state is established (S206), after which, unless the room is exited, a standby state is established for information reception from each sensor for the specified ID (S207). Here, the position specifying unit 206 performs human body and inanimate object position specification for the number of specified IDs.

If movement is made from the provisional specification state to the passageway without entering the room, for example, since the moving direction detector 205 has not confirmed completion of passage, the full specification state will not be entered.

On the other hand, the procedure is also as described above when a human body 201 leaves the room. First, as the entrance/exit is approached, the moving direction detector 205 detects the human body, and confirms the beginning of passage through the entrance/exit. At this point, the RF-ID antenna 204 starts receiving the specific frequency of the tag 203. Also, if egress from the room is continued further, the tag 203 advances into the reception range of the antenna 204, and so the ID electric wave is received. This is the provisional specification state. If egress from the room is continued further, and the moving direction detector 205 confirms that passage through the entrance/exit has been completed, the full specification state is established, after which, unless the room is entered, information reception from each sensor for the specified ID is canceled. Since there is no specified ID, the position specifying unit 206 does not perform position specification.

(Embodiment 8)

Figure 18:
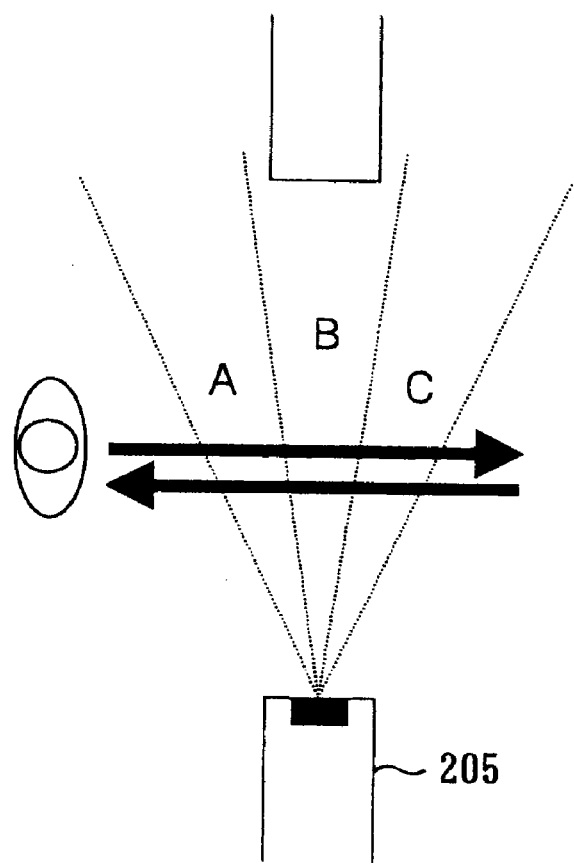
FIG. 18 is a drawing showing the installation position and detection area of the moving direction detector in the behavior information specifying apparatus in embodiment 8 of the present invention.

Next, the operation of the moving direction detector 205 in a behavior information specifying apparatus according to embodiment 8 will be described with reference to the drawings. FIG. 18 shows the installation position and detection area of the moving direction detector 205 in the behavior information specifying apparatus in one embodiment of the present invention, viewed from ceiling to floor.

The moving direction detector 205 is installed in the end of one wall. An infrared ray sensor is used as the moving direction detector 205 in this embodiment, configured so that the three zones A, B, and C in the drawing are simultaneously detected by the respective elements. As this sensor outputs sensor output corresponding to the radiant temperature of the detected body, the sensor output is given a binary characteristic by means of a threshold value to distinguish between the presence of a human body within the sensor's detection range and the state in which nothing is present (background).

FIG. 19 shows an example of motion detection by the moving direction detector 205. In FIG. 19, the squares are binary results, with black indicating the presence of a human body and white indicating the background. The horizontal direction shows the direction of the sensor detection areas, and the vertical direction shows the flow of time.

The method of detecting the passage of a human body in this embodiment will be described below. When a human body begins to enter a room from outside, in the same way as described in embodiment 7, the body passes through sensor detection areas A, B, and C, in that order, so that the time-series data resulting from binary processing of the sensor output is as shown in FIG. 19(1). When a human body moves from inside the room to outside the room, on the other hand, the body passes through sensor detection areas C, B, and A, in that order, so that the time-series data resulting from binary processing of the sensor output is as shown in FIG. 19(2).

FIG. 19(3) shows the case where a human body begins to move from outside to inside the room, passing from area A into area B, and arriving beneath the antenna 204, but does not enter the room. In this case, since the body does not enter area C, the provisional specification state is held, and the full specification state is not established. If the hold time for the provisional specification state is set beforehand, the provisional specification state will also be cleared.

FIG. 19(4) shows the case where a human body stops near the entrance/exit; in this case, too, the provisional specification state is established, as described before, but the full specification state is not. Also—although a drawing is not used for the description here—for cases where two or more persons enter a room in succession, for example, accuracy can be improved by making the detection areas narrower. And cases where two persons leave the room simultaneously, or where the entrance/exit is wide, can be handled by installing a plurality of sensors.

By using an infrared ray sensor for the moving direction detector in this way, entry into and egress from a room can be accurately specified, and the RF-ID tag reception timing can also be pinpointed with extreme accuracy, enabling greater specification accuracy to be achieved. Here, an example of an infrared ray sensor has been given, but this is not a limitation, and in cases where a sensor employing light or ultrasonic waves is used, also, similar results can be obtained by binary representation of the presence or non-presence of a human body.

(Embodiment 9)

Figure 20:
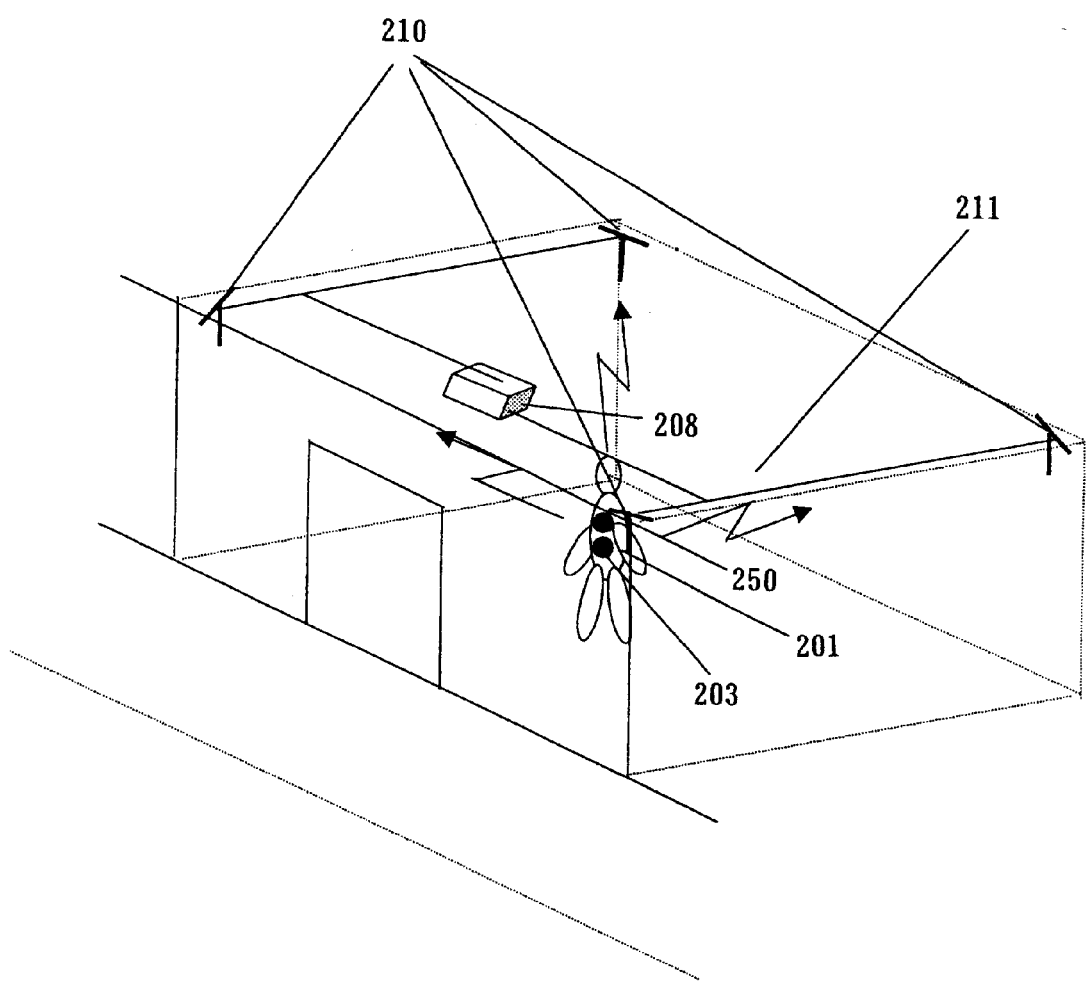
FIG. 20 shows an outline type drawing of the behavior information specifying apparatus in embodiment 9 of the present invention.

Next, a behavior information specifying apparatus according to embodiment 9 will be described with reference to the drawings. FIG. 20 shows an outline type drawing of the behavior information specifying apparatus in one embodiment of the present invention. Inside the room, antennas for measuring electric wave intensity 210 which receive an electric wave of a specific frequency are installed in the four corners of the room, and these are connected to an electric wave intensity analyzer 208.

A personal portable terminal 250 is attached to part of a human body 201. When the human body 201 enters the room, a transmitter incorporated in the personal portable terminal 250 transmits an electric wave of a specific frequency. This electric wave is received by the antennas for measuring electric wave intensity 210, the intensity ratio of this electric wave is analyzed by the electric wave intensity analyzer 208, and the position of the human body 201 in the room is calculated.

(Embodiment 10)

The actual human body position specification method of the behavior information specifying apparatus described in embodiment 9 will now be described with reference to the drawings. Two examples will be described for this embodiment.

FIG. 21 shows measurement example 1 regarding the human body position specification method. The upper drawing in FIG. 21 shows a room viewed from above. The antenna 210 installed at the top of corner A of the room can measure electric wave intensity and directivity, and with regard to electric wave directivity, can measure ±x degrees. An example of the measurement of the intensity and directivity of an electric wave of a specific frequency transmitted from the transmitter incorporated in the personal portable terminal 250 described in embodiment 9 is shown in the lower drawing in FIG. 21. As there is a correlation between the electric wave intensity and the distance between the antenna and the transmitter, in this measurement example, from the peak value of the electric wave intensity and the directivity angle, it appears that a human body is present at the position indicated by a star shown in the upper part of FIG. 21. In this measurement example, the antenna 210 must be provided with a function for measuring the directivity of the electric wave, which involves a certain cost.

Figure 22:
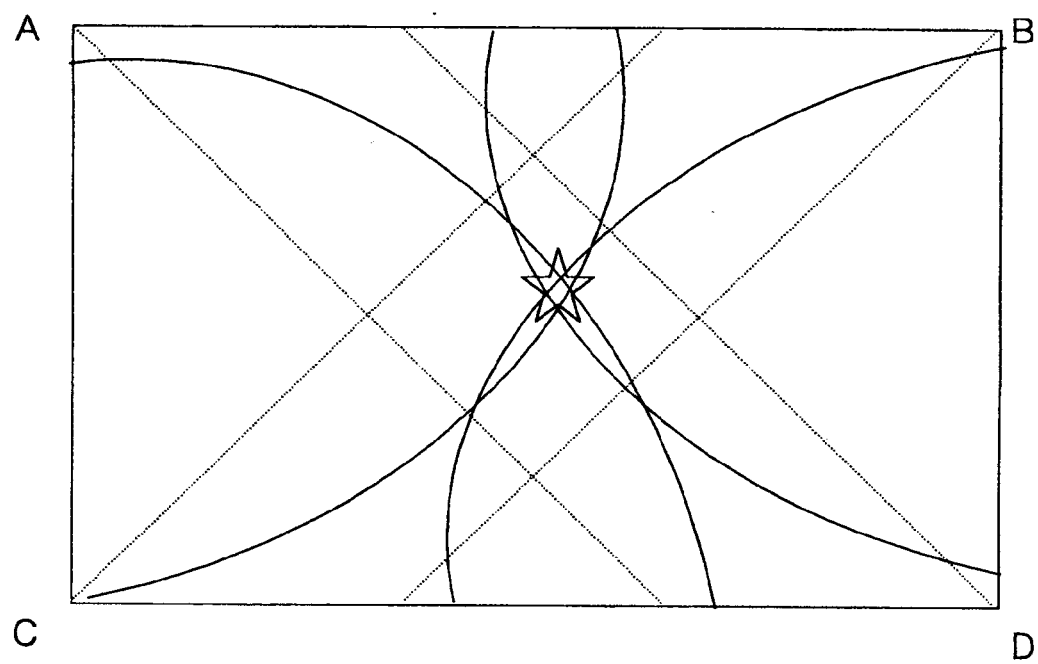
FIG. 22 shows a measurement example regarding the human body position specification method in embodiment 10 of the present invention.

A position specification method will now be described in which electric wave intensity is measured using a plurality of antennas. FIG. 22 shows this measurement example 2. In this measurement example, the intensity of the electric wave of a specific frequency transmitted from the transmitter incorporated in the personal portable terminal 250 is measured by antennas installed at the top of room corners A, B, C, and D. The reception intensity of the electric wave received by each antenna enables the distance from the respective corner to be calculated, based on the correlation between the electric wave intensity found beforehand and the distance between the antenna and the transmitter. The place where circles drawn with the respective corners as their centers overlap is the position of the transmitter, and in the measurement example it appears that a human body is present at the position indicated by a star.

In the two examples above, the cases of one antenna and four antennas are described, but the number of antennas is not limited to these numbers. Also, it goes without saying that the accuracy of position specification can be improved by increasing the number of antennas.

(Embodiment 11)

The position specifying unit in the behavior information specifying apparatus according to embodiment 11 will now be described with reference to the drawings. FIG. 23 shows outline type drawings relating to the position specifying unit using a two-dimensional infrared ray sensor in the behavior information specifying apparatus in one embodiment of the present invention.

The field of view of the infrared ray sensor attached to the ceiling is shown viewed from the side in the upper drawing in FIG. 23, and viewed from above in the lower drawing. A chopper is fitted to the front of a pyro-electric one-dimensional array element provided with a plurality of photo-receptors, and when the rotated in the circumferential direction shown in the lower drawing in FIG. 23, the field of view is also divided in the circumferential direction according to the chopping timing, and it is possible to measure the two-dimensional temperature distribution within the room as shown in the drawing. In this implementation example, there are six photo-receptors, and so there are six divisions in the radial direction and 24 divisions in the circumferential direction. Since the temperature of the measured body can easily be calculated on the basis of the chopper temperature, it is possible to set a suitable sensor output threshold and extract the area in which a human body is present. Also, since the apparent size of a human body is determined by the distance from the sensor, it is possible to distinguish between the area of the temperature in the vicinity of a human body, and the area of a human body, and to increase the accuracy of human body extraction.

By means of the above method, it is possible to find the position at which a human body is present in a room as on-floor coordinates. This method is not limited to the case where a two-dimensional infrared ray sensor is used; it is possible to extract a human body area in the same way, and obtain similar results, by dividing a thermal image obtained from a two-dimensional infrared camera.

As opposed to the above described case, in which the two-dimensional temperature distribution is measured using an infrared ray sensor, and a human body extracted, a method will now be described for measuring a visible image using a CCD camera, and extracting a human body. (Drawings are not used in this description.) A plurality of CCD cameras are installed in the upper part of a room, with a field of view in the direction of the floor, and a visible image is measured. Extraction of a human body area is performed using a method such as moving body contour extraction or facial skin color extraction. Also, since the apparent size of a human body is determined by the distance from the cameras, the accuracy of human body extraction can be increased. Correlational data for positions within the field of view of the cameras and actual on-floor positions can be measured or found by calculation beforehand, and the actual position at which a human body is present can be found from a human body image extracted within the field of view of the cameras.

(Embodiment 12)

Figure 24:
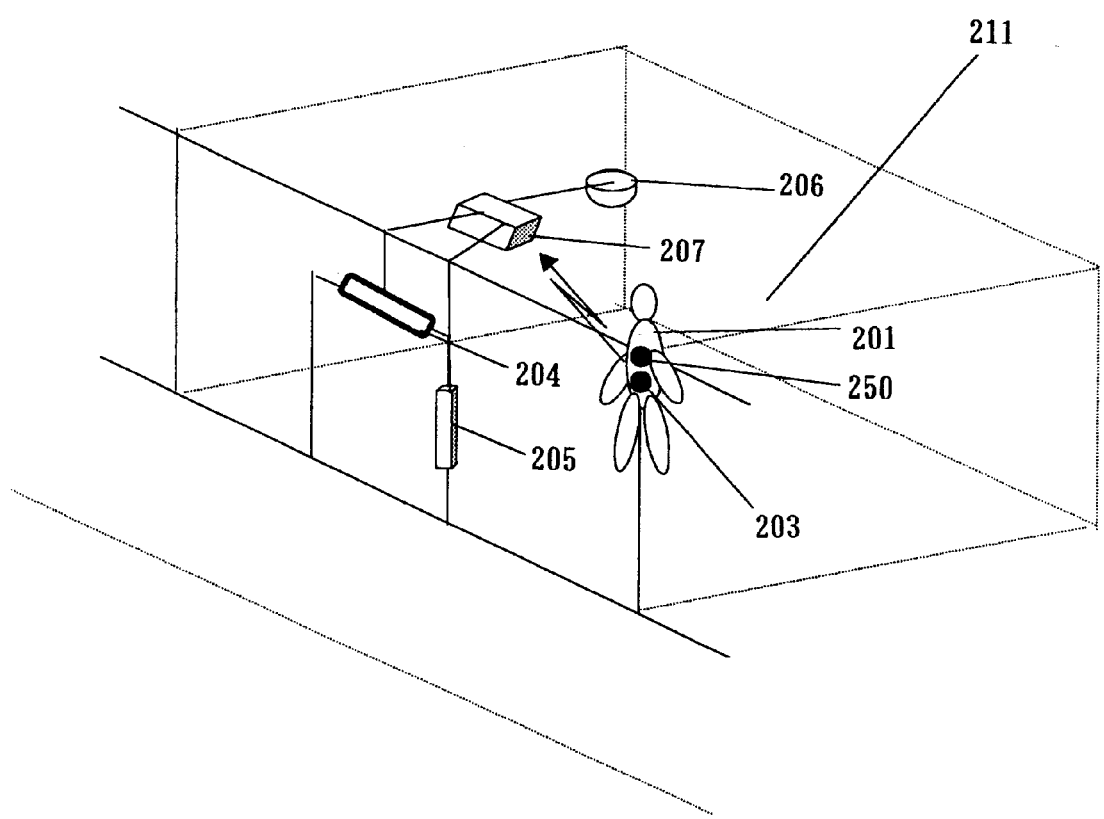
FIG. 24 shows an outline type drawing of the behavior information specifying apparatus in embodiment 12 of the present invention.

The position specifying unit in the behavior information specifying apparatus according to embodiment 12 will now be described with reference to the drawings. FIG. 24 shows an outline type drawing of the behavior information specifying apparatus in one embodiment of the present invention. At the entrance/exit, a human body 201 for which entry into the room has been confirmed by the moving direction detector 205 undergoes ID detection by the antenna 204 of the RF-ID 202. After entry into the room, position specification is performed by the position specifying unit 206, at which time the ID information and position information are aggregated in the sensor signal processor 207, enabling information as to "who" is "where" to be obtained.

In case of a plurality of persons, also, by changing the specific frequency from the personal portable terminal 250 described in embodiment 10 for individual persons, it is possible to obtain the respective human body position information effectively. Since ID specification is performed at the entrance/exit in both case of a single person and the case of a plurality of persons, even if the electric wave transmitted by a personal portable terminal 250 should happen to be received by a unit in the next room, since ID specification has not been performed in the next room, incorrect detection will never occur.

(Embodiment 13)

Figure 25:
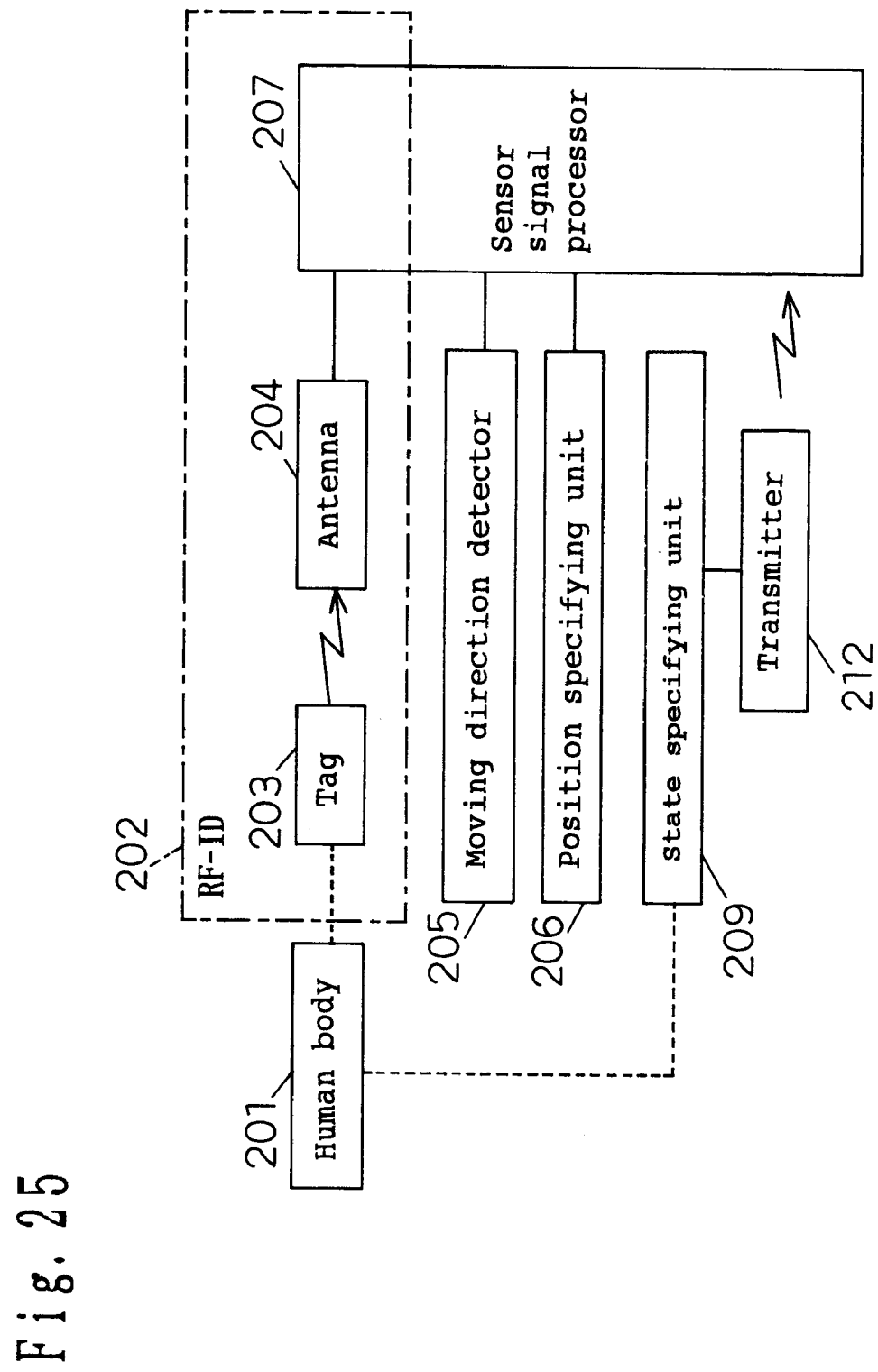
FIG. 25 shows an outline type drawing of the behavior information specifying apparatus in embodiment 13 of the present invention.

The state specifying unit in the behavior information specifying apparatus according to embodiment 13 will now be described with reference to the drawings. FIG. 25 shows an outline type drawing of the behavior information specifying apparatus in one embodiment of the present invention.

The state specifying unit 209 in the personal portable terminal 250 attached to a human body 201 is configured by one or more sensors, measures information on the state of the human body-such as attitude, walking condition (walking horizontally, climbing stairs, descending stairs), activity state (resting, normal activity, vigorous activity), and physiological state (heart rate, blood pressure, body temperature, perspiration)-and transmits this to the sensor signal processor 207 via a transmitter 212.

In this implementation example, there are no particular restrictions on the place where sensor output is analyzed. That is to say, it is possible to complete sensor output analysis by the state specifying unit 209 in the personal portable terminal 250 and obtain various kinds of human body state information, or it is possible for sensor raw output to be transmitted first to the sensor signal processor 207 from the transmitter 212, and then for analysis to be performed by the sensor signal processor 207, and various kinds of human body state information to be obtained. Moreover, the state specifying unit 209 and the transmitter 212 may be incorporated in the above described personal portable terminal 250.

(Embodiment 14)

The state specifying unit in the behavior information specifying apparatus according to embodiment 14 will now be described. In this embodiment, the state specifying unit 209 in the personal portable terminal 250 and transmitter 212 are incorporated in the personal portable terminal 250. In the same way as described in embodiment 12, at the entrance/exit a human body 201 that has undergone ID detection by the RF-ID 202 and moving direction detector 205 is confirmed to have entered the room.

After entry into the room, human body state detection is performed by the state specifying unit 209, and that information is transmitted to the sensor signal processor 207. At this time, ID information is also communicated to the sensor signal processor 207, and information exchange is performed, enabling information as to "who" is doing "what" "where" to be obtained.

In case of a plurality of persons, also, by changing the specific frequency from the personal portable terminal 250 described in embodiment 10 for individual persons, it is possible to obtain the respective human body position information effectively, and it is also possible to add individual state information.

Since ID specification is performed at the entrance/exit in both case of a single person and case of a plurality of persons, even if the electric wave transmitted from the transmitter should happen to be received by a unit in the next room, since ID specification has not been performed in the next room, incorrect detection will never occur.

(Embodiment 15)

Figure 26:
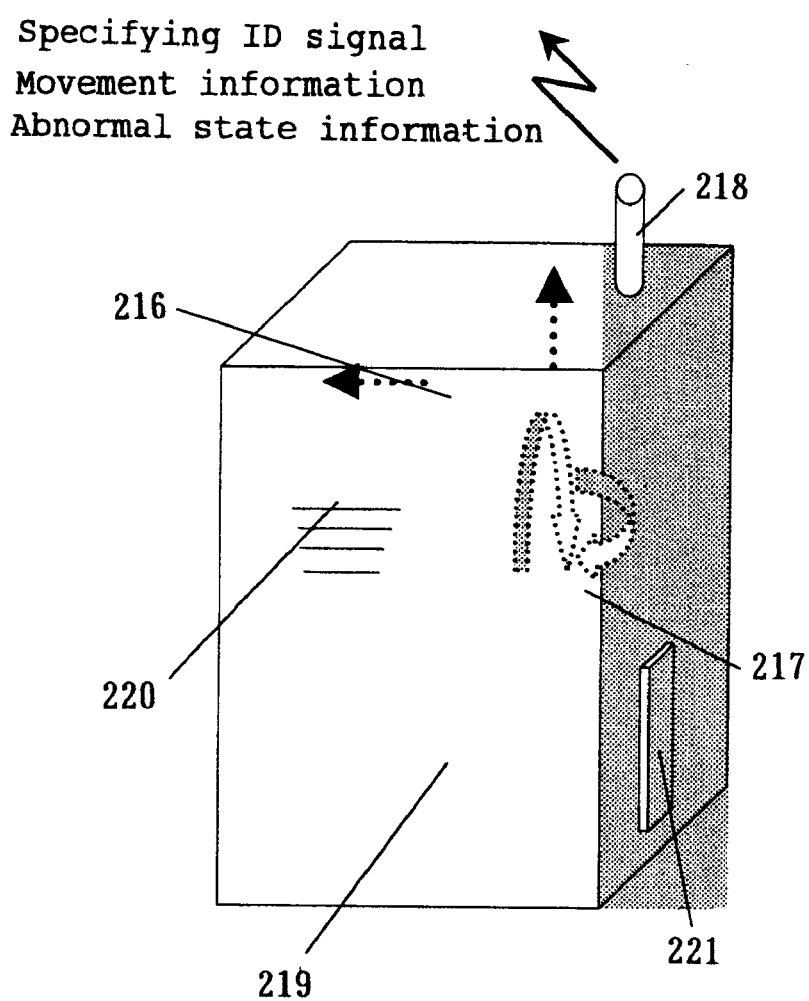
FIG. 26 shows an outline type drawing of the state specifying unit in embodiment 15 of the present invention.

The state specifying unit in the behavior information specifying apparatus according to embodiment 15 will now be described with reference to the drawings. FIG. 26 shows an outline type drawing of the state specifying unit in one embodiment of the present invention.

This device is fixed to a part of the body using a belt around the waist, etc. In this embodiment, the attitude, walking condition, line of movement, etc., can be detected using an acceleration sensor 216 and a rate gyro 217. Regarding attitude, the tri-axial gravitational force components of the acceleration sensor 216 are measured, and the inclination of the body is found. Regarding the walking condition, the gravitational direction output of the acceleration sensor 216 is analyzed to determine whether the condition is stationary or walking, and if walking, whether climbing stairs or descending stairs.

The rate gyro 217 is used to find the line of movement of a human body, in the same way as in a vehicle navigation system. The built-in sensor signals are analyzed by a signal processor 219 and transmitted from an antenna 218 as various kinds of state information.

An alarm buzzer 220 alerts the person to which the unit is attached if there is no movement of the body for a long time, for instance, and if there is no reaction, such as executing a reset, an abnormal state signal is transmitted from the antenna 218. When this abnormal state signal is received, action can be taken to check the well-being of the person, or an outside party can be notified.

In this embodiment, a combination of acceleration sensor and rate gyro has been described, but the present invention is not limited to this, and it is possible, for example, to capture attitude information with an angle-of-inclination sensor.

It is also possible to capture information from an external sensor via a sensor interface for an optional sensor 221. For example, it is possible for a body temperature sensor using a heart rate sensor and temperature sensor, and a perspiration sensor using a humidity sensor, to be incorporated within a watch-type sensor unit, worn on the wrist, and so capture the above described sensor information from the sensor interface for an optional sensor 221. In this case, either capture by cable or capture by wireless is, of course, possible. Also, there are no particular restrictions on where the state specifying unitis attached, as long as it is somewhere on the body.

(Embodiment 16)

Figure 27:
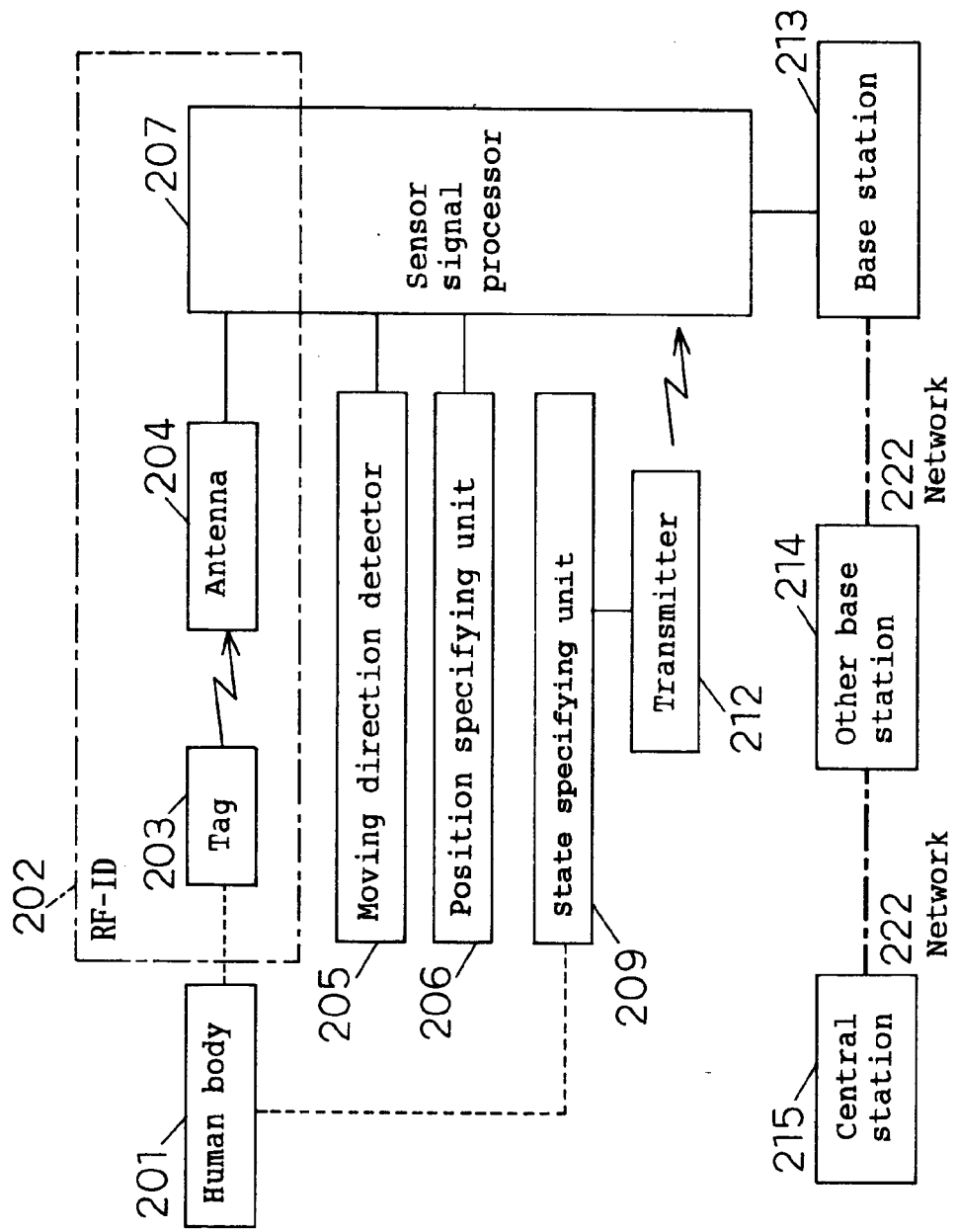
FIG. 27 is an outline type drawing of the behavior information specifying apparatus in embodiment 16 of the present invention.
Figure 28:
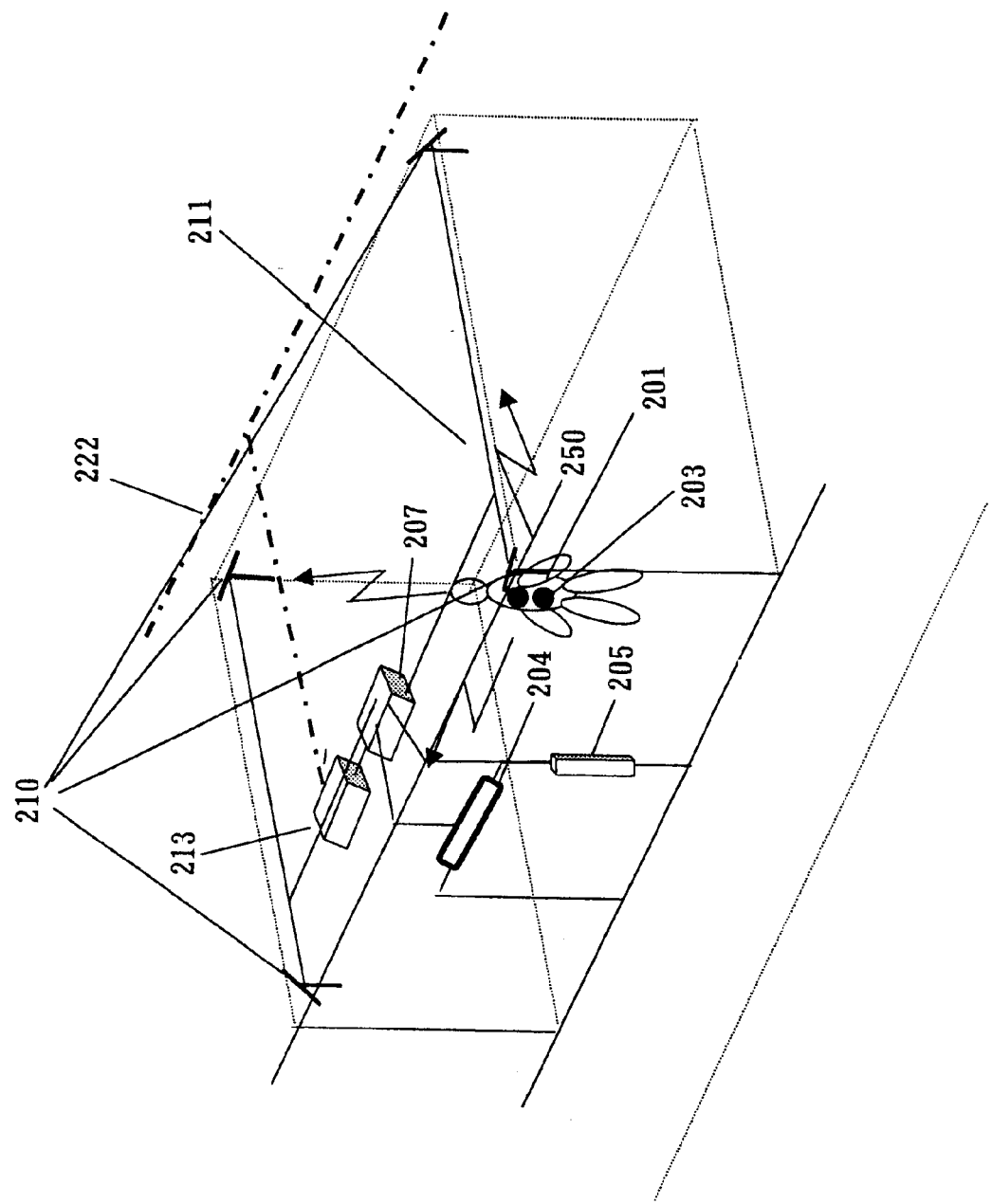
FIG. 28 is an outline type drawing of the behavior information specifying apparatus in embodiment 16 of the present invention.

Network connection with the behavior information specifying apparatus according to embodiment 16 will now be described with reference to the drawings. FIGS. 27 and 28 show outline type drawings of the behavior state specifying unit in one embodiment of the present invention. The behavior information specifying apparatus described up to embodiment 15 is connected to a base station 213 via the sensor signal processor 207. These base stations 213 are installed in individual rooms.

This base station 213 and another base station 214, installed in a different room, are connected in a network, and are further connected to a central station 215. By means of this kind of network connection, the information of each room can all be shared, and the state of all rooms can also be ascertained at the central station. If a display device such as a monitor is installed in the central station, the state of individual rooms can be seen. This can greatly ease the burden, not only on the family, but also on the nursing staff at facilities for taking care of senior citizens, and so forth. In this implementation example, nothing in particular has been said regarding the kind of network, and there are no particular restrictions on this.

As is clear from the above descriptions, the present invention can provide a behavior determining apparatus for accurately detecting the behavior of a subject person.

Also, the present invention can provide a care system for accurately specifying the behavior of a subject person and taking care of that person. In addition, the present invention can provide a care residence equipped with that care system.

Also, the present invention can provide a behavior determining apparatus for notifying, if any behavior of the subject person or any action of the subject device is not substantially identical with a pre-recorded pattern, that non-identity, and permitting the inputting of a response to that notification.

The present invention can further provide a behavior determining apparatus for adding, on the basis of the subject person's response to the notification, the behavior of the subject person or the action of the subject device not substantially identical with the pre-recorded pattern to the records as a new element of pattern, or replacing all or part of the recorded pattern with a new pattern or a new element of pattern.

In addition, the present invention can provide a care system for accurately specifying any behavior of the subject person, accurately notifying the behavior, permitting the inputting of the person's response to the notification, and providing care to the person on the basis of that response. The present invention can further provide a care residence equipped with that care system.

Further, highly reliable, low-cost behavior state detection is possible by means of the behavior information specifying apparatus of the present invention.

What is claimed is:

1. A behavior determining apparatus, comprising:

first detective means for detecting behavior of a given subject person, said first detective means including an infrared ray sensor for detecting movement of said subject person;

second detective means for detecting operation of a given appliance;

recording means for recording one or more combined patterns of behavior of said subject person and operation of said appliance;

determining means for comparing said behavior of said subject person detected by said first detective means and said operation of said appliance detected by said second detective means with patterns recorded in said recording means to determine whether or not a combination of behavior of said subject person and operation of said appliance substantially accords with any of said patterns;

output means for outputting a determined result of said determining means;

first transmitter/receiver means, disposable on a ceiling above a doorway which divides at least two areas, for transmitting a radio wave to a given space when said infrared ray sensor detects said behavior, and for receiving an information item by another radio wave; and second transmitter/receiver means bearable by said subject person, said second transmitter/receiver means including a personal information terminal (PIT) for receiving the radio wave transmitted by said first transmitter/receiver means and responding by transmitting said information item including an ID number identifying said subject person who has said PIT by said another radio wave; wherein the radio wave transmitted by said first transmitter/receiver means includes a command to allow said PIT to transmit said information item, said first transmitter/receiver means receives said ID number when transmitted by said second transmitter/receiver means, and said first detective means specifies said subject person whose behavior is detected when said ID number is received by said first transmitter/receiver means.

2. A behavior determining apparatus as set forth in claim 1, further comprising:

alarm transmitter means for transmitting an alarm by a radio wave in accordance with the determined result of said determining means; and alarm receiver means bearable by said subject person for receiving said alarm by said radio wave.

3. A behavior determining apparatus as set forth in claim 1, further comprising:

notifying means for notifying an alarm by an audio or optical signal in accordance with the determined result of said determining means to the residential space where said subject person behaves.

4. A behavior determining apparatus as set forth in claim 1, further comprising:

notifying means for notifying an alarm by using a telephone line, an electric light or a private line in accordance with the determined result determined by said determining means to outside of the residential space where said subject person behaves.

5. A behavior determining apparatus as set forth in claim 1, further comprising:

third detective means for detecting the physiological state of said subject person and/or the psychological state of said subject person, wherein said pattern is a combined pattern of behavior of said subject person, operation of said appliance and physiological state of said subject person and/or psychological state of said subject person, and said determining means compares the behavior of said subject person the operation of said appliance and the physiological state of said subject person and/or the psychological state of said subject person with patterns recorded in the recording means to determine whether a combination of behavior of said subject person, operation of said appliance and physiological state of said subject person and/or the psychological state of said subject person substantially accords with any of said patterns or not.

6. A behavior determining apparatus as set forth in claim 5, wherein said third detective means specifies said subject person by using said ID number received by said first receiver/transmitter means and detects the physiological state of said subject person and/or the physiological state of said subject person.

7. A behavior determining apparatus as set forth in claim 1, wherein said PIT has all or part of the functions for detecting the posture, the moving condition and the active mass of said subject person bearing it.

8. A behavior determining apparatus as set forth in claim 1, wherein transmitting/receiving of information item by said PIT is performed in the communication shape of a PHS system or in the communication shape of a specific small electric power using frequency zone of several hundred MHz.

* * * * *

UNITED STATES PATENT AND TRADEMARK OFFICE
CERTIFICATE OF CORRECTION

PATENT NO. : 6,796,799 B1
DATED : September 28, 2004
INVENTOR(S) : Nobuyuki Yoshiike et al.

It is certified that error appears in the above-identified patent and that said Letters Patent is hereby corrected as shown below:

Title page,
Item [56], References Cited, OTHER PUBLICATIONS, "M. Makikawa" reference, correct the misspelled word "Activites" to -- Activities --.

Signed and Sealed this

Fifteenth Day of November, 2005

JON W. DUDAS
*Director of the United States Patent and Trademark Office*